US012680097B2

(12) United States Patent
Adey et al.

(10) Patent No.: US 12,680,097 B2
(45) Date of Patent: Jul. 14, 2026

(54) METHODS FOR INCREASING YIELD OF SEQUENCING LIBRARIES

(71) Applicants: Illumina, Inc., San Diego, CA (US); Illumina Cambridge Limited, Cambridge (GB); Oregon Health and Science University, Portland, OR (US)

(72) Inventors: Andrew C. Adey, Portland, OR (US); Ryan Mulqueen, Portland, OR (US); Frank Steemers, San Diego, CA (US); Dmitry K Pokholok, San Diego, CA (US); Fan Zhang, San Diego, CA (US); Esther Musgrave-Brown, Cambridge (GB)

(73) Assignees: Illumina, Inc., San Diego, CA (US); Illumina Cambridge Limited, Cambridge (GB); Oregon Health and Science University, Portland, OR (US)

( * ) Notice: Subject to any disclaimer, the term of this patent is extended or adjusted under 35 U.S.C. 154(b) by 1293 days.

(21) Appl. No.: 17/344,030

(22) Filed: Jun. 10, 2021

(65) Prior Publication Data

US 2021/0380972 A1     Dec. 9, 2021

Related U.S. Application Data

(63) Continuation of application No. PCT/US2021/036599, filed on Jun. 9, 2021.

(60) Provisional application No. 63/036,710, filed on Jun. 9, 2020.

(51) Int. Cl.
| | |
|---|---|
| *C12N 15/10* | (2006.01) |
| *C12Q 1/6855* | (2018.01) |
| *C12Q 1/6869* | (2018.01) |

(52) U.S. Cl.
CPC ..... *C12N 15/1068* (2013.01); *C12N 15/1072* (2013.01); *C12Q 1/6855* (2013.01); *C12Q 1/6869* (2013.01)

(58) Field of Classification Search
None
See application file for complete search history.

(56) References Cited

U.S. PATENT DOCUMENTS

| | | | |
|---|---|---|---|
| 10,208,337 B2 | 2/2019 | Makarov et al. | |
| 10,900,065 B2 | 1/2021 | Seelig et al. | |
| 11,535,883 B2 | 12/2022 | Adey et al. | |
| 11,634,707 B2 | 4/2023 | Gunderson et al. | |
| 2014/0162897 A1* | 6/2014 | Grunenwald | C12N 15/10 |
| | | | 506/9 |
| 2014/0274807 A1 | 9/2014 | Stephens et al. | |
| 2018/0023119 A1* | 1/2018 | Adey | C12Q 1/6806 |
| | | | 506/16 |
| 2018/0334711 A1 | 11/2018 | Kelley et al. | |
| 2018/0355348 A1 | 12/2018 | Adey et al. | |
| 2019/0382753 A1 | 12/2019 | Steemers et al. | |
| 2021/0102194 A1 | 4/2021 | Steemers et al. | |
| 2022/0033805 A1 | 2/2022 | Srivatsan et al. | |
| 2022/0356461 A1 | 11/2022 | Shendure et al. | |

FOREIGN PATENT DOCUMENTS

| | | |
|---|---|---|
| WO | 2010048605 A1 | 4/2010 |
| WO | 2016130704 A2 | 8/2016 |
| WO | WO2020043803 A1 * | 8/2018 |
| WO | 2019033062 A2 | 2/2019 |
| WO | 2021252617 A1 | 12/2021 |

OTHER PUBLICATIONS

Latorra et al (Design considerations and effects of LNA in PCR primers, Molecular and Cellular Probes, 17, 253-259) (Year: 2003).*
ThermoFisher Scientific (Thermo Scientific Phusion DNA Polymerases) (Year: 2015).*
Cusanovich et al., "Multiplex single-cell profiling of chromatin accessibility by combinatorial cellular indexing," Science, May 22, 2015, vol. 348, No. 6237, pp. 910-914.
Gruz et al., "Processing of DNA lesions by archaeal DNA polymerases from Sulfolobus solfataricus," Nucleic Acids Research, 2003, vol. 31, No. 14, pp. 4024-4030.
Heyn et al., "Road blocks on paleogenomes—polymerase extension profiling reveals the frequency of blocking lesions in ancient DNA," Nucleic Acids Research, 2010, vol. 38, No. 16, pp. 1-10.
International Preliminary Report on Patentability for PCT/US2021/036599, issued Dec. 13, 2022, 9 pages.
International Search Report and Written Opinion for PCT/US2021/036599, issued Sep. 24, 2021, 18 pages.
Mulqueen et al., "High-content single-cell combinatorial indexing," Nature Biotechnology, 2021, vol. 39, No. 12, pp. 1574-1580.
Mulqueen et al., "Highly scalable generation of DNA methylation profiles in single cells," Nature Biotechnology, Jun. 2018, vol. 36, No. 5, pp. 428-431.
Sikorsky et al., "DNA damage reduces Taq DNA polymerase fidelity and PCR amplification efficiency," Biochemical and Biophysical Research Communications, 2007, vol. 355, No. 2, pp. 431-437.
Vitak et al. "Sequencing thousands of single-cell genomes with combinatorial indexing," Nature Methods, Mar. 2017, vol. 14, No. 3, pp. 302-308.
Zatopek et al., "RADAR-seq: A RARe DAmage and Repair Sequencing method for detecting DNA damage on a genome-wide scale," DNA Repair, 2019, vol. 80, pp. 36-44.

* cited by examiner

*Primary Examiner* — Juliet C Switzer
*Assistant Examiner* — Brian Ellis Young
(74) *Attorney, Agent, or Firm* — Illumina, Inc.

(57)     ABSTRACT

The present disclosure is concerned with compositions, methods, and kits for preparing a sequencing library. In one embodiment, methods include producing a library of target nucleic acids having the same adapter at each end and then switching the identity of one adapter to result in target nucleic acids flanked by distinct adapters.

19 Claims, 33 Drawing Sheets
Specification includes a Sequence Listing.

FIG. 1

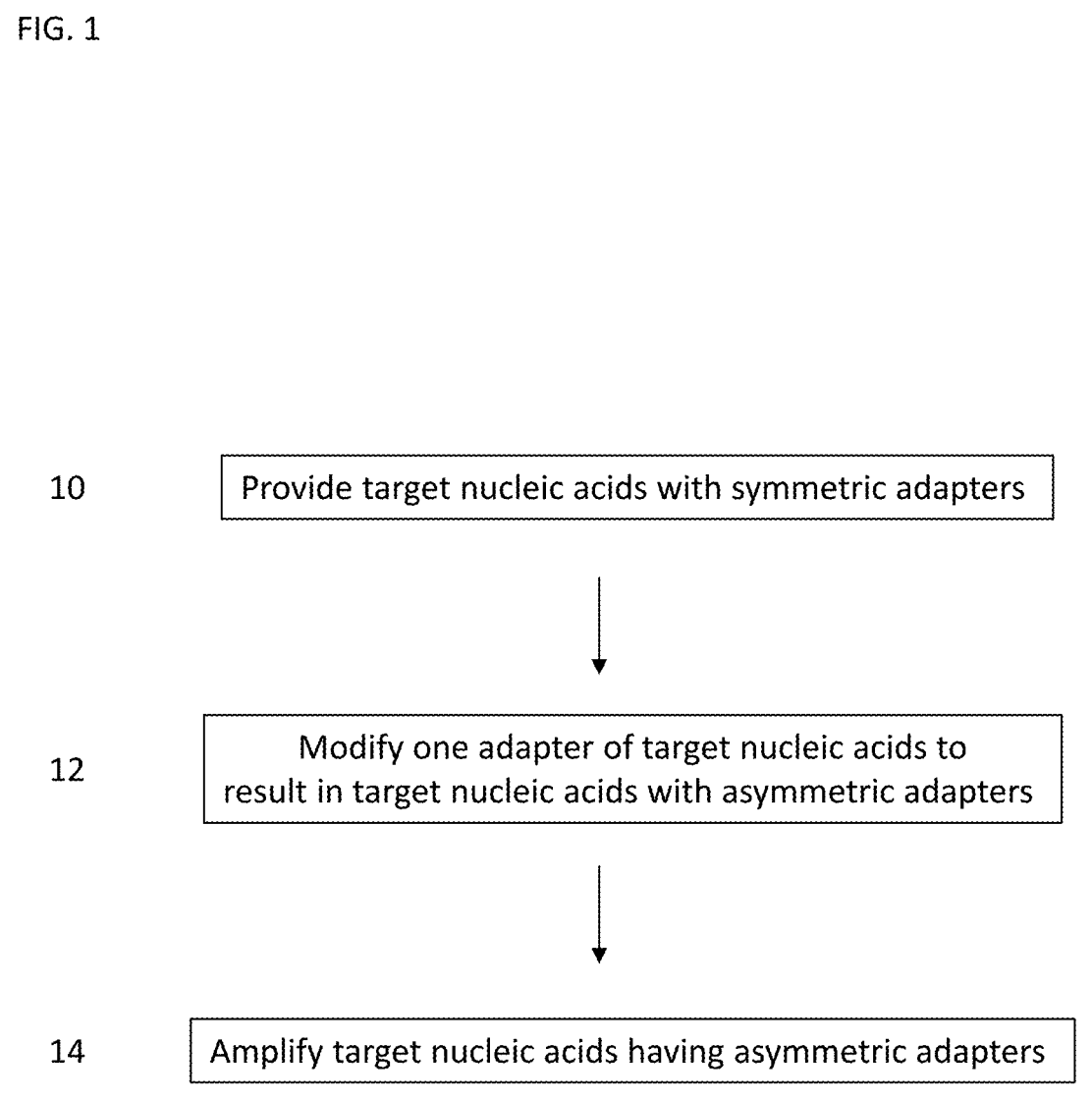

10      | Provide target nucleic acids with symmetric adapters |

12      | Modify one adapter of target nucleic acids to result in target nucleic acids with asymmetric adapters |

14      | Amplify target nucleic acids having asymmetric adapters |

FIG. 3
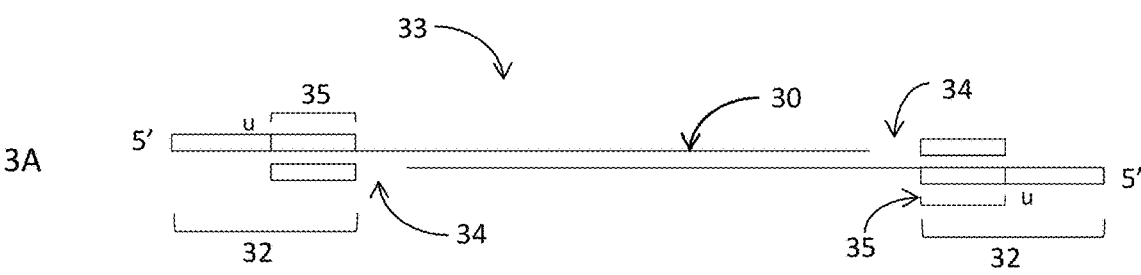
3A
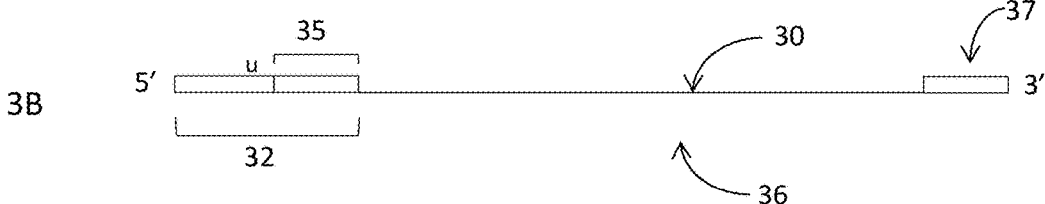
3B
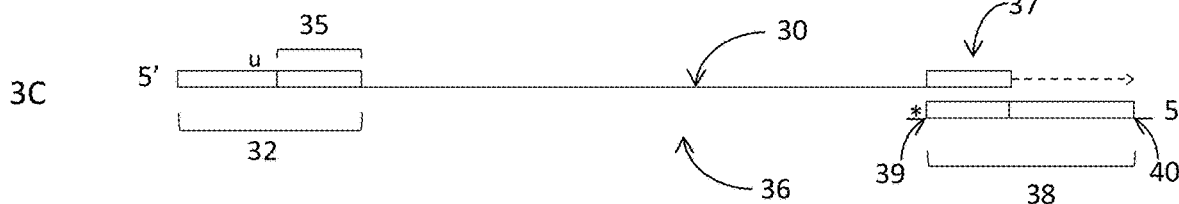
3C
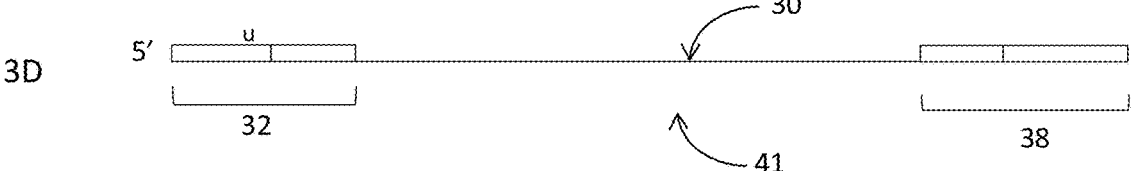
3D

50     Provide DNA present in isolated nuclei or cells

51     Distribute subsets of isolated nuclei or cells

52     Add symmetric adapter with index to DNA

53     Pool and distribute indexed nuclei or cells

54     Convert target nucleic acids to include asymmetric adapter with index

55     Amplify target nucleic acids having asymmetric adapters

FIG. 8A                    Indexed Reversed Transcription (96x)
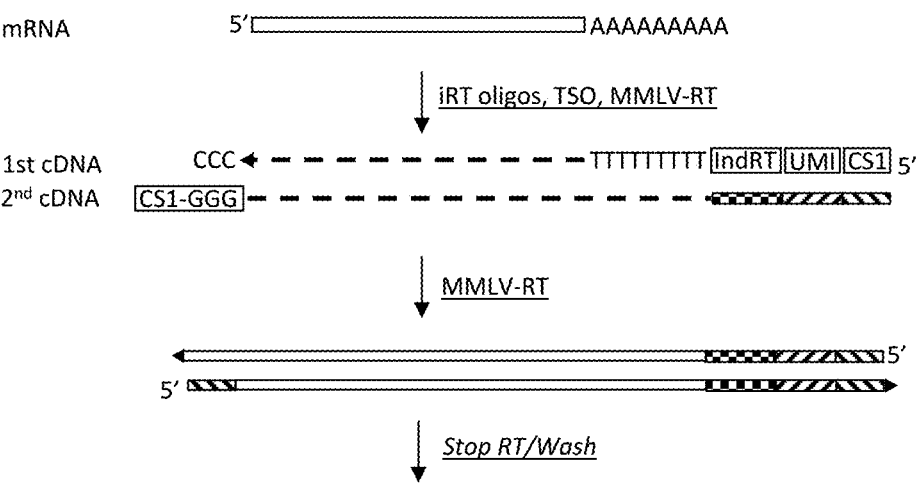
FIG. 8B          Indexed Tagmentation with i7 TSM in the same wells (96x)
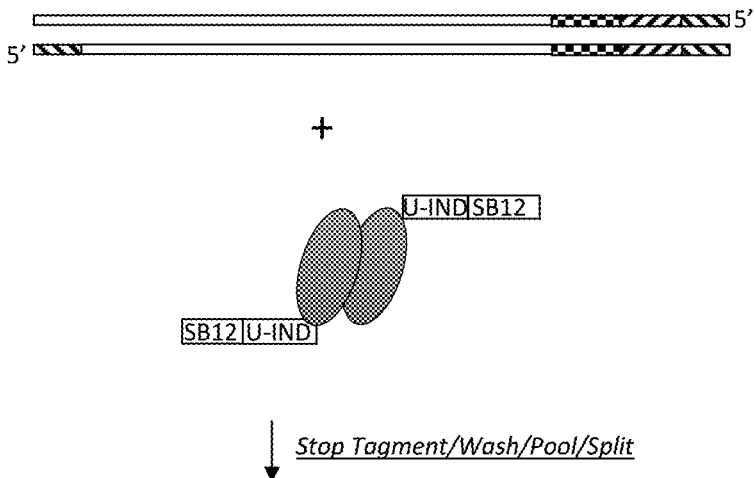

FIG. 8C          Convert adapters BB -> AB
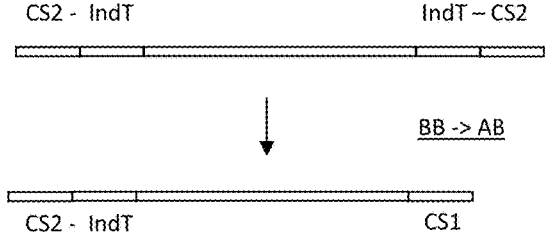
FIG. 8D          Indexed PCR (96x/384x/1536x)
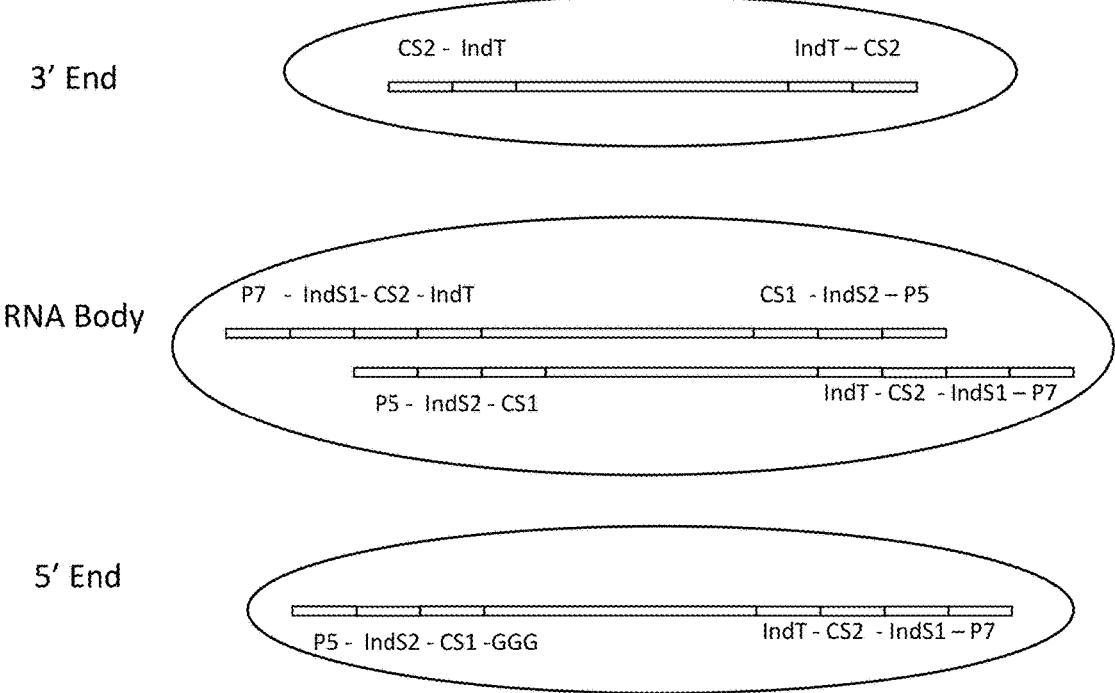

Fixation

↓

Digestion

↓

Proximity ligation

↓

Nucleosome depletion and *in situ* tagmentation

↓ S3 protocol

FIG. 12
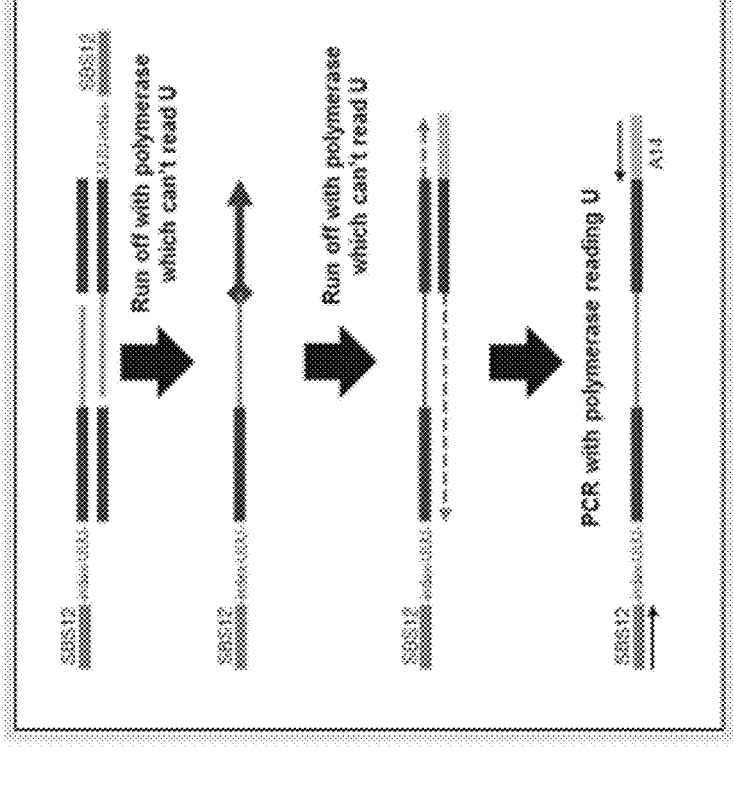
AA to AB test
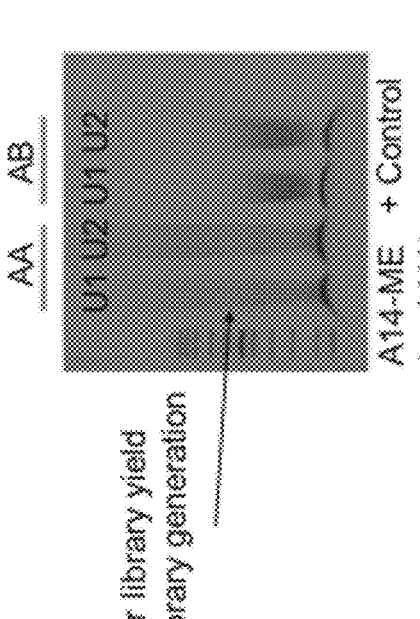
Poor library yield
& library generation
A14-ME    + Control
(no LNA)
➢ gDNA tagmented by either AA TSM or AB TSM
➢ 0.01% SDS NPM 1ˢᵗ extension @72c
➢ Spike in A14-ME, 98c denature, 2ⁿᵈ extension
   @45c, 5x
➢ Add 0.1% TX-100 to neutralize SDS, Taq
   qPCR, 25x, and run gel FIG. 13
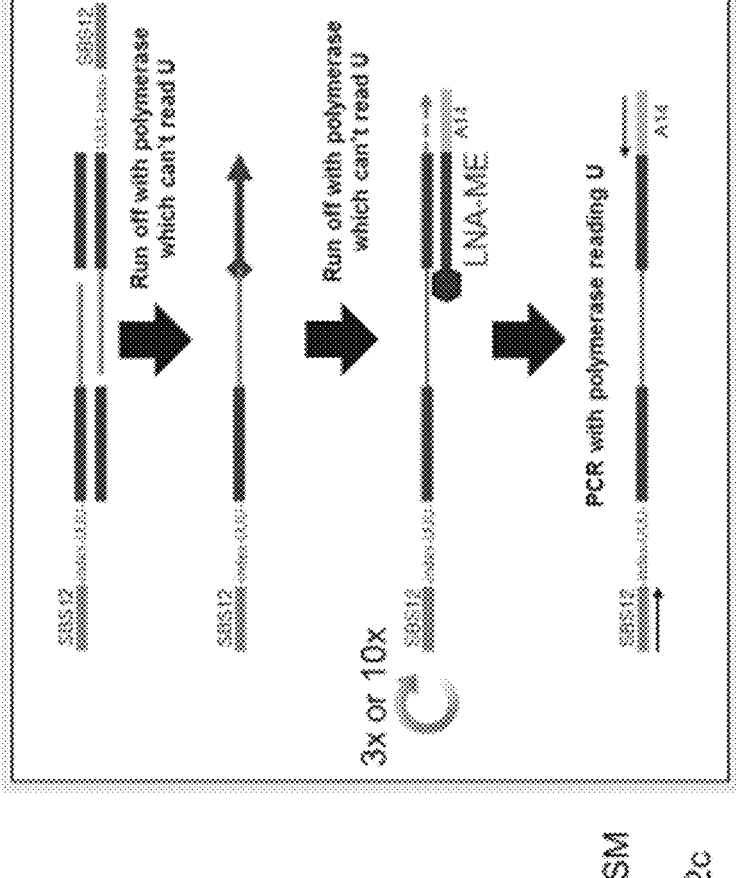
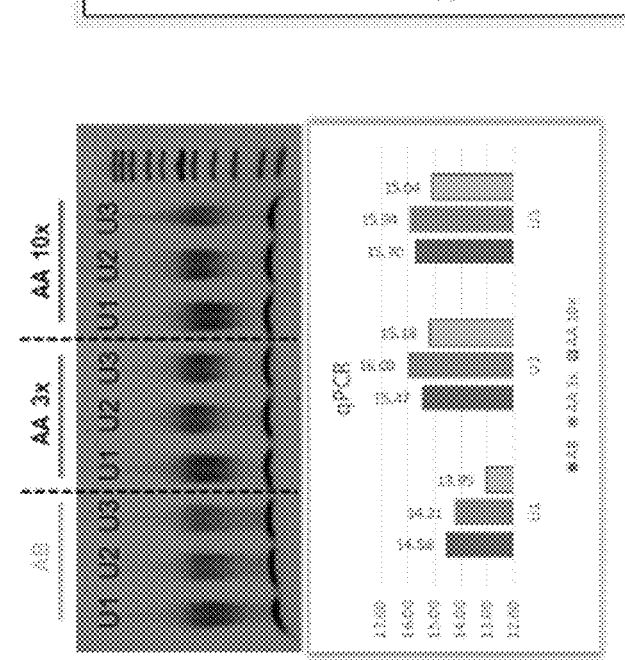
AA to AB (LNA-ME)
➤ gDNA tagmented by either AA TSM (SBS12 TSM) or AB TSM (SBS12 TSM + A14 TSM)
➤ 0.01% SDS NPM 1st extension @72c
➤ Spike in A14-ME, 98c denature, 2nd extension @53c;3x or 10x
➤ Add 0.1% TX-100 to neutralize SDS. Taq qPCR, 25x, and run gel

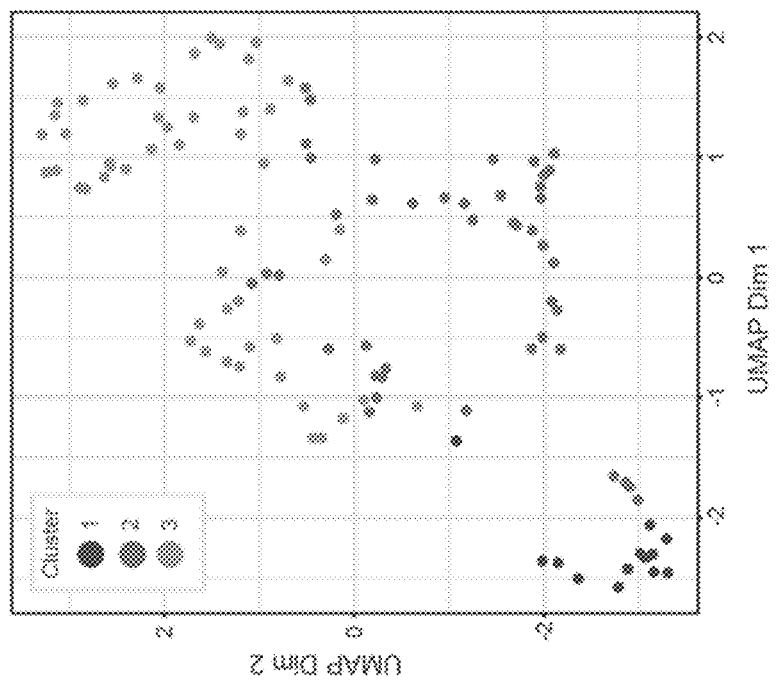
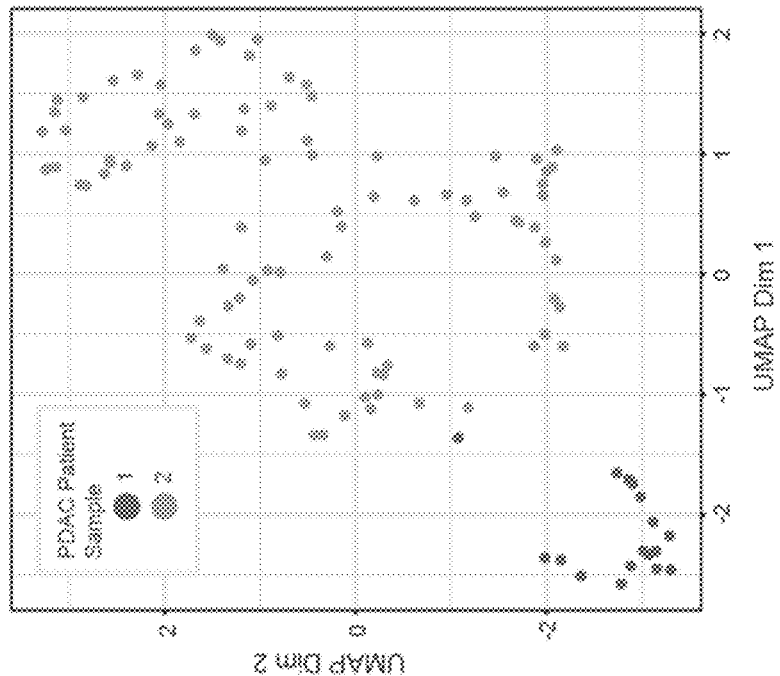
FIG. 28

FIG. 29

AATGATACGGCGACCACCGAGATCTACACTAGATCGCTCGT
CGGCAGCGTCUAGATGTGTATAAGAGACAG (SEQ ID NO: 1)

CAAGCAGAAGACGGCATACGAGATTCGCCTTAGTCTCGTGG
GCTCGGAGATGTGTATAAGAGACAG  (SEQ ID NO: 2)

P5: AATGATACGGCGACCACCGAGATCTACAC (SEQ ID NO:3)

i5: TAGATCGC (SEQ ID NO:4)

P7: CAAGCAGAAGACGGCATACGAGA (SEQ ID NO:5)

i7: TTCGCCTTA (SEQ ID NO:6)

ME: AGATGTGTATAAGAGACAG (SEQ ID NO:7)

A14:  TCGTCGGCAGCGTC (SEQ ID NO:8)

B15: GTCTCGTGGGCTCGG (SEQ ID NO:9)

SEQUENCE LISTING

```
<160> NUMBER OF SEQ ID NOS: 9

<210> SEQ ID NO 1
<211> LENGTH: 71
<212> TYPE: DNA
<213> ORGANISM: artificial
<220> FEATURE:
<223> OTHER INFORMATION: oligonucleotide containing P7, i7, B15, and ME

<400> SEQUENCE: 1
aatgatacgg cgaccaccga gatctacact agatcgctcg tcggcagcgt cuagatgtgt      60
ataagagaca g                                                           71

<210> SEQ ID NO 2
<211> LENGTH: 66
<212> TYPE: DNA
<213> ORGANISM: artificial
<220> FEATURE:
<223> OTHER INFORMATION: oligonucleotide containing P7, i7, B15, and ME

<400> SEQUENCE: 2
caagcagaag acggcatacg agattcgcct tagtctcgtg ggctcggaga tgtgtataag      60
agacag                                                                 66
```

-continued

```
<210> SEQ ID NO 3
<211> LENGTH: 29
<212> TYPE: DNA
<213> ORGANISM: artificial
<220> FEATURE:
<223> OTHER INFORMATION: P5

<400> SEQUENCE: 3
aatgatacgg cgaccaccga gatctacac                                      29

<210> SEQ ID NO 4

<400> SEQUENCE: 4

000

<210> SEQ ID NO 5
<211> LENGTH: 23
<212> TYPE: DNA
<213> ORGANISM: artificial
<220> FEATURE:
<223> OTHER INFORMATION: P7

<400> SEQUENCE: 5
caagcagaag acggcatacg aga                                            23

<210> SEQ ID NO 6

<400> SEQUENCE: 6

000

<210> SEQ ID NO 7
<211> LENGTH: 19
<212> TYPE: DNA
<213> ORGANISM: artificial
<220> FEATURE:
<223> OTHER INFORMATION: ME

<400> SEQUENCE: 7
agatgtgtat aagagacag                                                 19

<210> SEQ ID NO 8
<211> LENGTH: 14
<212> TYPE: DNA
<213> ORGANISM: artificial
<220> FEATURE:
<223> OTHER INFORMATION: A14

<400> SEQUENCE: 8
tcgtcggcag cgtc                                                      14

<210> SEQ ID NO 9
<211> LENGTH: 15
<212> TYPE: DNA
<213> ORGANISM: artificial
<220> FEATURE:
<223> OTHER INFORMATION: B15

<400> SEQUENCE: 9
gtctcgtggg ctcgg                                                     15
```

METHODS FOR INCREASING YIELD OF SEQUENCING LIBRARIES

CROSS-REFERENCE TO RELATED APPLICATIONS

This application is a continuation of PCT Application No. PCT/US2021/036599, filed Jun. 9, 2021, which claims the benefit of U.S. Provisional Application Ser. No. 63/036,710, filed Jun. 9, 2020, which is incorporated by reference herein in its entirety.

GOVERNMENT FUNDING

This invention was made with government support under R35GM124704 awarded by the National Institutes of Health. The government has certain rights in the invention.

SEQUENCE LISTING

This application contains a Sequence Listing electronically submitted via Patent Center to the United States Patent and Trademark Office as an ASCII text file entitled "0531_001985US01-ST25.txt" having a size of 1.82 kilobytes (1,866 bytes) and created on Oct. 10, 2025. The information contained in the Sequence Listing is incorporated by reference herein.

FIELD

Embodiments of the present disclosure relate to preparing nucleic acids for sequencing. In particular, embodiments of the methods, compositions, systems, and kits provided herein relate to converting nucleic acid libraries from fragments containing symmetric universal sequences to fragments containing asymmetric universal sequences and obtaining sequence data therefrom.

BACKGROUND

Next-generation sequencing (NGS) technology has revolutionized genome research. One approach to NGS that has proven to be effective is the generation of sequencing libraries where fragments are processed to have a different adapter at each end. Paired-end sequencing is then used to obtain sequence information from both strands. The advantage of the paired-end approach is that there is significantly more information to be gained from sequencing two stretches each of "n" bases from a single template than from sequencing "n" bases from each of two independent templates in a random fashion. Methods for addition of a different adapter to each end, however, are often inefficient as it is difficult to selectively target a first adapter to one end of a DNA fragment and a second adapter to the other end of the same DNA fragment. For instance, sequencing libraries can be produced using highly efficient tagmentation, but viable sequencing library molecules are only produced when different adaptors, in the form of forward or reverse primary sequences, are incorporated at each end of the molecule. During some tagmentation reactions there is an equal probability of incorporating each of the two sequences, thus resulting in half of the molecules having forward-forward or reverse-reverse adaptor combinations and thereby reducing the theoretical yield to 50%.

SUMMARY OF THE APPLICATION

Presented herein are methods and compositions that efficiently convert nucleic acids into sequencing libraries. The methods presented herein include alternative strategies that use adapter replacement to produce libraries of target nucleic acids tagged with both forward and reverse adaptors for the top strand of nucleic acids, bottom strand of nucleic acids, or both the top and bottom strand of nucleic acids. The methods are useful across a wide-range of sequencing library preparation methods including, but not limited to, whole-genome sequencing, genomic conformation capture, circulating DNA sequencing, targeted sequencing, co-assays for two or more analytes, e.g., RNA and ATAC or DNA and RNA, and single cell genomics. Additionally, this format permits the use of one or more index sequence embedded within the adapter, enabling single-cell combinatorial indexing (sci) applications, (examples, Cusanovich, et al., Science 348, 910-914 (2015); Vitak et al., Nat. Methods 14, 302-308 (2017); Mulqueen et al., Nat. Biotechnol. 36, 428-431 (2018)). The methods provided herein result in improvements in data quality, including marked improvements over known methods with respect to passing reads obtained per cell without sacrificing signal enrichment in the case of s3-ATAC, coverage uniformity for s3-WGS, and improved chromatin contacts obtained per cell for s3-GCC when compared to sci-HiC. s3-ATAC, s3-WGS, and s3-GCC are described herein.

Definitions

Terms used herein will be understood to take on their ordinary meaning in the relevant art unless specified otherwise. Several terms used herein and their meanings are set forth below.

As used herein, the terms "organism," "subject," are used interchangeably and refer to microbes (e.g., prokaryotic or eukaryotic) animals and plants. An example of an animal is a mammal, such as a human.

As used herein, the term "target nucleic acid," is intended as a semantic identifier for the nucleic acid in the context of a method or composition set forth herein and does not necessarily limit the structure or function of the nucleic acid beyond what is otherwise explicitly indicated. A target nucleic acid may be essentially any nucleic acid of known or unknown sequence. It may be, for example, a fragment of genomic DNA (e.g., chromosomal DNA), extra-chromosomal DNA such as a plasmid, circulating DNA or circulating RNA, nucleic acids from a cell or cells, cell-free DNA, RNA (e.g., mRNA), or cDNA. Sequencing may result in determination of the sequence of the whole, or a part of the target molecule. The targets can be derived from a primary nucleic acid sample, such as a nucleus. In one embodiment, the targets can be processed into templates suitable for amplification by the placement of universal sequences at the end or ends of each target fragment. The targets can also be obtained from a primary RNA sample by reverse transcription into cDNA. In one embodiment, target is used in reference to a subset of DNA or RNA in the cell. Targeted sequencing uses selection and isolation of genes of interest, typically by either PCR amplification (e.g. region-specific primers) or hybridization-based capture method or antibodies. Targeted enrichment can occur at various stages of the method. For instance, a targeted RNA representation can be obtained using target specific primers in the reverse transcription step or hybridization-based enrichment of a subset out of a more complex library. An example is exone sequencing or the L1000 assay (Subramanian et al., 2017, Cell, 171; 1437-1452). Targeted sequencing can include any of the enrichment processes known to one of ordinary skill in the art. A target nucleic acid having a universal sequence one or both ends can be referred to as a modified target nucleic acid. Reference to a nucleic acid such as a target nucleic acid includes both single stranded and double stranded nucleic acids unless indicated otherwise. For instance, symmetric and asymmetric target nucleic acids can be double-stranded, single stranded, or partly double and single stranded at some point in the method of the present disclosure.

As used herein, the term "adapter" and its derivatives, e.g., universal adapter, refers generally to any linear oligo- nucleotide which can be attached to a target nucleic acid. An adapter can be single-stranded or double-stranded DNA, or can include both double stranded and single stranded regions. An adapter can include a universal sequence that is substantially identical, or substantially complementary, to at least a portion of a primer, for example a universal primer; an index (also referred to herein as a barcode or tag) to assist with downstream error correction, identification, or sequencing; and/or a UMI. In some embodiments, the adapter is substantially non-complementary to the 3' end or the 5' end of any target sequence present in the sample. In some embodiments, suitable adapter lengths are in the range of about 6-100 nucleotides, about 12-60 nucleotides, or about 15-50 nucleotides in length. For instance, The terms "adaptor" and "adapter" are used interchangeably.

As used herein, the term "universal," when used to describe a nucleotide sequence, refers to a region of sequence that is common to two or more nucleic acid molecules where the molecules also have regions of sequence that differ from each other. A universal sequence that is present in different members of a collection of nucleic acids can be used as, for instance, a "landing pad" in a subsequent step to anneal a nucleotide sequence that can be used as a primer for addition of another nucleotide sequence, such as an index, to a target nucleic acid. A universal sequence that is present in different members of a collection of nucleic acids can allow capture of multiple different nucleic acids using a population of universal capture nucleic acids, e.g., capture oligonucleotides that are complementary to a portion of the universal sequence, e.g., a universal capture sequence. Non-limiting examples of universal cap- ture sequences include sequences that are identical to or complementary to P5 and P7 primers. Similarly, a universal sequence present in different members of a collection of molecules can allow the replication (e.g., sequencing) or amplification of multiple different nucleic acids using a population of universal primers that are complementary to a portion of the universal sequence, e.g., a universal anchor sequence. The terms "A14" and "B15" may be used when referring to a universal anchor sequence. The terms "A14'" (A14 prime) and "B15'" (B15 prime) refer to the comple- ment of A14 and B15, respectively. It will be understood that any suitable universal anchor sequence can be used in the methods presented herein, and that the use of A14 and B15 are exemplary embodiments only. In one embodiment uni- versal anchor sequences are used as a site to which a universal primer (e.g., a sequencing primer for read 1 or read 2) anneals for sequencing. A capture oligonucleotide or a universal primer therefore includes a sequence that can hybridize specifically to a universal sequence.

The terms "P5" and "P7" may be used when referring to a universal capture sequence or a capture oligonucleotide. The terms "P5'" (P5 prime) and "P7'" (P7 prime) refer to the complement of P5 and P7, respectively. It will be understood that any suitable universal capture sequence or a capture oligonucleotide can be used in the methods presented herein, and that the use of P5 and P7 are exemplary embodiments only. Uses of capture oligonucleotides such as P5 and P7 or their complements on flowcells are known in the art, as exemplified by the disclosures of WO 2007/010251, WO 2006/064199, WO 2005/065814, WO 2015/106941, WO 1998/044151, and WO 2000/018957. For example, any suitable forward amplification primer, whether immobilized or in solution, can be useful in the methods presented herein for hybridization to a complementary sequence and ampli- fication of a sequence. Similarly, any suitable reverse ampli- fication primer, whether immobilized or in solution, can be useful in the methods presented herein for hybridization to a complementary sequence and amplification of a sequence. One of skill in the art will understand how to design and use primer sequences that are suitable for capture and/or ampli- fication of nucleic acids as presented herein.

As used herein, the term "primer" and its derivatives refer generally to any nucleic acid that can hybridize to a target sequence of interest. Typically, the primer functions as a substrate onto which nucleotides can be polymerized by a polymerase or to which a polynucleotide can be ligated; in some embodiments, however, the primer can become incor- porated into the synthesized nucleic acid strand and provide a site to which another primer can hybridize to prime synthesis of a new strand that is complementary to the synthesized nucleic acid molecule. The primer can include any combination of nucleotides or analogs thereof. In some embodiments, the primer is a single-stranded oligonucle- otide or polynucleotide. The terms "polynucleotide" and "oligonucleotide" are used interchangeably herein to refer to a polymeric form of nucleotides of any length, and may include ribonucleotides, deoxyribonucleotides, analogs thereof, or mixtures thereof. The terms should be understood to include, as equivalents, analogs of either DNA, RNA, cDNA, or antibody-oligo conjugates made from nucleotide analogs and to be applicable to single stranded (such as sense or antisense) and double stranded polynucleotides. The term as used herein also encompasses cDNA, that is complementary or copy DNA produced from a RNA tem- plate, for example by the action of reverse transcriptase. This term refers only to the primary structure of the molecule. Thus, the term includes triple-, double- and single-stranded deoxyribonucleic acid ("DNA"), as well as triple-, double- and single-stranded ribonucleic acid ("RNA").

As used herein, an "index" (also referred to as an "index region," "index adaptor," "tag," or a "barcode") refers to a unique nucleic acid tag that can be used to identify a sample or source of the nucleic acid material, or a compartment in which a target nucleic acid was present. The index can be present in solution or on a solid-support, or attached to or associated with a solid-support and released in solution or compartment. When nucleic acid samples are derived from multiple sources, the nucleic acids in each nucleic acid sample can be tagged with different nucleic acid tags such that the source of the sample can be identified. Any suitable index or set of indexes can be used, as known in the art and as exemplified by the disclosures of U.S. Pat. No. 8,053,192, PCT Publication No. WO 05/068656, and U.S. Pat. Publi- cation No. 2013/0274117. In some embodiments, an index can include a six-base Index 1 (i7) sequence, an eight-base Index 1 (i7) sequence, an eight-base Index 2 (i5e) sequence, a ten-base Index 1 (i7) sequence, or a ten-base Index 2 (i5) sequence from ILLUMINA®, Inc. (San Diego, CA).

As used herein, the term "unique molecular identifier" or "UMI" refers to a molecular tag, either random, non-ran- dom, or semi-random, that may be attached to a nucleic acid. When incorporated into a nucleic acid, a UMI can be used to correct for subsequent amplification bias by directly counting unique molecular identifiers (UMIs) that are sequenced after amplification. A UMI can be attached to similar nucleic acids, e.g., adapters, making each nucleic acid unique.

As used herein, the term "amplicon," when used in reference to a nucleic acid, means the product of copying the nucleic acid, wherein the product has a nucleotide sequence that is the same as or complementary to at least a portion of the nucleotide sequence of the nucleic acid. An amplicon can be produced by any of a variety of amplification methods that use the nucleic acid, or an amplicon thereof, as a template including, for example, polymerase extension, polymerase chain reaction (PCR), rolling circle amplification (RCA), ligation extension, or ligation chain reaction. An amplicon can be a nucleic acid molecule having a single copy of a particular nucleotide sequence (e.g. a PCR product) or multiple copies of the nucleotide sequence (e.g. a concatameric product of RCA). A first amplicon of a target nucleic acid is typically a complementary copy. Subsequent amplicons are copies that are created, after generation of the first amplicon, from the target nucleic acid or from the first amplicon. A subsequent amplicon can have a sequence that is substantially complementary to the target nucleic acid or substantially identical to the target nucleic acid.

As used herein, "amplify", "amplifying" or "amplification reaction" and their derivatives, refer generally to any action or process whereby at least a portion of a nucleic acid molecule is replicated or copied into at least one additional nucleic acid molecule. The additional nucleic acid molecule optionally includes sequence that is substantially identical or substantially complementary to at least some portion of the template nucleic acid molecule. The template nucleic acid molecule can be single-stranded or double-stranded and the additional nucleic acid molecule can independently be single-stranded or double-stranded. Amplification optionally includes linear or exponential replication of a nucleic acid molecule. In some embodiments, such amplification can be performed using isothermal conditions; in other embodiments, such amplification can include thermocycling. In some embodiments, the amplification is a multiplex amplification that includes the simultaneous amplification of a plurality of target sequences in a single amplification reaction. In some embodiments, "amplification" includes amplification of at least some portion of DNA and RNA based nucleic acids alone, or in combination. The amplification reaction can include any of the amplification processes known to one of ordinary skill in the art. In some embodiments, the amplification reaction includes polymerase chain reaction (PCR).

As used herein, the term "polymerase chain reaction" ("PCR") refers to the method of Mullis U.S. Pat. Nos. 4,683,195 and 4,683,202, which describe a method for increasing the concentration of a segment of a polynucleotide of interest in a mixture of genomic DNA without cloning or purification. This process for amplifying the polynucleotide of interest consists of introducing a large excess of two oligonucleotide primers to the DNA mixture containing the desired polynucleotide of interest, followed by a series of thermal cycling in the presence of a DNA polymerase. The two primers are complementary to their respective strands of the double stranded polynucleotide of interest. The mixture is denatured at a higher temperature first and the primers are then annealed to complementary sequences within the polynucleotide of interest molecule. Following annealing, the primers are extended with a polymerase to form a new pair of complementary strands. The steps of denaturation, primer annealing and polymerase extension can be repeated many times (referred to as thermocycling) to obtain a high concentration of an amplified segment of the desired polynucleotide of interest. The length of the amplified segment of the desired polynucleotide of interest (amplicon) is determined by the relative positions of the primers with respect to each other, and therefore, this length is a controllable parameter. By virtue of repeating the process, the method is referred to as PCR. Because the desired amplified segments of the polynucleotide of interest become the predominant nucleic acid sequences (in terms of concentration) in the mixture, they are said to be "PCR amplified". In a modification to the method discussed above, the target nucleic acid molecules can be PCR amplified using a plurality of different primer pairs, in some cases, one or more primer pairs per target nucleic acid molecule of interest, thereby forming a multiplex PCR reaction.

As used herein, "amplification conditions" and its derivatives, generally refers to conditions suitable for amplifying one or more nucleic acid sequences. Such amplification can be linear or exponential. In some embodiments, the amplification conditions can include isothermal conditions or alternatively can include thermocycling conditions, or a combination of isothermal and thermocycling conditions. In some embodiments, the conditions suitable for amplifying one or more nucleic acid sequences include polymerase chain reaction (PCR) conditions. Typically, the amplification conditions refer to a reaction mixture that is sufficient to amplify nucleic acids such as one or more target sequences flanked by a universal sequence, or target specific primers, or to amplify an amplified target sequence flanked by one or more adapters. Generally, the amplification conditions include a catalyst for amplification or for nucleic acid synthesis, for example a polymerase; a primer that possesses some degree of complementarity to the nucleic acid to be amplified; and nucleotides, such as deoxyribonucleotide triphosphates (dNTPs) to promote extension of the primer once hybridized to the nucleic acid. The amplification conditions can require hybridization or annealing of a primer to a nucleic acid, extension of the primer and a denaturing step in which the extended primer is separated from the nucleic acid sequence undergoing amplification. Typically, but not necessarily, amplification conditions can include thermocycling; in some embodiments, amplification conditions include a plurality of cycles where the steps of annealing, extending and separating are repeated. Typically, the amplification conditions include cations such as $Mg^{2+}$ or $Mn^{2+}$ and can also include various modifiers of ionic strength.

As defined herein "multiplex amplification" refers to selective and non-random amplification of two or more target sequences within a sample using at least one target-specific primer. In some embodiments, multiplex amplification is performed such that some or all of the target sequences are amplified within a single reaction vessel. The "plexy" or "plex" of a given multiplex amplification refers generally to the number of different target-specific sequences that are amplified during that single multiplex amplification. In some embodiments, the plexy can be about 12-plex, 24-plex, 48-plex, 96-plex, 192-plex, 384-plex, 768-plex, 1536-plex, 3072-plex, 6144-plex or higher. It is also possible to detect the amplified target sequences by several different methodologies (e.g., gel electrophoresis followed by densitometry, quantitation with a bioanalyzer or quantitative PCR, hybridization with a labeled probe; incorporation of biotinylated primers followed by avidin-enzyme conjugate detection; incorporation of $^{32}P$-labeled deoxynucleotide triphosphates into the amplified target sequence).

As used herein, the term "amplification site" refers to a site in or on an array where one or more amplicons can be generated. An amplification site can be further configured to contain, hold or attach at least one amplicon that is generated at the site.

As used herein, the term "array" refers to a population of sites that can be differentiated from each other according to relative location. Different molecules that are at different sites of an array can be differentiated from each other according to the locations of the sites in the array. An individual site of an array can include one or more molecules of a particular type. For example, a site can include a single target nucleic acid molecule having a particular sequence or a site can include several nucleic acid molecules having the same sequence (and/or complementary sequence, thereof). The sites of an array can be different features located on the same substrate. Exemplary features include without limitation, droplets, wells in a substrate, beads (or other particles) in or on a substrate, projections from a substrate, ridges on a substrate or channels in a substrate. The sites of an array can be separate substrates each bearing a different molecule. Different molecules attached to separate substrates can be identified according to the locations of the substrates on a surface to which the substrates are associated or according to the locations of the substrates in a liquid or gel. Exemplary arrays in which separate substrates are located on a surface include, without limitation, those having beads in wells.

As used herein, the term "compartment" is intended to mean an area or volume that separates or isolates something from other things. Exemplary compartments include, but are not limited to, vials, tubes, wells, droplets, boluses, beads, vessels, surface features, flow cell, or areas or volumes separated by physical forces such as fluid flow, magnetism, electrical current or the like. In one embodiment, a compartment is a well of a multi-well plate, such as a 96- or 384-well plate. As used herein, a droplet may include a hydrogel bead, which is a bead for encapsulating one or more nuclei or cell, and includes a hydrogel composition. In some embodiments, the droplet is a homogeneous droplet of hydrogel material or is a hollow droplet having a polymer hydrogel shell. Whether homogenous or hollow, a droplet may be capable of encapsulating one or more nuclei or cells. In some embodiments, the droplet is a surfactant stabilized droplet. In some embodiments, a single cell or Nuclei is present per compartment. In some embodiments, two or more cells or Nuclei are present per compartment. In some embodiments, each compartment contains a compartment-specific index. In some embodiments, the index is in solution or attached or associated with a solid-phase in each compartment.

The term "flow cell" as used herein refers to a chamber comprising a solid surface across which one or more fluid reagents can be flowed. Examples of flow cells and related fluidic systems and detection platforms that can be readily used in the methods of the present disclosure are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082.

As used herein, the term "clonal population" refers to a population of nucleic acids that is homogeneous with respect to a particular nucleotide sequence. The homogenous sequence is typically at least 10 nucleotides long, but can be even longer including for example, at least 50, 100, 250, 500 or 1000 nucleotides long. A clonal population can be derived from a single target nucleic acid or template nucleic acid.

Typically, all of the nucleic acids in a clonal population will have the same nucleotide sequence. It will be understood that a small number of mutations (e.g. due to amplification artifacts) can occur in a clonal population without departing from clonality.

As used herein, the term "each," when used in reference to a collection of items, is intended to identify an individual item in the collection but does not necessarily refer to every item in the collection unless the context clearly dictates otherwise.

As used in this specification and the appended claims, the term "or" is generally employed in its sense including "and/or" unless the content clearly dictates otherwise. The term "and/or" means one or all of the listed elements or a combination of any two or more of the listed elements. The use of "and/or" in some instances does not imply that the use of "or" in other instances may not mean "and/or."

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the present disclosure.

As used herein, "have," "has," "having," "include," "includes," "including," "comprise," "comprises," "comprising" and the like are used in their open ended inclusive sense, and generally mean "include, but not limited to," "includes, but not limited to," or "including, but not limited to."

It is understood that wherever embodiments are described herein with the language "have," "has," "having," "include," "includes," "including," "comprise," "comprises," "comprising" and the like, otherwise analogous embodiments described in terms of "consisting of" and/or "consisting essentially of" are also provided. The term "consisting of" means including, and limited to, whatever follows the phrase "consisting of." That is, "consisting of" indicates that the listed elements are required or mandatory, and that no other elements may be present. The term "consisting essentially of" indicates that any elements listed after the phrase are included, and that other elements than those listed may be included provided that those elements do not interfere with or contribute to the activity or action specified in the disclosure for the listed elements.

Unless otherwise specified, "a," "an," "the," and "at least one" are used interchangeably and mean one or more than one.

Conditions that are "suitable" for an event to occur or "suitable" conditions are conditions that do not prevent such events from occurring. Thus, these conditions permit, enhance, facilitate, and/or are conducive to the event.

As used herein, "providing" in the context of, for instance, a composition or a nucleic acid means making the composition or nucleic acid, purchasing the composition or nucleic acid, or otherwise obtaining the compound or nucleic acid.

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments.

Various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7.3, 4, 5, 5.3, and 6. This applies regardless of the breadth of the range.

For any method disclosed herein that includes discrete steps, the steps may be conducted in any feasible order. And, as appropriate, any combination of two or more steps may be conducted simultaneously.

BRIEF DESCRIPTION OF THE FIGURES

The following detailed description of illustrative embodiments of the present disclosure may be best understood when read in conjunction with the following drawings.

FIG. 1 shows a general block diagram of a general illustrative method for one embodiment of producing a library for sequencing according to the present disclosure.

FIG. 3A-3D show schematic drawings of an embodiment of converting a target nucleic acid from symmetric to asymmetric and adding another adapter according to various aspects of the disclosure presented herein. For simplicity, only one target nucleic acid is shown.

FIG. 4A-F show schematic drawings of an embodiment of converting a target nucleic acid from symmetric to asymmetric and adding another adapter according to various aspects of the disclosure presented herein. For simplicity, only one target nucleic acid is shown.

FIGS. 8A-7D show schematic drawings of an embodiment of processing mRNA nucleic acids to DNA and subsequent processing to result in three populations of asymmetric nucleic acids. For simplicity, only one mRNA nucleic acid is shown.

FIG. 12 shows effect of altered nucleotides on extension to add adapter.

FIG. 13 shows altered nucleotides enhance the second extension.

FIG. 28 shows Clustering of single-cell GCC libraries on shared topological domains. Cell line (left) and K-means defined clusters (right).

FIG. 29 shows exemplary nucleotide sequences for a first strand of a transposon, an oligonucleotide containing a second index sequence, P5, i5, P7, i7, ME, A14, and B15 (SEQ ID NO:1-9, respectively).

Figure 2:
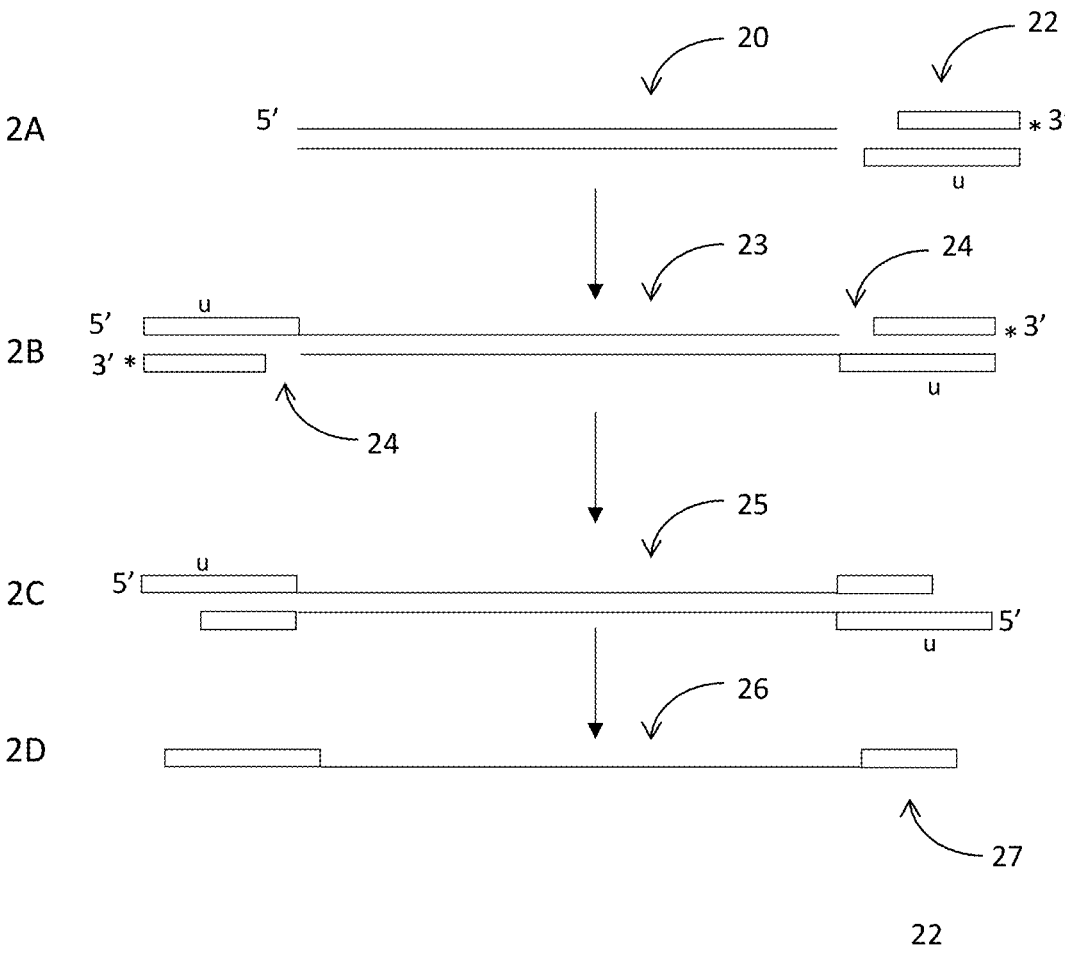
FIG. 2A-2D show schematic drawings of an embodiment of converting a target nucleic acid from symmetric to asymmetric according to various aspects of the disclosure presented herein. For simplicity, only one target nucleic acid is shown.

The schematic drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar to other numbered components.

DETAILED DESCRIPTION

Presented herein are methods, compositions, systems, and kits related to sequencing nucleic acids and/or performing assays. The present disclosure provides methods that significantly increase the number of target nucleic acids present in a sequencing library. FIG. 1 shows a general outline of one illustrative embodiment of the methods. In this illustrative embodiment, the methods include providing target nucleic acids that have been modified to include the same adapter at each end, referred to herein as target nucleic acids with symmetric adapters (FIG. 1, block 10). The source of the target nucleic acids is not intended to be limiting, and the target nucleic acids can originate from DNA or RNA that has been converted to DNA. Likewise, the method used to add adapters to the ends of the target nucleic acids is not intended to be limiting and can include, for instance, transposition, fragmentation followed by ligation, ligation, or extension and ligation. The method further includes modifying one of the symmetric adapters and converting the symmetric modified target nucleic acids to asymmetric modified target nucleic acids (FIG. 1, block 12), target nucleic acids that include a different adapter at each end. The adapters can include index sequences, UMI, universal sequences, and/or sequences derived from a primer. Optionally, the asymmetric target nucleic acids can be amplified (FIG. 1, block 14). The amplification of the asymmetric target nucleic acids can include the addition of other useful sequences to one or both ends, including but not limited to one or more index sequences, UMI sequences, universal sequences, or sequences derived from a primer.

The inventors have made the surprising and unexpected observation that the modified target nucleic acids can be exposed to conditions during the conversion of symmetric to asymmetric target nucleic acids that significantly increase the yield of asymmetric modified target nucleic acids to near the theoretical maximum yield. This can be used with any source of target nucleic acids, and is particularly useful for methods where high efficiency library production is advantageous, including methods using limited input primary nucleic acid. Any sequencing library method can benefit from high-efficiency production including, but not limited to, whole-genome sequencing, targeted sequencing, methylation sequencing, genomic conformation capture (GCC) e.g., HiC, chromatin conformation etc., single cell assays, single cell combinatorial indexing, RNA-seq and ATAC-seq methods, co-assays e.g., DNA and RNA, embodiments where the source is cell free DNA or RNA, and liquid biopsy. High-efficiency conversion assays are also useful in detecting the presence of an analyte, for example increasing sensitivity. Examples of detection or screening assays are, but not limited to, PCR, qPCR, digital PCR, DNA or RNA or antibody or protein detection assays, or in general analyte detection assays. Examples of analytes include, but are not limited to, DNA, RNA, and protein.

Target Nucleic Acids

The target nucleic acids used in the methods, compositions, systems, and kits provided herein are typically derived from primary nucleic acids present in a sample. The primary nucleic acids may originate in double-stranded DNA (dsDNA) form (e.g. genomic DNA fragments, amplification products, and the like) from a sample or may originate in single-stranded form from a sample, as DNA or RNA, and been converted to dsDNA form. By way of example, mRNA molecules may be copied into double-stranded cDNAs during the methods described herein using standard techniques known in the art. The precise sequence of the polynucleotide molecules from a primary nucleic acid sample is generally not material to the disclosure and may be known or unknown.

In one embodiment, the primary nucleic acids include DNA molecules. The primary nucleic acid molecules may represent the entire genetic complement of an organism, e.g., genomic DNA molecules which include both intron and exon sequences, as well as non-coding regulatory sequences such as promoter and enhancer sequences. In one embodiment, particular subsets of genomic DNA can be used, such as, for example, particular chromosomes, DNA associated with open chromatin, DNA associated with closed chromatin, or one or more specific sequences such as a region of a specific gene (e.g., targeted sequencing).

In one embodiment, the primary nucleic acids include RNA molecules. The primary nucleic acid molecules may represent the entire transcriptome or a cell or cells of a sample, e.g., mRNA molecules. The primary nucleic acid molecules may represent non-coding RNA of a cell or cells of a sample, e.g., microRNA or small interfering RNA. In one embodiment, particular subsets of RNA molecules can be used, such as, for example, one or more specific sequences such as a region encoded by a specific gene.

A sample can include nucleic acid molecules obtained from biopsies, tumors, scrapings, swabs, blood, mucus, urine, plasma, semen, hair, laser capture micro-dissections, surgical resections, and other clinical or laboratory obtained samples. In some embodiments, the sample can be an epidemiological, agricultural, forensic or pathogenic sample. In some embodiments, the sample can include cultured cells. In some embodiments, the sample can include nucleic acid molecules obtained from an animal such as a human or mammalian source. In another embodiment, the sample can include nucleic acid molecules obtained from a non-mammalian source such as a plant, bacteria, virus or fungus. In some embodiments, the source of the nucleic acid molecules may be an archived or extinct sample or species.

Further, the methods, compositions, systems, and kits disclosed herein may be useful to amplify a nucleic acid sample having low-quality nucleic acid molecules, such as degraded and/or fragmented genomic DNA from a forensic sample. In one embodiment, forensic samples can include nucleic acids obtained from a crime scene, nucleic acids obtained from a missing persons DNA database, nucleic acids obtained from a laboratory associated with a forensic investigation or include forensic samples obtained by law enforcement agencies, one or more military services or any such personnel. The nucleic acid sample may be a purified sample or a crude lysate containing nucleic acids, for example derived from a buccal swab, paper, fabric or other substrate that may be impregnated with saliva, blood, or other bodily fluids. As such, in some embodiments, the nucleic acid sample may include low amounts of, or fragmented portions of DNA, such as genomic DNA. In some embodiments, target nucleic acids can be present in one or more bodily fluids including but not limited to, blood, sputum, plasma, semen, urine and serum. In some embodiments, target sequences can be obtained from hair, skin, tissue samples, autopsy or remains of a victim. In some embodiments, nucleic acids including one or more target sequences can be obtained from a deceased animal or human. In some embodiments, target sequences can include nucleic acids obtained from non-human DNA such a microbial, plant or entomological DNA. In some embodiments, target sequences are directed to purposes of human identification, such as a forensic sample.

Additional non-limiting examples of sources of biological samples can include whole organisms as well as a sample obtained from a patient. The biological sample can be obtained from any biological fluid or tissue and can be in a variety of forms, including liquid fluid and tissue, solid tissue, and preserved forms such as dried, frozen, and fixed forms. The sample may be of any biological tissue, cells or fluid. Such samples include, but are not limited to, sputum, blood, serum, plasma, blood cells (e.g., white cells), ascitic fluid, urine, saliva, tears, sputum, vaginal fluid (discharge), washings obtained during a medical procedure (e.g., pelvic or other washings obtained during biopsy, endoscopy or surgery), tissue, nipple aspirate, core or fine needle biopsy samples, cell-containing body fluids, peritoneal fluid, and pleural fluid, or cells therefrom, and free floating nucleic acids such as cell-free circulating DNA. Biological samples may also include sections of tissues such as frozen or fixed sections taken for histological purposes or micro-dissected cells or extracellular parts thereof. In some embodiments, the sample can be a blood sample, such as, for example, a whole blood sample. In another example, the sample is an unprocessed dried blood spot (DBS) sample. In yet another example, the sample is a formalin-fixed paraffin-embedded (FFPE) sample. In yet another example, the sample is a saliva sample. In yet another example, the sample is a dried saliva spot (DSS) sample.

Exemplary biological samples from which target nucleic acids can be derived include, for example, those from a eukaryote, for instance a mammal, such as a rodent, mouse, rat, rabbit, guinea pig, ungulate, horse, sheep, pig, goat, cow, cat, dog, primate, human or non-human primate; a plant, such as *Arabidopsis thaliana*, corn, sorghum, oat, wheat, rice, canola, or soybean; an algae, such as *Chlamydomonas reinhardtii*; a nematode such as *Caenorhabditis elegans*; an insect, such as *Drosophila melanogaster*, mosquito, fruit fly, honey bee or spider; a fish, such as zebrafish; a reptile; an amphibian, such as a frog or *Xenopus laevis*; a *Dictyostelium discoideum*; a fungi, such as *Pneumocystis carinii, Takifugu rubripes*, yeast, *Saccharamoyces cerevisiae*, or *Schizosaccharomyces pombe*; or *Plasmodium falciparum*. Target nucleic acids can also be derived from a prokaryote such as a bacterium, *Escherichia coli*, staphylococci or *Mycoplasma pneumoniae*; an archaea; a virus such as Hepatitis C virus or human immunodeficiency virus; or a viroid. Target nucleic acids can be derived from a homogeneous culture or population of organisms described herein or alternatively from a collection of several different organisms, for example, in a community or ecosystem.

In some embodiments, a sample includes tissue that is processed to obtain the desired primary nucleic acids. In some embodiments, cells are used obtain the desired primary nucleic acids. In some embodiments, nuclei are used to obtain the desired primary nucleic acids. The method can further include dissociating cells, and/or isolating nuclei from cells. Methods for isolating cells and nuclei from tissue are available (WO 2019/236599).

In some embodiments, nucleic acids present in tissue, in cells, or in isolated nuclei can be processed depending on the desired read-out. For instance, nucleic acids can be fixed during processing, and useful fixation methods are available (WO 2019/236599). Fixation can be useful to preserve a sample or maintain contiguity of analytes from a sample, a cell, or a nucleus. Fixation methods preserve and stabilize tissue, cell, and nucleus morphology and architecture, inactivates proteolytic enzymes, strengthens samples, cells, and nuclei so they can withstand further processing and staining, and protects against contamination. Examples of methods where fixation can be useful include, but are not limited to, whole genome sequencing of isolated nuclei and chromosome conformation capture methods such as Hi-C. Common methods of fixation include Perfusion, Immersion, Freezing, and Drying (Srinivasan et al., Am J Pathol. 2002 December; 161(6): 1961-1971.doi: 10.1016/S0002-9440(10)64472-0).

In some embodiments such as whole genome sequencing, isolated nuclei can be processed to dissociate nucleosomes from DNA while leaving the nuclei intact, and methods for generating nucleosome-free nuclei are available (WO 2018/018008). In one embodiment, a detergent-based nucleosome method is used (Example 2). In some embodiments such as chromosome conformation capture methods, nucleic acids present in tissue, in cells, or in isolated nuclei can be fragmented, for instance, by restriction endonuclease digestion. Fragmentation is described in greater detail herein. In some embodiments such as chromosome conformation capture methods, nucleic acids present in tissue, in cells, or in isolated nuclei can be exposed to conditions for proximity-based ligation, such as blunt ended ligation, In some embodiments, primary nucleic acids in bulk, e.g., from a plurality of cells, can be used to produce a sequencing library as described herein. In other embodiments, individual cells or nuclei can be used as sources of primary nucleic acids to obtain sequence information from single cells and nuclei. Many different single cell library preparation methods are known in the art. (Hwang et al. Experimental & Molecular Medicine, vol. 50, Article number: 96 (2018), including, but not limited to, Drop-seq, Seq-well, and single cell combinatorial indexing ("sci-") methods. Companies providing single cell products and related technologies include, but are not limited to, 10× genomics, Takara biosciences, BD biosciences, Biorad, 1cellbio, isoplexis, CellSee, nanoselect, Dolomite bio. Sci-seq is a methodological framework that employs split-pool barcoding to uniquely label the nucleic acid contents of large numbers of single cells or nuclei. Typically, the number of nuclei or cells can be at least two. The upper limit is dependent on the practical limitations of equipment (e.g., multi-well plates, number of indexes) used in other steps of the methods as described herein. The number of nuclei or cells that can be used is not intended to be limiting and can number in the billions. For instance, in one embodiment the number of nuclei or cells can be no greater than 100,000,000, no greater than 10,000,000, no greater than 1,000,000,000, no greater than 100,000,000, no greater than 10,000,000, no greater than 1,000,000, no greater than 100,000, no greater than 10,000, no greater than 1,000, no greater than 500, or no greater than 50.

Adapters

A method of the present disclosure can include adding an adapter to both ends of target nucleic acids. Many adapters for use in preparing sequencing libraries are known, and essentially any adapter can be used. For example, an adapter can be single stranded, double stranded, or include a double stranded region and a single stranded region. In one embodiment, the single stranded region of an adapter having both single and double stranded regions can be used as a "sticky end" to aid in joining the adapter to a target nucleic acid having complementary single stranded regions at each end. In one embodiment, an adapter having both single and double stranded regions is also referred to as a forked or mismatched adaptor, the general features of which are known (Gormley et al., U.S. Pat. No. 7,741,463; Bignell et al., U.S. Pat. No. 8,053,192). In one embodiment, an adapter is present as part of a transposome complex. Transposome complexes are described in detail herein.

One or both ends of an adapter used for addition to both ends of target nucleic acids can be modified to alter the interaction of the adapter with other nucleic acids. In one embodiment, one 3' end of an adapter can blocked to reduce interaction of ligation efficiency of that specific end. In one embodiment, the addition of the adapter, for instance a double stranded adapter, to each end of the target nucleic acids results in a gap in one strand of the resulting modified target nucleic acid. In one embodiment, the gap is at least one nucleotide. In one embodiment, the gap is located between the 3' end of the target nucleic acid and the 5' end of the adapter attached to the target nucleic acid.

An adapter can include one or more index sequences, one or more UMI, one or more universal sequences, one or more DNA lesions, or a combination thereof. As described in greater detail herein, the presence of an index sequence in an adapter can aid in sci-based applications, sample indexing, or single cell identification.

Nucleotides of a DNA lesion have a structure that, when used by a DNA polymerase as a template during DNA synthesis, cause certain DNA polymerases to have reduced activity and stall or terminate DNA synthesis at the DNA lesion. This type of DNA polymerase is referred to herein as a "lesion-intolerant polymerase." Examples of nucleotides that can be used as a DNA lesion are known to the skilled person and include, but are not limited to, an abasic site, a modified base, a mismatch, a single-stranded break, or cross-linked nucleotides. Examples of modified bases include, but are not limited to, a methylated base (e.g., N3-methyladenine, N7-06-methylguanine, N3-methyl cytosine, 04 methyl thymine), 06-alkylguanine, 04-alkyl thymine, hypoxanthine, xanthine, and uracil. Modified bases can also include oxidized bases including, but not limited to, Fapy TA, 8-oxo-G, and thimine glycol. An example of cross-linked nucleotides include, but are not limited to, a thymine dimer.

Lesion-intolerant polymerases are known to the skilled person (Heyn et al., Nucleic Acids Res. 2010 September; 38(16): e161; Sikorsky et al., Biochem Biophys Res Commun. 2007 Apr. 6; 355(2): 431-437; and Gruz et al., Nucleic Acids Res. 2003 Jul. 15; 31(14): 4024-4030). Examples of useful lesion-intolerant polymerases are shown in Table 1.

TABLE 1

| DNA lesion | DNA polymerases | |
| | Has reduced activity using lesion as template (lesion-intolerant) | Extends over lesion (lesion-tolerant) |
| --- | --- | --- |
| dU | Phusion ™, Q5 ®, Kapa HiFi ™ | PhusionU ™, Q5U ®, KapaU ™, Taq, Dpo4 |
| 8-oxo-G | Phusion ™, Q5 ®, Kapa HiFi ™ | Taq, Dpo4 |
| Abasic site | Phusion ™, Q5 ®, Kapa HiFi ™ | Dpo4 |
| Deoxylnosine | Pfu, Phusion ™, Q5 ®, Kapa HiFi ™ | Taq, Dpo4 |

A method of the present disclosure can include a step of using a lesion-intolerant polymerase and can also include another step of using a DNA polymerase that does not have reduced activity using a DNA lesion a template. A polymerase that does not have reduced activity when using a DNA lesion as a template is referred to herein as a "lesion-tolerant polymerase." Lesion-tolerant polymerases are known to the skilled person and include, but are not limited to, those described in Table 1. The use of a lesion-tolerant polymerase can occur during the conversion of a symmetric modified target nucleic acid to an asymmetric modified target nucleic acid, and typically results in loss of the DNA lesion(s) in the resulting amplicon. The use of a lesion-tolerant polymerase during conversion is described herein.

A DNA lesion can include one or more nucleotides having the activity of reducing DNA polymerase activity. For instance, the number of nucleotides making up a DNA lesion can be at least 1, at least 2, at least 3, at least 4, or at least 5. In one embodiment, the number of nucleotides making up a DNA lesion can be no greater than 5, no greater than 4, no greater than 3, or no greater than 2. In one embodiment, a DNA lesion is 2, 3, or 4 uracil nucleotides. If a DNA lesion includes more than one nucleotide, the nucleotides of the DNA lesion are typically consecutive.

A DNA lesion is typically present in one strand of an adapter that is present at each end of a target nucleic acid. In one embodiment, when the adapter includes a DNA lesion and a gap is present in one strand where the adapter is joined to the target nucleic acid, the DNA lesion and the gap are located on different strands.

An adapter can also include a capture agent. As used herein, the term "capture agent" refers to a material, chemical, molecule, or moiety thereof that is capable of attaching, retaining, or binding to a nucleic acid (e.g., a strand of an adapter). Exemplary capture agents include, without limitation, a member of a receptor-ligand binding pair (e.g., avidin, streptavidin, biotin, lectin, carbohydrate, nucleic acid binding protein, epitope, antibody, etc.) capable of binding to the member of the receptor-ligand pair, or a chemical reagent capable of forming a covalent bond with a linking moiety. In one embodiment, a capture agent is biotin. A capture agent can be attached to a strand of an adapter and is attached to the end of an adapter so it does not interfere with the attachment of an adapter to a target nucleic acid. For instance, a 5' end of an adapter can include a capture agent, or a 3' end of a n adapter can include a capture agent. In one embodiment, a capture agent is attached to the 5' end of a strand of a transposon or to the 3' end of the other strand of transposon. A capture agent is useful in attaching an adapter to a solid surface, such as a bead or well.

An adapter can also include a cleavable linker between a capture agent and the adapter. An example of a cleavable linker includes, but is not limited to, a disulfide bond, which may be cleaved with, for example, dithiothreitol to release the capture agent. Capture agents with cleavable linkers, including biotin-labelled nucleotides having cleavable linkers are commercially available.

Producing Target Nucleic Acids with Symmetric Adapters

The methods, compositions, systems, and kits provided herein can optionally include processing primary nucleic acids to obtain modified target nucleic acids having lengths that are suitable for sequencing and symmetric by virtue of having the same adapter at each end. The sample of primary nucleic acids can include high molecular weight material such as genomic DNA or low molecular weight material such as nucleic acid molecules obtained from liquid biopsy or by conversion of RNA to DNA. Various methods for processing nucleic acids present in bulk, present in isolated nuclei, or present in isolated cells into nucleic acid fragments are known. In one embodiment a transposome complex is used and results in the addition of an adapter. In another embodiment DNA is fragmented, for instance, by enzymatic or mechanical methods, and adapters are then added to the ends of the fragments. In another embodiment, RNA molecules, such as mRNA, are converted to cDNA and adapters are added to the ends.

The transposome complex is a transposase bound to transposon sequences, typically including a transposase recognition site, and can insert the transposase recognition site into a target nucleic acid within a DNA molecule in a process sometimes termed "tagmentation." Tagmentation combines into a single step fragmentation and ligation to add universal adapters (Gunderson et al., WO 2016/130704). The skilled person will recognize that tagmentation is typically used to produce nucleic acid fragments that include different adapters at each end as the production of asymmetric target nucleic acids is easily and efficiently accomplished with transposition and are ready for sequencing. Tagmentation methods for producing asymmetric target nucleic acids are useful but are inefficient and typically reduce the theoretical yield to 50%. In contrast, as used in methods of the present disclosure, tagmentation produces nucleic acid fragments that include the same nucleotide sequences at each end and can increase the theoretical yield to nearly 100%.

In some embodiments, one strand of the transposon may be transferred onto, e.g., covalently attached, to the 5' end of the target nucleic acid during the insertion event. Such a strand is referred to as a "transferred strand." A transposon sequence can include an adapter, which can include one or more index sequences, one or more UMI, one or more universal sequences, one or more DNA lesions, or a combination thereof. In one embodiment, a universal sequence is a transposase recognition site. Examples of transposase recognition sites include but are not limited to a mosaic element (ME). In one embodiment, the adapter, e.g., one or more index sequences, one or more UMI, one or more universal sequences, one or more DNA lesions, or a combination thereof, are present on the transferred strand. In some embodiments, one strand of the transposon may not transferred, e.g., not covalently attached, to the 3' end of the target nucleic acid during the insertion event. Such a strand is referred to as a "non-transferred strand." The presence of the non-transferred strand can result in the generation during the transposition reaction of a duplication of nucleotides of the target nucleic acid and cause a gap between the 5' of adapter sequence and the 3' end of the target nucleic acid. The size of the gap can vary and is typically dependent upon the transposon system used. For instance, the gap introduced by a Tn5-based system is typically 9 bases.

Some embodiments can include the use of a hyperactive Tn5 transposase and a Tn5-type transposase recognition site (Goryshin and Reznikoff, *J. Biol. Chem.*, 273:7367 (1998)), or MuA transposase and a Mu transposase recognition site comprising R1 and R2 end sequences (Mizuuchi, K., *Cell*, 35: 785, 1983; Savilahti, H, et al., *EMBO J.*, 14: 4893, 1995). Tn5 Mosaic End (ME) sequences, a transposase recognition site, can also be used as optimized by a skilled artisan.

More examples of transposition systems that can be used with certain embodiments of the methods, composition, systems, and kits provided herein include *Staphylococcus aureus* Tn552 (Colegio et al., *J. Bacteriol.*, 183: 2384-8, 2001; Kirby C et al., *Mol. Microbiol.*, 43: 173-86, 2002), Ty1 (Devine & Boeke, *Nucleic Acids Res.*, 22: 3765-72, 1994 and International Publication WO 95/23875), Transposon Tn7 (Craig, N L, *Science*. 271: 1512, 1996; Craig, N L, *Review in: Curr Top Microbiol Immunol.*, 204:27-48, 1996), Tn/O and IS10 (Kleckner N, et al., *Curr Top Micro-*

*biol Immunol.*, 204:49-82, 1996), Mariner transposase (Lampe D J, et al., *EMBO J.*, 15: 5470-9, 1996), Tc1 (Plasterk R H, *Curr. Topics Microbiol. Immunol.*, 204: 125-43, 1996), P Element (Gloor, G B, *Methods Mol. Biol.*, 260: 97-114, 2004), Tn3 (Ichikawa & Ohtsubo, *J Biol. Chem.* 265:18829-32, 1990), bacterial insertion sequences (Ohtsubo & Sekine, *Curr. Top. Microbiol. Immunol.* 204: 1-26, 1996), retroviruses (Brown, et al., *Proc Natl Acad Sci USA*, 86:2525-9, 1989), and retrotransposon of yeast (Boeke & Corces, *Annu Rev Microbiol.* 43:403-34, 1989). More examples include IS5, Tn10, Tn903, IS911, and engineered versions of transposase family enzymes (Zhang et al., (2009) *PLoS Genet.* 5:e1000689. Epub 2009 Oct. 16; Wilson C. et al (2007) *J. Microbiol. Methods* 71:332-5).

Other examples of integrases that may be used with the methods and compositions provided herein include retroviral integrases and integrase recognition sequences for such retroviral integrases, such as integrases from HIV-1, HIV-2, SIV, PFV-1, RSV.

Transposon sequences useful with the methods and compositions described herein are provided in U.S. Patent Application Pub. No. 2012/0208705, U.S. Patent Application Pub. No. 2012/0208724 and Int. Patent Application Pub. No. WO 2012/061832.

Various transposome complex configurations are known in the art. In one embodiment, a transposome complex includes a dimeric transposase having two subunits, and two non-contiguous transposon sequences. Examples of such transposomes are known in the art (see, for instance, U.S. Patent Application Pub. No. 2010/0120098). In some embodiments, a transposome complex includes a transposon sequence nucleic acid that binds two transposase subunits to form a "looped complex" or a "looped transposome." In one example, a transposome includes a dimeric transposase and a transposon sequence. Looped complexes can ensure that transposons are inserted into target DNA while maintaining ordering information of the original target DNA and without fragmenting the target DNA. As will be appreciated, looped structures may insert the desired adapter sequences into a target nucleic acid, while maintaining physical connectivity of the target nucleic acid. In some embodiments, the transposon sequence of a looped transposome complex can include a fragmentation site such that the transposon sequence can be fragmented to create a transposome complex containing two transposon sequences. Such transposome complexes are useful to ensuring that neighboring target DNA fragments, in which the transposons insert, receive barcode combinations that can be unambiguously assembled at a later stage of the assay.

Fragmentation sites can be introduced into target nucleic acids by using a transposome complex. In one embodiment, after nucleic acids are fragmented the transposase remains attached to the nucleic acid fragments, such that nucleic acid fragments derived from the same genomic DNA molecule remain physically linked (Adey et al., 2014, Genome Res., 24:2041-2049). Cleavage may be by biochemical, chemical or other means. In some embodiments, a fragmentation site can include a nucleotide or nucleotide sequence that may be fragmented by various means. Examples of fragmentation sites include, but are not limited to, a restriction endonuclease site, at least one ribonucleotide cleavable with an RNAse, nucleotide analogues cleavable in the presence of a certain chemical agent, a diol linkage cleavable by treatment with periodate, a disulfide group cleavable with a chemical reducing agent, a cleavable moiety that may be subject to photochemical cleavage, and a peptide cleavable by a peptidase enzyme or other suitable means (see, for instance, U.S. Patent Application Pub. No. 2012/0208705, U.S. Patent Application Pub. No. 2012/0208724 and WO 2012/061832).

In those embodiments where the primary nucleic acid is DNA, the result of transposition is a library of modified target nucleic acids, where each fragment includes the symmetric adapter at each end. In contrast, in those embodiments where the primary nucleic acid is RNA, the result of transposition is up to three distinct types of modified target nucleic acids. The first population includes a library of modified target nucleic acids, where each fragment includes the symmetric adapter at each end. The second and third populations each include the adapter introduced by the transposon at one end and at the other end, i.e., the end corresponding to either the 3' or the 5' end of the RNA, the adapter added by an alternative method such as template-switch primer, random primer, or poly-T.

As an alternative to transposition, target nucleic acids can be obtained by fragmentation. Fragmentation of primary nucleic acids from a sample can be accomplished in a non-ordered fashion by enzymatic, chemical, or mechanical methods, and adapters are then added to the ends of the fragments. Examples of enzymatic fragmentation include CRISPR and Talen-like enzymes, and enzymes that unwind DNA (e.g. Helicases) that can make single stranded regions to which DNA fragments can hybridize and initiate extension or amplification. For example, helicase-based amplification can be used (Vincent et al., 2004, EMBO Rep., 5(8):795-800). In one embodiment, the extension or amplification is initiated with a random primer. Examples of mechanical fragmentation include nebulization or sonication.

Fragmentation of primary nucleic acids by mechanical means results in fragments with a heterogeneous mix of blunt and 3'- and 5'-overhanging ends. It is therefore desirable to repair the fragment ends using methods known in the art to generate ends that are optimal for addition of adapters, for example, into blunt sites. In a particular embodiment, the fragment ends of the population of nucleic acids are blunt ended. More particularly, the fragment ends are blunt ended and phosphorylated. The phosphate moiety can be introduced via enzymatic treatment, for example, using polynucleotide kinase.

In one embodiment, the fragmented nucleic acids are prepared with overhanging nucleotides. For example, single overhanging nucleotides can be added by the activity of certain types of DNA polymerase such as Taq polymerase or Klenow exo minus polymerase which has a non-template-dependent terminal transferase activity that adds a single deoxynucleotide, for example, the nucleotide 'A' to the 3' ends of a DNA molecule. Such enzymes can be used to add a single nucleotide 'A' to the blunt ended 3' terminus of each strand of double-stranded nucleic acid fragments. Thus, an 'A' could be added to the 3' terminus of each end repaired strand of the double-stranded target fragments by reaction with Taq or Klenow exo minus polymerase, while the adapter could be a T-construct with a compatible 'T' overhang present on the 3' terminus of each region of double stranded nucleic acid of the universal adapter. In one example, terminal deoxynucleotidyl transferase (TdT) can be used to add multiple 'T' nucleotides (Swift Biosciences, Ann Arbor, MI). This type of end modification also prevents self-ligation of both vector and target such that there is a bias towards formation of the target nucleic acids having the same adapter at each end.

The adapter can be added to the ends of fragmented DNA or asymmetric DNA target nucleic acids by various methods, including, for instance, ligation of a double stranded adapter to the ends of fragments or extension of an annealed primer. Ligation of a double stranded adapter to the ends of fragments can be blunt ended or aided by use of an overhang present at the ends of the fragments. An adapter can also be added using a single-stranded or double-stranded adapter including ligation or polymerization (e.g., TdT labeling). In one embodiment, the adapter is configured to result in a gap in one strand of the resulting modified target nucleic acid. In one embodiment, the gap is at least one nucleotide. In one embodiment, the gap is located between the 3' end of the target nucleic acid and the 5' end of the adapter attached to the target nucleic acid.

In those embodiments where the primary nucleic acid is RNA, producing target nucleic acids with symmetric adapters typically includes the conversion of RNA into DNA with the optional introduction of an adapter at one or both ends. Various methods can be used to add an adapter to the 3' side of the mRNA. For example, an adapter can be added with routine methods used to produce cDNA. A primer with a poly-T sequence at the 3' end and an adapter upstream of the poly-T sequence can be annealed to mRNA molecules and extended using a reverse transcriptase. This results in a one-step conversion of mRNA to DNA and optionally the addition of the adapter to the 3' end. In one embodiment, the primer can also include one or more index sequences, one or more UMI, one or more universal sequence, or a combination thereof. In one embodiment, a random primer is used.

A non-coding RNA can also be converted into DNA and optionally modified to include an adapter using various methods. For example, an adapter can be added using a first primer that includes a random sequence and a template-switch primer, where either primer can include an adapter. A reverse transcriptase having a terminal transferase activity to result in addition of non-template nucleotides to the 3' end of the synthesized strand can be used, and the template-switch primer includes nucleotides that anneal with the non-template nucleotides added by the reverse transcriptase. An example of a useful reverse transcriptase enzyme is a Moloney murine leukemia virus reverse transcriptase. In a particular embodiment, the SMARTer™ reagent available from Takara Bio USA, Inc. (Cat. No. 634926) is used for the use of template-switching to add an index to non-coding RNA, and mRNA if desired. Optionally, a template-switch primer can be used with mRNA in conjunction with a primer with a poly-T sequence to result in adding a universal sequence to both ends of a DNA target nucleic acid produced from RNA. In one embodiment, the same adapter is added to both ends.

A population of target nucleic acids can have an average strand length that is desired or appropriate for a particular application of the methods or compositions set forth herein. For example, the average strand length for the members that are used in one or more steps of a method set forth herein or that are present in a particular composition, system, or kit can be less than about 100,000 nucleotides, 50,000 nucleotides, 10,000 nucleotides, 5,000 nucleotides, 1,000 nucleotides, 500 nucleotides, 100 nucleotides, or 50 nucleotides. Alternatively, or additionally, the average strand length can be greater than about 10 nucleotides, 50 nucleotides, 100 nucleotides, 500 nucleotides, 1,000 nucleotides, 5,000 nucleotides, 10,000 nucleotides, 50,000 nucleotides, or 100,000 nucleotides. The average strand length for population of target nucleic acids can be in a range between a maximum and minimum value set forth above. It will be understood that amplicons generated at an amplification site (or otherwise made or used herein) can have an average strand length that is in a range between an upper and lower limit selected from those exemplified above.

In some embodiments, the target nucleic acids are sized relative to the area of amplification sites, for example, to facilitate exclusion amplification. For example, the area for each of the sites of an array can be greater than the diameter of the excluded volume of the target nucleic acids in order to achieve exclusion amplification. Taking, for example, embodiments that use an array of features on a surface, the area for each of the features can be greater than the diameter of the excluded volume of the target nucleic acids that are transported to the amplification sites. The excluded volume for a target nucleic acid and its diameter can be determined, for example, from the length of the target nucleic acid. Methods for determining the excluded volume of nucleic acids and the diameter of the excluded volume are described, for example, in U.S. Pat. No. 7,785,790; Rybenkov et al., Proc. Natl. Acad. Sci. U.S.A. 90: 5307-5311 (1993); Zimmerman et al., J. Mol. Biol. 222:599-620 (1991); or Sobel et al., Biopolymers 31:1559-1564 (1991).

Producing primary nucleic acids fragments by tagmentation or fragmentation and processing of the target nuclei acids can be followed by a clean-up process to enhance the purity of the molecules. Any suitable clean-up process may be used, such as electrophoresis, size exclusion chromatography, or the like. In some embodiments, solid phase reversible immobilization paramagnetic beads may be employed to separate the desired DNA molecules from, for instance, unincorporated primers, and to select nucleic acids based on size. Solid phase reversible immobilization paramagnetic beads are commercially available from Beckman Coulter (Agencourt AMPure XP), Thermofisher (MagJet), Omega Biotek (Mag-Bind), Promega Beads (Promega), and Kapa Biosystems (Kapa Pure Beads).

Converting Target Nucleic Acids from Symmetric to Asymmetric

The methods, compositions, systems, and kits provided herein include converting symmetric target nucleic acids to target nucleic acids with asymmetric adapters. As discussed herein, in some embodiments, the addition of the adapter to each end of the target nucleic acids results in a gap in each strand of the resulting modified target nucleic acid. In one embodiment, the gap is located between the 3' end of the target nucleic acid and the 5' end of the adapter attached to each end of the target nucleic acid. In one embodiment, the gap can be filled in with nucleotides and ligated using the 3' end of the target nucleic acid as a primer. For example, in some embodiments of using a transposome complex the 9 bp target sequence duplication created by a Tn5-based transposon insertion is extended. In one embodiment, the extension uses a strand-displacing polymerase to result in the displacement of the upstream sequences. In one embodiment, the target sequence duplication created by transposition is not extended. In one embodiment, ligation is used. When extension is used to fill a gap, a lesion-intolerant polymerase or a lesion-tolerant polymerase can be used.

In one embodiment, when the adapter includes a DNA lesion and a gap is present in one strand where the adapter is joined to the target nucleic acid, the DNA lesion and the gap are located on different strands. The polymerase used to fill in the gap by extension will use the DNA lesion in the template strand, and if the polymerase is lesion-intolerant then extension will be terminated. Consequently, when this configuration is present, the use of a lesion-intolerant polymerase results in retention of only a portion of the adapter sequences of the adapter downstream of the gap. This in turn results in the modification of one adapter of the target nucleic acids and production of asymmetric target nucleic acids. The skilled person will recognize that the asymmetric target nucleic acids can be used in a sequencing reaction including a paired-end sequencing reaction; however, the methods of the present disclosure provide further advantages that will be described herein.

An example of structures that can occur in one embodiment of producing symmetric target nucleic acids and then modifying one adapter to result in asymmetric target nucleic acids is shown in FIG. 2. An illustrative target nucleic acid 20 is shown with a symmetric adapter 22 is shown in FIG. 2A. In this illustrative embodiment the symmetric adapter includes a DNA lesion (shown by the U). The 3' end of one strand is blocked (shown by the *), and the 3' end of the other strand includes an overhang. The adapter can include one of more universal sequences, one or more index sequences, one or more UMI, or a combination thereof. After attachment of the adapter to each end of the target nucleic acid 20, the modified target nucleic acid 23 includes a gap 24 at the 3' end of the original target nucleic acid 20. Extension of the modified target nucleic acid 23 with a lesion-intolerant polymerase begins at the 3' end of the gap 24 and stops at the DNA lesion U, and the resulting modified target nucleic acid 25 is shown in FIG. 2C. Denaturation of the modified target nucleic acid 25 yields an asymmetric target nucleic acid 26, where the nucleic acid includes the strand of the symmetric adapter 22 with the DNA lesion at one end and at the other end a portion 27 of the symmetric adapter sequences located between the gap and the DNA lesion.

Following the modification of symmetric target nucleic acids to target nucleic acids with asymmetric adapters, the asymmetric target nucleic acids can be further modified. For instance, sequences can be added by specifically targeting one of the ends, e.g., adding nucleotides to the first adapter added to the target nucleic acids or adding nucleotides to the adapter that was modified to result in the asymmetric target nucleic acids. In one embodiment, the modification can include using a primer in an extension reaction to add a second adapter to the adapter that was modified to result in the asymmetric target nucleic acids (e.g., the modification of adapter 22 to 27 as illustrated in FIG. 2D).

The primer used in the modification can include at least two domains. The first domain is present at the 3' end of the primer and includes a sequence that anneals to a portion of the adapter that was modified to result in the asymmetric target nucleic acids. The first domain is also referred to herein as an annealing domain. The skilled person will recognize that the primer will be useful in the method if the first domain has a length sufficient for specific annealing. The skilled person will also recognize that the primer will be useful in the method if the nucleotides to which is it anneals include the 3' nucleotide of the asymmetric adapter, thereby making that 3' nucleotide a suitable initiation site for extension using the primer's second domain as the template. The 3' end of asymmetric target nucleic acids can also be modified using ligation.

In one embodiment, one or more nucleotides of the annealing domain are altered nucleotides. An altered nucleotide is a nucleotide that denatures at a higher melting temperature than the corresponding native DNA nucleotide, e.g., the nucleotide hydrogen-bonds with a complementary native nucleotide A, T, G, or C with greater strength than the corresponding native DNA nucleotide. Examples of altered nucleotides include, but are not limited to, locked nucleic acids (LNA®), bridged nucleic acids (BNA), pseudo-complementary bases, peptide nucleic acids (PNA), 2,6- diaminopurine, 5'methyldC, SuperT, RNA nucleotides, or essentially any nucleotide or base known in the art that increases the melting temperature The number of altered nucleotides in the first domain of the primer can be at least 1, at least 2, at least 3, at least 4, or at least 5. In some embodiments, a combination of natural and altered nucleotide is used. In one embodiment, the altered nucleotides are at least 5, at least 10, or at least 15 nucleotides away from a polymerase initiation site. In one embodiment, concentrations of the primer useful for extension can be determined by routine titration.

In one embodiment, the 3' end of the primer or adapter is blocked to prevent incorporation of nucleotides on the 3' end of the primer by a DNA polymerase. Examples of ways to block the 3' end of the primer include, but are not limited to, removal of the 3'-OH group, or by the presence of a nucleotide such as a dideoxynucleotide (ddNTP) at the 3' end of the primer, reverse base, additional bases without their complement, or mismatched bases.

The second domain of the primer has a nucleotide sequence that includes an adapter. The adapter can include one or more index sequences, one or more UMI, one or more universal sequences, or a combination thereof. Typically, any index sequence, UMI, and universal sequence present in the adapter is unique compared to any index sequence, UMI, and universal sequence already present in the asymmetric target nucleic acid. In some embodiments, a universal sequence if present can be located at the 5' end of the primer, and any optional sequences such as an index or a UMI can be present between the first domain and the universal sequence.

The primer is used to extend or ligate the 3' end of single stranded asymmetric target nucleic acids having the symmetric adapter at one end and the asymmetric adapter at the other end.

In some embodiments, the effectiveness of the extension is dependent on the annealing temperature, and the skilled person can easily identify a useful annealing temperature using a temperature titration and amplification, such as qPCR. In one embodiment, a lesion-intolerant DNA polymerase is used for the extension. The result of the extension is an asymmetric target nucleic acid that retains the symmetric adapter at one end, and the asymmetric adapter at the other end has been modified to include another adapter.

Native nucleotides A, T, G, and C can be used in the extension. In some embodiments, non-native nucleotides are used. For example, a methylated cytosine can be used. Methylated cytosine is advantageous in methylation sequencing applications (WO 2017/106481) as the adapter primer is typically not converted during a cytosine to uracil conversion.

In one embodiment, the extension reaction is repeated. The inventors found that the use of multiple extension cycles with a two-domain primer having at least one altered nucleotide resulted in a surprising and unexpected increase the in the yield of asymmetric modified target nucleic acids to near the theoretical maximum yield. In one embodiment, the number of extensions can be at least 1, at least 3, at least 5, at least 7, at least 9, or at least 10. In one embodiment, the number of extensions can be no greater than 15, no greater than 13, or no greater than 11. In one embodiment, the number of extensions is 10.

Another example of structures that can occur in one embodiment of producing symmetric target nucleic acids by tagmentation and then modifying one adapter to result in asymmetric target nucleic acids is shown in FIG. 3. An illustrative modified target nucleic acid 33 is shown in FIG.

3A with target nucleic acid 30 and symmetric adapters 32. The adapter can include one or more universal sequences, one or more index sequences, one or more UMI, or a combination thereof. In this illustrative embodiment the symmetric adapters 32 include a DNA lesion (shown by the U), a gap 34, and a universal sequence such as a transposase recognition domain 35. Extension of the modified target nucleic acid 33 with a lesion-intolerant polymerase begins at the 3' end of the gap 34 and stops at the DNA lesion U, and the resulting asymmetric target nucleic acid 36 after denaturation is shown in FIG. 3B. The asymmetric target nucleic acid 36 includes the strand of the symmetric adapter 32 with the DNA lesion at one end. At the other end the asymmetric target nucleic acid 36 includes the asymmetric adapter 37, e.g., a portion of the symmetric adapter sequences that were located between the gap and the DNA lesion. FIG. 3C also shows an illustrative embodiment of further modifying the asymmetric target nucleic acid 36 to include another adapter. A two-domain primer 38 includes one domain 39 that anneals to the asymmetric adapter 37 and a second domain that includes a different adapter 40. In this illustrative embodiment, a block (*) is included to reduce extension initiated at the 3' end of the primer 38. Extension, shown by the dotted line in FIG. 3C, optionally with a lesion-intolerant polymerase, begins at the 3' end of the asymmetric target nucleic acid 36, adds the different adapter 40, and results in the asymmetric target nucleic acid 41 as shown in FIG. 3D.

Another example of structures that can occur in one embodiment of producing symmetric target nucleic acids by tagmentation and then modifying one adapter to result in asymmetric target nucleic acids is shown in FIG. 4. An illustrative transposome complex 41 of two transposases and transposons include adapters 42 (FIG. 4A). Each adapter includes a primer (P5), an index (i5), a universal anchor sequence (A14), a DNA lesion uracil (U), a transposase recognition sequence (ME), and the complement of the transposase recognition sequence (ME'). The adapters also include an optional capture agent (B) and optional cleavable linker (CL) attached to the 5' end of one strand, and an optional blocking dideoxynucleotide (ddC) attached to the 3' end of the other strand. In some embodiments the arrangement of capture agent-cleavable linker and blocking group is switched. FIG. 4B shows the tagged and fragmented nucleic acid, still complexed to the transposase. For simplicity, the depiction of the dimer is shown in FIG. 4A, but not in FIG. 4B. FIG. 4C depicts the structure after removal of transposase and after gap filling with a DNA lesion intolerant polymerase. FIG. 4D depicts the top strand of FIG. 4C with a two-domain primer 43 hybridized thereto. The two-domain primer 43 includes one domain ME that anneals to the complementary ME' and a second domain that includes different adapter sequences B15, i7, and P7. FIG. 4E depicts the result of extension of the top strand based on the two-domain primer sequence. FIG. 4F depicts the tagged library fragment after primer removal. Extension, shown by the dotted line in FIG. 4D, begins at the 3' end of the ME', adds the different adapter 43, and results in the asymmetric target nucleic acid as shown in FIG. 4F.

The library of asymmetric target nucleic acids can be exposed to conditions to remove the DNA lesion, and optionally add one or more further adapters to one or both ends of the asymmetric target nucleic acids, and as a result further modify one or both ends with one or more universal sequences, one or more index sequences, one or more UMI sequences, or the combination thereof. In one embodiment, the conditions to remove the DNA lesion include extension with a lesion-tolerant DNA polymerase. Examples of suitable lesion-tolerant DNA polymerases are shown in Table 1. A lesion-tolerant DNA polymerase can be used in any type of extension reaction that reads through the DNA lesion, and the resulting synthesized strand no longer includes the DNA lesion. In one embodiment, the conditions to remove the DNA lesion include a repair system. DNA repair systems include enzymes and mechanisms to fix or repair a DNA lesion and include, but are not limited to, excision repair systems and DNA repair systems. DNA repair systems are known in the art (Chaudhuri et al., Nature Reviews Molecular Cell Biology, 2017, 18:610-621). After use of a DNA repair system the library of asymmetric target nucleic acids is exposed to conditions that include an extension reaction.

In one embodiment, the extension is by a method that substantially increases the number of asymmetric target nucleic acids. In one embodiment, the method can be an amplification, including but not limited to polymerase chain reaction (PCR) and rolling circle amplification (RCA).

Figure 4A:
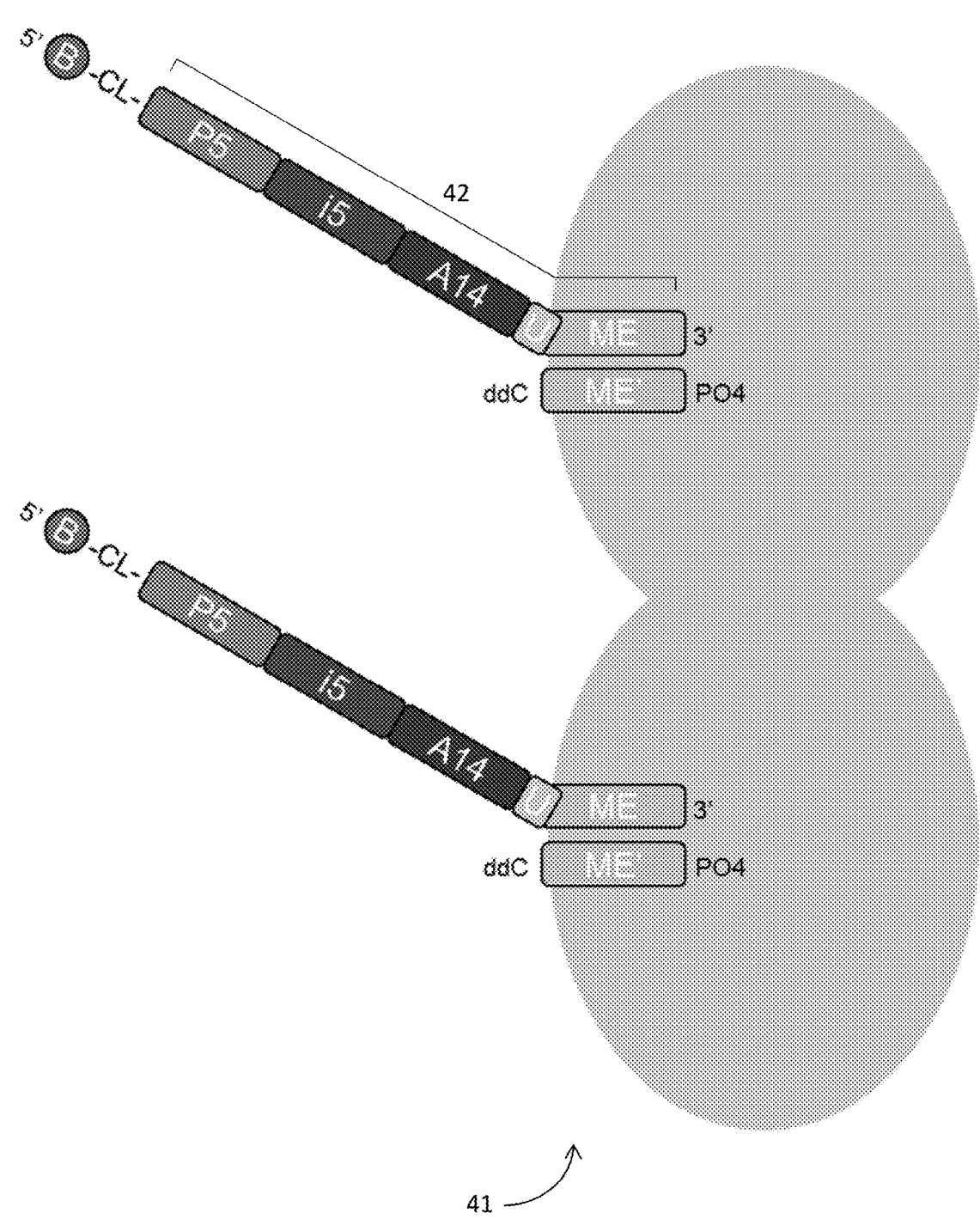
Figure 4B:
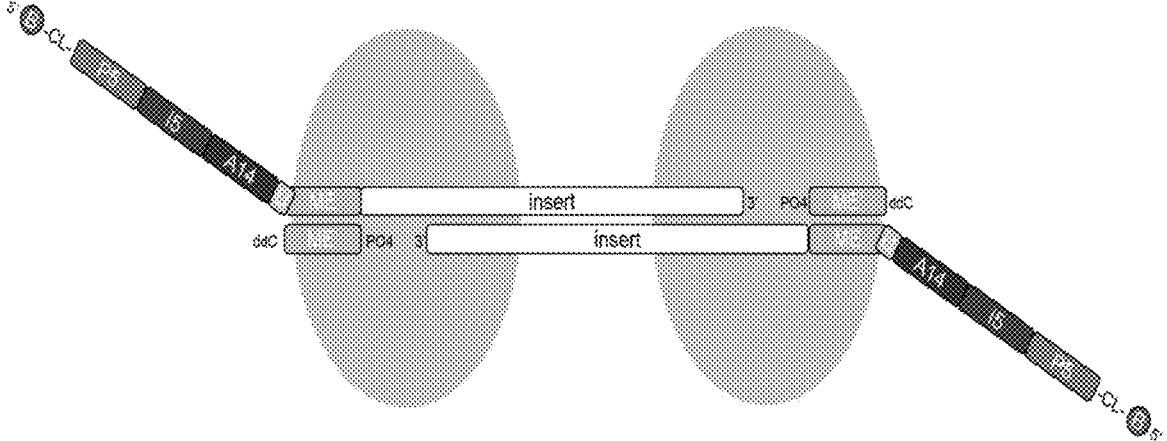
Figure 4C:
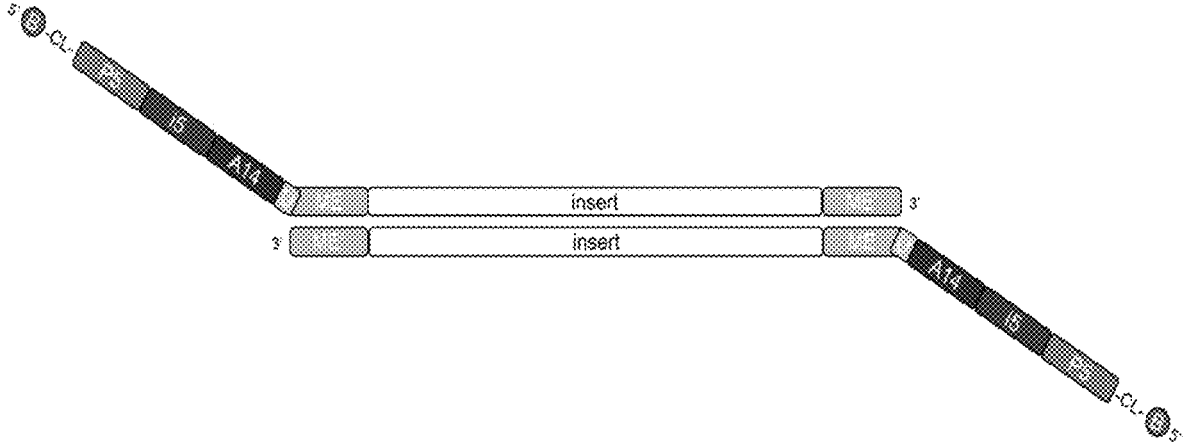
Figure 4D:
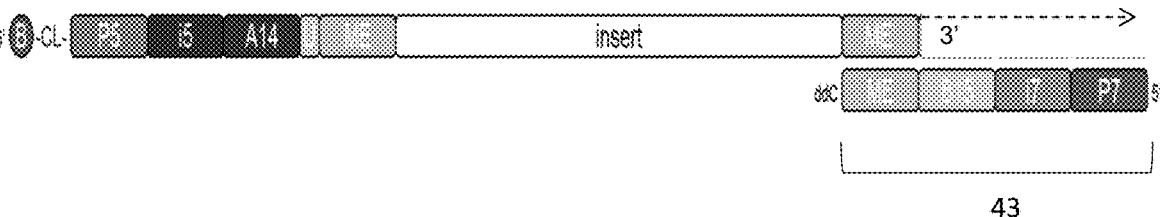
Figure 4E:
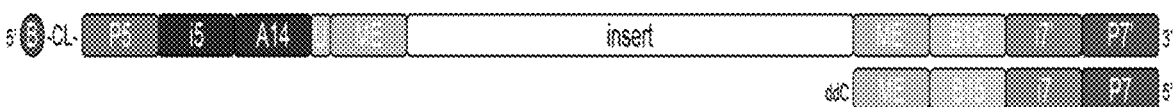
Figure 4F:
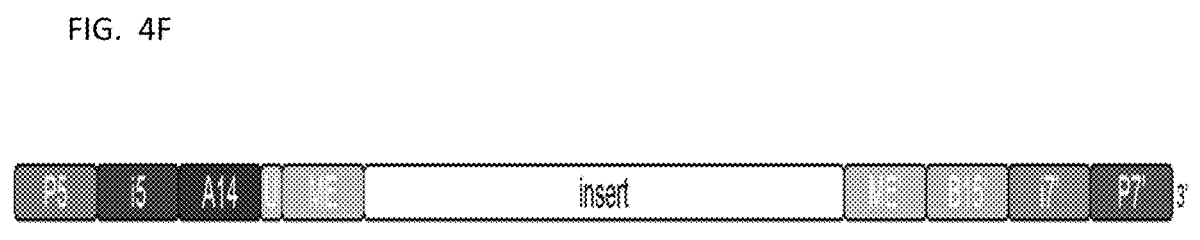

In one embodiment, the method includes the use of transposome complexes bound to a surface, such as the surface of a bead or a well. Typically, in such embodiments one of the strands of the transposon includes a capture agent, such as biotin. The use of a capture agent permits methods that advantageously reduce the steps to produce asymmetric target nucleic acids. For instance, the capture agent and optional cleavable linker can be attached to the 5' end of one strand (e.g., the strand of adapter 42 in FIG. 4 that includes primer P5, index i5, universal anchor sequence A14, DNA lesion uracil U, and transposase recognition sequence ME). After tagmentation using surface-bound transposome complexes, a DNA lesion intolerant polymerase, dNTPs, and a two-domain primer, such as the two-domain primer 43 in FIG. 4D, can be added. Upon exposure to denaturing conditions, e.g., heat, the complement of the transposase recognition sequence ME' is removed. For instance, the ME' shown in FIG. 4B is no longer hybridized. The polymerase extends the 3' copy of the target nucleic acid using the ME as a template, resulting in ME' attached to the 3' end of the target nucleic acid, and stops at the DNA lesion. Following another denaturation step, the two-domain primer 43 is annealed to the ME' attached to the 3' end of the target nucleic acid. Extension is initiated at the ME' using the two-domain primer as template to result in asymmetric target nucleic acids. The asymmetric target nucleic acids can then be removed from the solid surface.

In another embodiment of using transposome complexes bound to a surface, such as the surface of a bead or a well, the capture agent and optional cleavable linker can be attached to the 3' end of the other strand (e.g., the strand of adapter 42 in FIG. 4 that includes ME', the complement of the transposase recognition sequence). After tagmentation using surface-bound transposome complexes, a DNA lesion intolerant polymerase, dNTPs, and a two-domain primer, such as the two-domain primer 43 in FIG. 4D, can be added. Upon exposure to denaturing conditions, e.g., heat, the other strand of the transposon and the attached target nucleic acid are released into solution. The two-domain primer 43 can be annealed to the ME' attached to the 3' end of the target nucleic acid. Extension is initiated at the ME' using the two-domain primer as template to result in asymmetric target nucleic acids. The asymmetric target nucleic acids can then be removed from the solid surface.

Index Sequences

In some embodiments it can be useful to identify the source of a target nucleic acid during the step of sequencing. Examples of when this is useful are readily apparent to the skilled person and include, but are not limited to, the simultaneous analysis of multiple libraries from different sources (e.g., different subject, sample, tissue, or cell type). The identification of the source of a target nucleic acid can be accomplished through the use of compartmentalization, e.g., distributing subsets of target nucleic acids into a plurality of compartments, uniquely labeling the target nucleic acids—typically by modifying to add an adapter that includes a unique index sequence—in each compartment, and then pooling the subsets. For instance, single cell combinatorial indexing ("sci-") methods typically use split-pool labeling. Accordingly, in some embodiments an index attached to each of the target nucleic acids present in a particular compartment, and the presence of the index is indicative of, or is used to identify, the compartment in which a population of nuclei or cells were present at a particular stage of the method. The use of indexes and the distribution of nucleic acids into compartments, also referred to as compartmentalization, is described herein.

An index sequence used herein can be any suitable sequence of any suitable number of nucleotides in length, e.g., 1, 2, 3, 4, 5, 6, 7, 8, 9, 10, 11, 12, 13, 14, 15, 16, 17, 18, 19, 20, or more. A four nucleotide tag gives a possibility of multiplexing 256 samples, and a six base tag enables 4096 samples to be processed. In some embodiments, the index is used to label the nucleic acids in a specific compartment.

As described herein, modification of an asymmetric target nucleic acid to add an index can be achieved during the production of a symmetric target nucleic acid. For instance, an index can be included in the symmetric adapter. Additional indexes can be selectively added to either end of an asymmetric target nucleic in subsequent steps.

Methods for modifying an asymmetric target nucleic acid by adding an index include, but are not limited to, direct inclusion with a primer, extension, transposition, or ligation. Examples of extension include, but are not limited to, hybridization of a primer, extension using reverse transcriptase, and amplification. The nucleotide sequence that is added to one or both ends of asymmetric target nucleic acids can also include one or more universal sequences and/or UMI. A universal sequence can be used as, for instance, a "landing pad" in a subsequent step to anneal a nucleotide sequence that can be used as a primer for addition of another nucleotide sequence, such as another index, universal sequence, and/or UMI to an asymmetric target nucleic acid. Thus, the incorporation of an index sequence can use a process that includes one, two, or more steps, using essentially any combination of extension (including hybridization, reverse transcriptase, and/or amplification), ligation, or transposition.

In some embodiments, the incorporation of an index occurs in one, two, three, or more rounds of split and pool indexing resulting in single, dual, triple, or multiple (e.g., four or more) indexed libraries, such as indexed single cell libraries.

The method can include multiple distribution steps, where a population of target nucleic acids, such as isolated nuclei or cells (also referred to herein as a pool) is split into subsets. While the following is discussed in terms of isolated nuclei or cells, the skilled person will appreciate that a "split and pool" step can be applied to any population of target nucleic acids. Typically, subsets of isolated nuclei or cells, e.g., subsets present in a plurality of compartments, are indexed with compartment specific indexes and then pooled. This compartmentalization of target nucleic acids can occur at any stage where an index is being added. For instance, target nucleic acids can be present in compartments when a symmetric adapter and/or when another adapter is added.

Accordingly, the method typically includes at least one "split and pool" step of taking pooled isolated nuclei or cells and distributing them and adding a compartment specific index, where the number of "split and pool" steps can depend on the number of different indexes that are added to the nucleic acid fragments. Each initial subset of nuclei or cells prior to indexing can be unique from other subsets. After indexing, the subsets can be pooled after indexing, split into subsets, indexed, and pooled again as needed until a sufficient number of indexes are added to the target nucleic acids. This process assigns unique index or index combinations to each single cell or nucleus. After indexing is complete, e.g., after one, two, three, or more indexes are added, the isolated nuclei or cells can be lysed. In some embodiments, adding an index and lysing can occur simultaneously.

The number of nuclei or cells present in a subset, and therefore in each compartment, can be at least 1. In one embodiment, the number of nuclei or cells present in a subset is no greater than 100,000,000, no greater than 10,000,000, no greater than 1,000,000, no greater than 100,000, no greater than 10,000, no greater than 4,000, no greater than 3,000, no greater than 2,000, or no greater than 1,000, no greater than 500, or no greater than 50. In one embodiment, the number of nuclei or cells present in a subset can be 1 to 1,000, 1,000 to 10,000, 10,000 to 100,000, 100,000 to 1,000,000, 1,000,000 to 10,000,000, or 10,000,000 to 100,000,000. In one embodiment, the number of nuclei or cells present in each subset is approximately equal. The number of nuclei present in a subset, and therefor in each compartment, is based in part on the desire to reduce index collisions, which is the presence of two nuclei or cells having the same index combination ending up in the same compartment in this step of the method. Methods for distributing nuclei or cells into subsets are known to the person skilled in the art and are routine and include fluorescence-activated cell sorting (FACS) simple dilution.

The number of compartments in the distribution steps (and subsequent addition of an index) can depend on the format used. For instance, the number of compartments can be from 2 to 96 compartments (when a 96-well plate is used), from 2 to 384 compartments (when a 384-well plate is used), or from 2 to 1536 compartments (when a 1536-well plate is used). In one embodiment, the number of compartments is 5000 or more (Takara Biosciences, icell8 system). In one embodiment, multiple plates can be used. In one embodiment, each compartment can be a droplet. When the type of compartment used is a droplet or well that contains two or more nuclei or cells, any number of droplets or wells can be used, such as at least 10,000, at least 100,000, at least 1,000,000, or at least 10,000,000 droplets. Subsets of isolated nuclei or cells are typically indexed in compartments before pooling.

Figure 5:
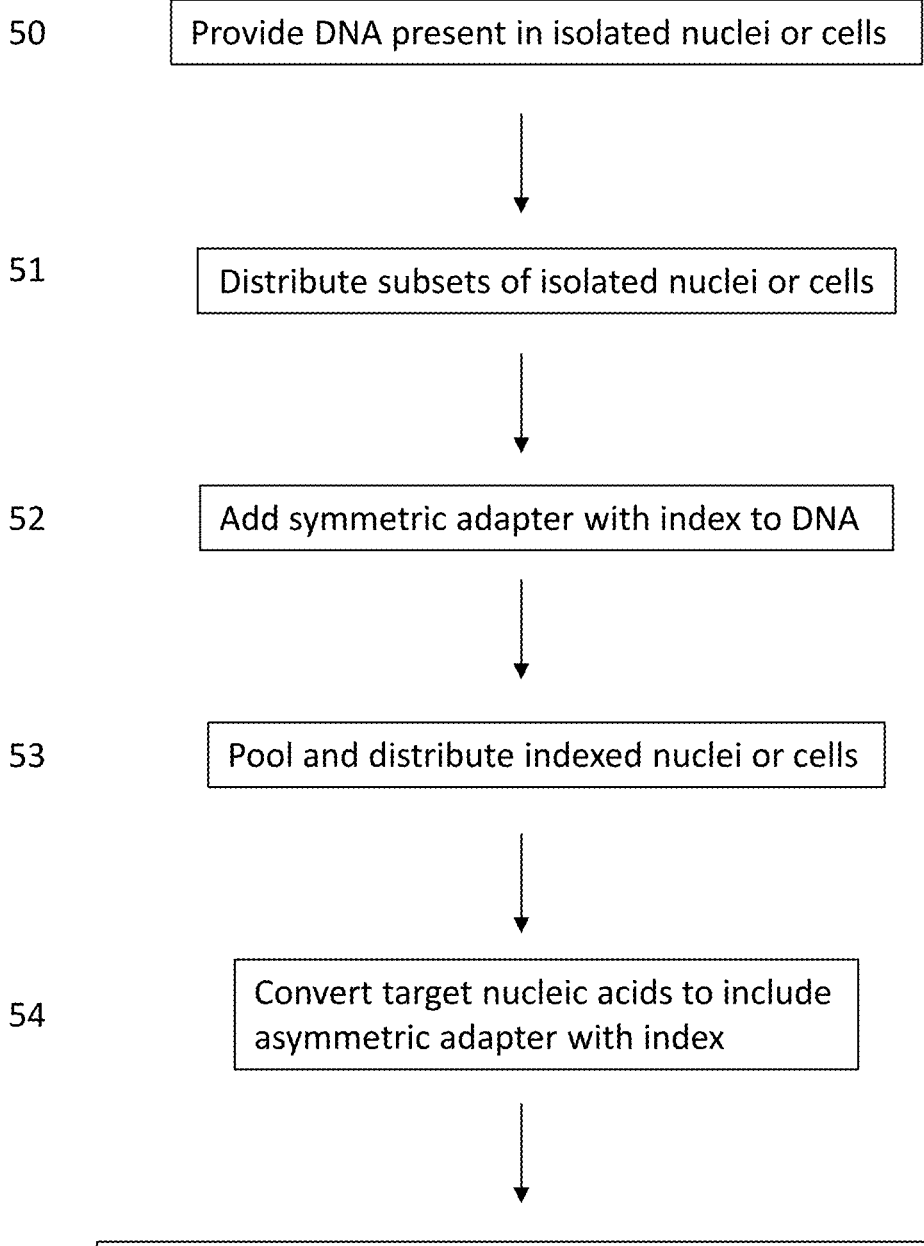
FIG. 5 shows a general block diagram of a general illustrative method for single-cell combinatorial indexing of according to the present disclosure.

FIG. 5 shows a general block diagram of a general illustrative method for single-cell combinatorial indexing of according to the present disclosure. The method includes providing isolated nuclei or cells (FIG. 5, block 50) and distributing the isolated nuclei or cells into a plurality of compartments (FIG. 5, block 51). Block 40 refers to DNA, and the skilled person will recognize that the DNA can be, for instance, genomic DNA or DNA derived from RNA. In this embodiment of the method, the isolated nuclei or cells are indexed with compartment specific indexes by addition of the symmetric adapter (FIG. 5, block 52) and then pooled (FIG. 5, block 53). Accordingly, the method typically includes at least one "split and pool" step of taking pooled isolated nuclei or cells, distributing them, and adding a compartment specific index, where the number of "split and pool" steps can depend on the number of different indexes that are added to the target nucleic acids. If a second index is to be added with the asymmetric adapter, the pooled isolated nuclei or cells are distributed into a second plurality of compartments (FIG. 5, block 53) and indexed with a compartment specific index by addition of the asymmetric adapter (FIG. 5, block 54). Optionally, the asymmetric target nucleic acids can then be amplified (FIG. 5, block 55). The amplification of the asymmetric target nucleic acids can include the addition of other useful sequences to one or both ends, including but not limited to index sequences, UMI sequences, and/or universal sequences, and can be combined with further split and pool indexing.

The resulting indexed target nucleic acids collectively provide a library of nucleic acids that can be sequenced. The term library, also referred to herein as a sequencing library, refers to the collection of modified nucleic acids containing known universal sequences at their 3' and 5' ends.

Applications

The methods provided by the present disclosure can be easily integrated into essentially any application that includes sequencing library preparation, such as whole genome, transcriptome, methylated, accessible (e.g., ATAC), and conformational state (e.g., HiC). It can be particularly useful in essentially any application requiring high library conversion such as, but not limited to, single cell combinatorial indexing (sci) methods like sci-WGS-seq, sci-MET-seq, sci-ATAC-seq, and sci-RNA-seq. Instead of focusing sequencing library production on the generation of target nucleic acids having different universal sequences on each side (e.g., asymmetric), integrating the methods provided by the present disclosure into sequencing library production includes the more efficient generation of target nucleic acids having the same universal sequences on each side (e.g., symmetric). Upon generation of symmetric fragments, methods described herein for conversion of symmetric fragments to asymmetric fragments can be applied. A multitude of sequencing library methods are known to a skilled person that can be used in the construction of whole-genome or targeted libraries (see, for instance, Sequencing Methods Review, available on the world wide web at genomics.umn-.edu/downloads/sequencing-methods-review.pdf).

Figure 6:
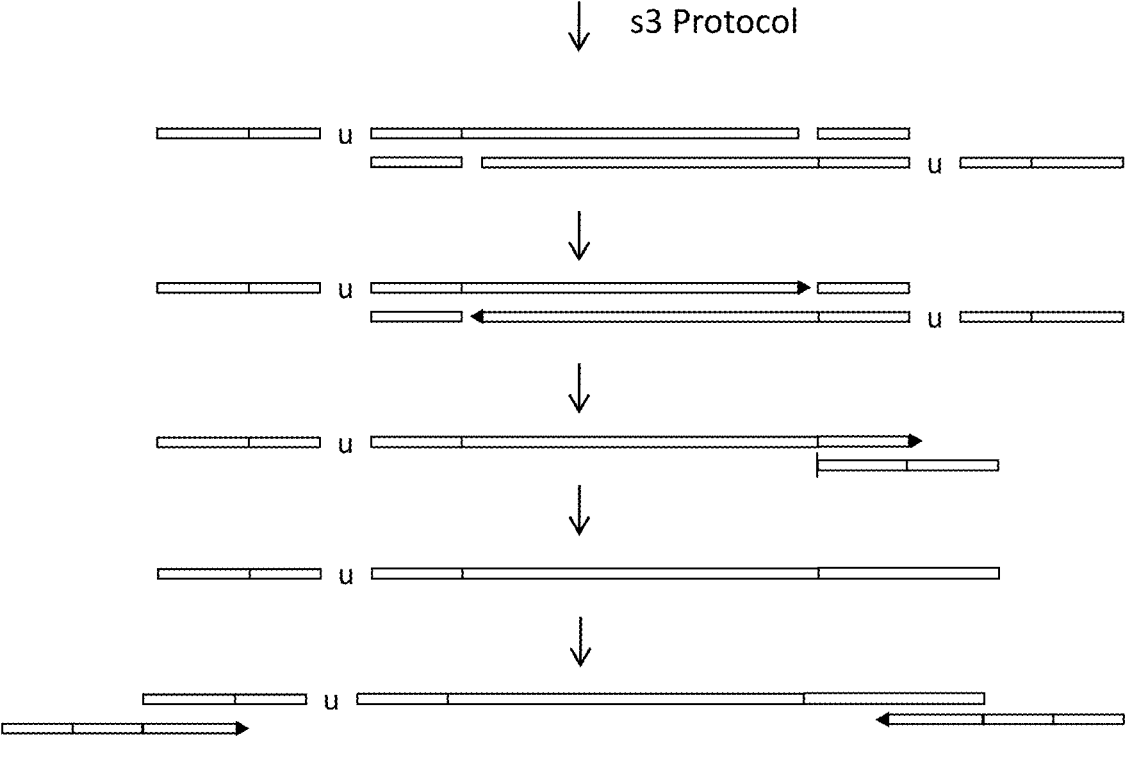
FIG. 6 shows schematic drawings of an embodiment of converting whole cell genomic DNA to symmetric target nucleic acids and then to asymmetric target nucleic acids (s3-WGS) according to various aspects of the disclosure presented herein. For simplicity, only one target nucleic acid is shown.

In some embodiments, the application is whole-genome or targeted sequencing. In general, tissue, individual cells, or individual nuclei are processed as described herein to result in symmetric target nucleic acids (see Example 2). In some embodiments, individual cells or individual nuclei can be treated to unbind nucleosomes from genomic DNA (WO 2018/018008)). The symmetric modified target nucleic acids can then be processed as described herein to generate asymmetric modified target nucleic acids. For instance, as shown in FIG. 6, nucleic can be fixed to maintain nuclear integrity, exposed to conditions to remove nucleosomes from the genomic DNA to make the entire genome accessible, and then have one population of adapters inserted, for instance by tagmentation, to produce symmetric target nucleic acids. Subsequently, the symmetric target nucleic acids can be converted as described herein to asymmetric target nucleic acids.

Figure 7:
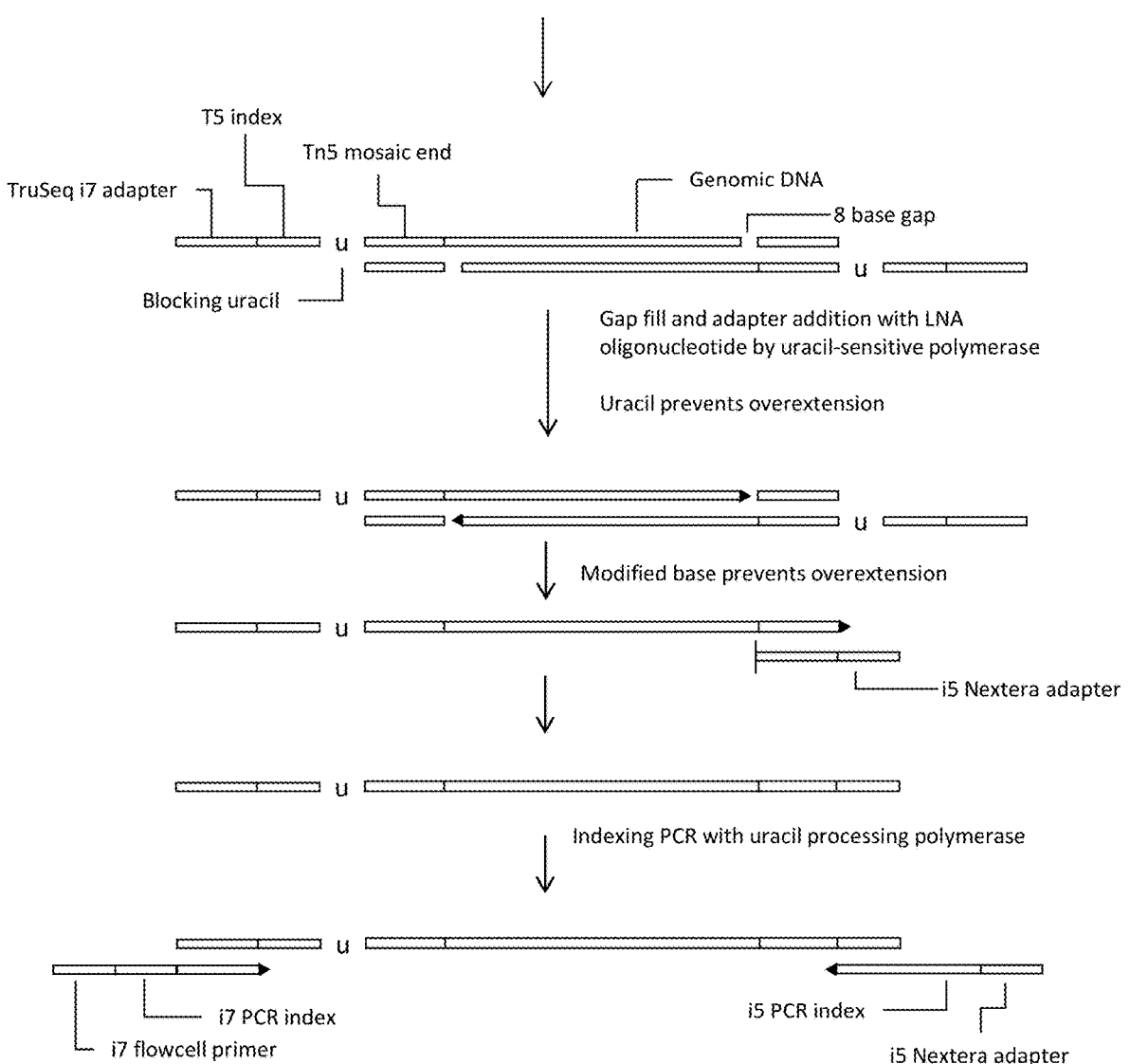
FIG. 7 shows schematic drawings of an embodiment of converting accessible genomic DNA to symmetric target nucleic acids and then to asymmetric target nucleic acids (s3-ATAC) according to various aspects of the disclosure presented herein. For simplicity, only one target nucleic acid is shown.

In some embodiments, the application is for probing accessible DNA, such as ATAC-seq (Assay for Transposase-Accessible Chromatin using sequencing) for the identification of accessible DNA. In general, tissue, individual cells, or individual nuclei with intact nucleosomes can be processed as described herein to result in symmetric target nucleic acids (see Example 2). The symmetric modified target nucleic acids can then be processed as described herein to generate asymmetric modified target nucleic acids. For instance, as shown in FIG. 7, genomic DNA that includes bound nucleosomes can be tagmented to produce symmetric target nucleic acids. Subsequently, the symmetric target nucleic acids can be converted as described herein to asymmetric target nucleic acids.

In some embodiments, the application is for sequencing RNA, such as mRNA. RNA is converted into DNA, and in contrast to applications using DNA as the starting material, an adapter can be added to one or both ends of the RNA molecule during the processing to DNA. This provides for the option of 5' and/or 3' profiling of RNA or full-length RNA profiling. For instance, as shown in FIG. 8, in one illustrative embodiment mRNA molecules can be subjected to reverse transcriptase in the presence of a poly-T primer that includes a universal sequence and a template-switch primer, to result in a double stranded DNA which includes an adapter (shown as CS1) at each end (FIG. 8A). After exposure of the resulting double stranded DNAs to trans-posome complexes (FIG. 8B) and converting the symmetric adapters to asymmetric adapters (FIG. 8C), three different populations can result (FIG. 8D). One population (shown as 3' End) can result when transposon sequences insert into double stranded DNA and the other end of the resulting target nucleic acids include the sequences corresponding with the original 3' end of the mRNA. A second population (shown as RNA Body) can result when transposon sequences insert into two positions within the double stranded DNA. A third population (shown as 5' End) can result when transposon sequences insert into double stranded DNA and the other end of the resulting target nucleic acids include the sequences corresponding with the original 5' end of the mRNA.

In some embodiments, the application is methylation sequencing. A wide-range of methods are described in literature or are known to a skilled worker in the art that enable the analysis of the methylation or hydroxy-methyl-ation state, Barros-Silva et al., Genes (Basel). 2018 September; 9(9): 429). Chemical (e.g., sodium bisulfite or borate chemistry) or enzymatic methods of conversion can be used in various methylation sequencing methods including, but not limited to, BS-seq, TAB-seq, RRBS-seq, MeDip-seq, MethylCap-seq, MBD-seq, Nanopore-seq, oxBS-seq, SeqCap Epi CpGiant, BSAS, WGBS, and sci-MET (WO 2018/226708).

In one embodiment, the application is protein analysis. The protein can be intracellular or surface bound, isolated or present in a biological sample. Various methods are avail-able to the skilled person. A common method often used for protein detection is to label an antibody or fab-fragment with an oligonucleotide tag, affinity bind the antibody with the protein of interest, and use the oligonucleotide tag as a readout or for detection. The oligonucleotide tag can contain an index sequence, a UMI, a universal sequence, or a combination thereof.

In some embodiments, the application is a co-assay, where two or more different analytes or information are evaluated. Examples of analytes include, but are not limited to DNA, RNA, and protein. The nucleic acid can be different states, for instance, an epigenetic state (ATAC, meC, 5-hy-droxyMe, etc.), or a conformational state (e.g. HiC, 3C, chromatin state, etc). Examples include assays that analyze DNA and RNA, DNA and or/RNA and an epigenetic state (ATAC, meC, 5-hydroxyMe etc), DNA and a conforma-tional state (e.g. HiC, 3C, chromatin state, etc.).

Figure 9:
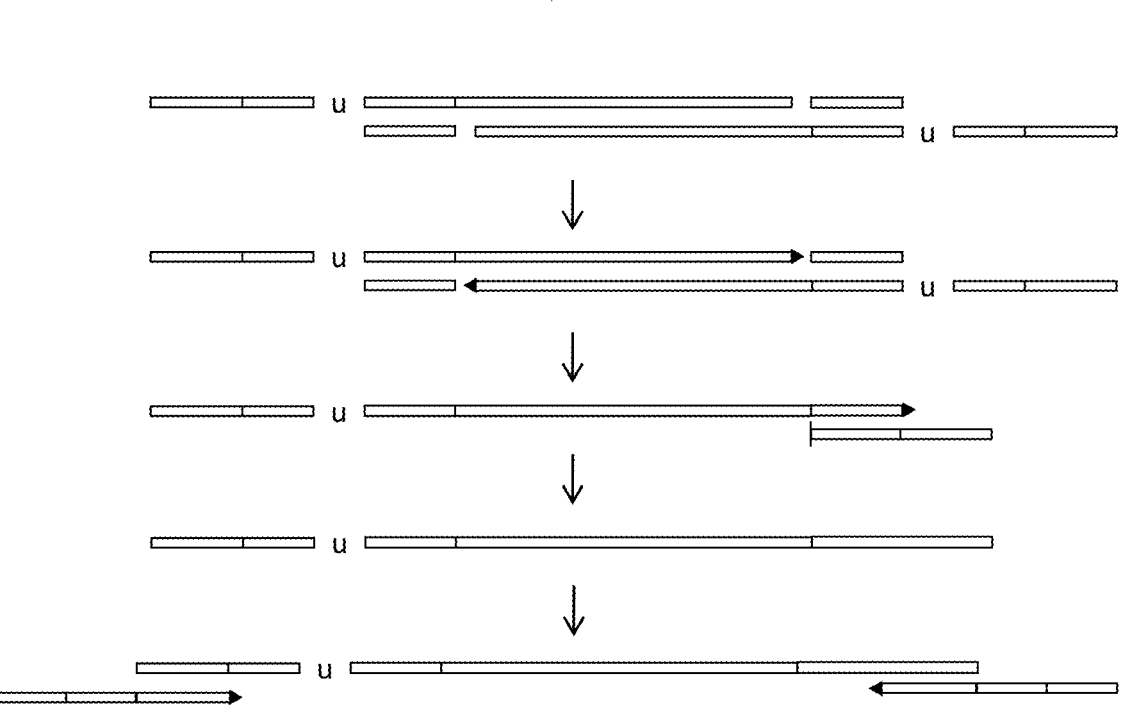
FIG. 9 shows schematic drawings of an embodiment of a co-assay converting whole cell genomic DNA to symmetric target nucleic acids and then to asymmetric target nucleic acids (s3-GCC) according to various aspects of the disclosure presented herein. For simplicity, only one target nucleic acid is shown.

An example of a co-assay is the preparation of genomic DNA for genome plus chromatin conformation sequencing, referred to herein as GCC-seq. GCC-seq combines whole genome sequencing and chromatin conformation analysis, and when combined with single cell or single nuclei and split and pool indexing, captures chromatin interaction at higher rates than routine Hi-C types of methods (see Example 2). As illustrated in FIG. 9, genomic DNA is processed by, for instance, fixation, digestion with a restriction enzyme, prox-imity ligation, and nucleosome depletion, and then adapters added to result in symmetric target nucleic acids. Optionally, molecule capture can be used. The symmetric modified target nucleic acids can be processed as described herein.

Preparation of Immobilized Samples for Sequencing

The library of indexed target nucleic acids can be pre-pared for sequencing. Methods for attaching indexed target nucleic acids to a substrate are known in the art. In one embodiment, indexed fragments are enriched using a plu-rality of capture oligonucleotides having specificity for the indexed fragments, and the capture oligonucleotides can be immobilized on a surface of a solid substrate such as a flow cell or a bead. For instance, capture oligonucleotides can include a first member of a universal binding pair, and where a second member of the binding pair is immobilized on a surface of a solid substrate. Likewise, methods for ampli-fying immobilized target nucleic acids include, but are not limited to, bridge amplification and kinetic exclusion. Meth-ods for immobilizing and amplifying prior to sequencing are described in, for instance, Bignell et al. (U.S. Pat. No. 8,053,192), Gunderson et al. (WO2016/130704), Shen et al. (U.S. Pat. No. 8,895,249), and Pipenburg et al. (U.S. Pat. No. 9,309,502).

A pooled sample can be immobilized in preparation for sequencing. Sequencing can be performed as an array of single molecules or can be amplified prior to sequencing. The amplification can be carried out using one or more immobilized primers. The immobilized primer(s) can be, for instance, a lawn on a planar surface, or on a pool of beads. The pool of beads can be isolated into an emulsion with a single bead in each "compartment" of the emulsion. At a concentration of only one template per "compartment," only a single template is amplified on each bead.

The term "solid-phase amplification" as used herein refers to any nucleic acid amplification reaction carried out on or in association with a solid support such that all or a portion of the amplified products are immobilized on the solid support as they are formed. In particular, the term encom-passes solid-phase polymerase chain reaction (solid-phase PCR) and solid phase isothermal amplification which are reactions analogous to standard solution phase amplifica-tion, except that one or both of the forward and reverse amplification primers is/are immobilized on the solid sup-port. Solid phase PCR covers systems such as emulsions, where one primer is anchored to a bead and the other is in free solution, and colony formation in solid phase gel matrices wherein one primer is anchored to the surface, and one is in free solution.

In some embodiments, the solid support comprises a patterned surface. A "patterned surface" refers to an arrange-ment of different regions in or on an exposed layer of a solid support. For example, one or more of the regions can be features where one or more amplification primers are pres-ent. The features can be separated by interstitial regions where amplification primers are not present. In some embodiments, the pattern can be an x-y format of features that are in rows and columns. In some embodiments, the pattern can be a repeating arrangement of features and/or interstitial regions. In some embodiments, the pattern can be a random arrangement of features and/or interstitial regions.

Exemplary patterned surfaces that can be used in the methods and compositions set forth herein are described in U.S. Pat. Nos. 8,778,848, 8,778,849 and 9,079,148, and U.S. Pat. Appl. Pub. No. 2014/0243224.

In some embodiments, the solid support includes an array of wells or depressions in a surface. This may be fabricated as is generally known in the art using a variety of techniques, including, but not limited to, photolithography, stamping techniques, molding techniques and micro-etching techniques. As will be appreciated by those in the art, the technique used will depend on the composition and shape of the array substrate.

The features in a patterned surface can be wells in an array of wells (e.g. microwells or nanowells) on glass, silicon, plastic or other suitable solid supports with patterned, covalently-linked gel such as poly(N-(5-azidoacetamidylpentyl) acrylamide-co-acrylamide) (PAZAM, see, for example, US Pub. No. 2013/184796, WO 2016/066586, and WO 2015/002813). The process creates gel pads used for sequencing that can be stable over sequencing runs with a large number of cycles. The covalent linking of the polymer to the wells is helpful for maintaining the gel in the structured features throughout the lifetime of the structured substrate during a variety of uses. However, in many embodiments the gel need not be covalently linked to the wells. For example, in some conditions silane free acrylamide (SFA, see, for example, U.S. Pat. No. 8,563,477) which is not covalently attached to any part of the structured substrate, can be used as the gel material.

In particular embodiments, a structured substrate can be made by patterning a solid support material with wells (e.g. microwells or nanowells), coating the patterned support with a gel material (e.g. PAZAM, SFA, or chemically modified variants thereof, such as the azidolyzed version of SFA (azido-SFA)) and polishing the gel coated support, for example via chemical or mechanical polishing, thereby retaining gel in the wells but removing or inactivating substantially all of the gel from the interstitial regions on the surface of the structured substrate between the wells. Primer nucleic acids can be attached to gel material. A solution of modified target nucleic acids can then be contacted with the polished substrate such that individual modified target nucleic acids will seed individual wells via interactions with primers attached to the gel material; however, the target nucleic acids will not occupy the interstitial regions due to absence or inactivity of the gel material. Amplification of the modified target nucleic acids will be confined to the wells since absence or inactivity of gel in the interstitial regions prevents outward migration of the growing nucleic acid colony. The process can be conveniently manufactured, being scalable and utilizing conventional micro- or nano-fabrication methods.

Although the disclosure encompasses "solid-phase" amplification methods in which only one amplification primer is immobilized (the other primer usually being present in free solution), in one embodiment the solid support is provided with both the forward and the reverse primers immobilized. In practice, there will be a 'plurality' of identical forward primers and/or a 'plurality' of identical reverse primers immobilized on the solid support, since the amplification process requires an excess of primers to sustain amplification. References herein to forward and reverse primers are to be interpreted accordingly as encompassing a 'plurality' of such primers unless the context indicates otherwise.

As will be appreciated by the skilled reader, any given amplification reaction requires at least one type of forward primer and at least one type of reverse primer specific for the template to be amplified. However, in certain embodiments the forward and reverse primers may include template-specific portions of identical sequence, and may have entirely identical nucleotide sequence and structure (including any non-nucleotide modifications). In other words, it is possible to carry out solid-phase amplification using only one type of primer, and such single-primer methods are encompassed within the scope of the disclosure. Other embodiments may use forward and reverse primers which contain identical template-specific sequences but which differ in some other structural features. For example, one type of primer may contain a non-nucleotide modification which is not present in the other.

Primers for solid-phase amplification are preferably immobilized by single point covalent attachment to the solid support at or near the 5' end of the primer, leaving the template-specific portion of the primer free to anneal to its cognate template and the 3' hydroxyl group free for primer extension. Any suitable covalent attachment means known in the art may be used for this purpose. The chosen attachment chemistry will depend on the nature of the solid support, and any derivatization or functionalization applied to it. The primer itself may include a moiety, which may be a non-nucleotide chemical modification, to facilitate attachment. In a particular embodiment, the primer may include a sulphur-containing nucleophile, such as phosphorothioate or thiophosphate, at the 5' end. In the case of solid-supported polyacrylamide hydrogels, this nucleophile will bind to a bromoacetamide group present in the hydrogel. A more particular means of attaching primers and templates to a solid support is via 5' phosphorothioate attachment to a hydrogel comprised of polymerized acrylamide and N-(5-bromoacetamidylpentyl) acrylamide (BRAPA), as described in Int. Pub. No. WO 05/065814.

Certain embodiments of the disclosure may make use of solid supports that include an inert substrate or matrix (e.g. glass slides, polymer beads, etc.) which has been "functionalized," for example by application of a layer or coating of an intermediate material including reactive groups which permit covalent attachment to biomolecules, such as polynucleotides. Examples of such supports include, but are not limited to, polyacrylamide hydrogels supported on an inert substrate such as glass. In such embodiments, the biomolecules (e.g. polynucleotides) may be directly covalently attached to the intermediate material (e.g. the hydrogel), but the intermediate material may itself be non-covalently attached to the substrate or matrix (e.g. the glass substrate). The term "covalent attachment to a solid support" is to be interpreted accordingly as encompassing this type of arrangement.

The pooled samples may be amplified on beads wherein each bead contains a forward and reverse amplification primer. In one embodiment, a library of modified target nucleic acids is used to prepare clustered arrays of nucleic acid colonies, analogous to those described in U.S. Pub. No. 2005/0100900, U.S. Pat. No. 7,115,400, WO 00/18957 and WO 98/44151 by solid-phase amplification and more particularly solid phase isothermal amplification. The terms 'cluster' and 'colony' are used interchangeably herein to refer to a discrete site on a solid support including a plurality of identical immobilized nucleic acid strands and a plurality of identical immobilized complementary nucleic acid strands. The term "clustered array" refers to an array formed from such clusters or colonies. In this context, the term "array" is not to be understood as requiring an ordered arrangement of clusters.

The term "solid phase" or "surface" is used to mean either a planar array wherein primers are attached to a flat surface, for example, glass, silica or plastic microscope slides or similar flow cell devices; beads, wherein either one or two primers are attached to the beads and the beads are amplified; or an array of beads on a surface after the beads have been amplified.

Clustered arrays can be prepared using either a process of thermocycling, as described in WO 98/44151, or a process whereby the temperature is maintained as a constant, and the cycles of extension and denaturing are performed using changes of reagents. Such isothermal amplification methods are described in patent application numbers WO 02/46456 and U.S. Pub. No. 2008/0009420.

It will be appreciated that any of the amplification methodologies described herein or generally known in the art may be used with universal or target-specific primers to amplify immobilized DNA fragments. Suitable methods for amplification include, but are not limited to, the polymerase chain reaction (PCR), strand displacement amplification (SDA), transcription mediated amplification (TMA) and nucleic acid sequence-based amplification (NASBA), as described in U.S. Pat. No. 8,003,354. The above amplification methods may be employed to amplify one or more nucleic acids of interest. For example, PCR, including multiplex PCR, SDA, TMA, NASBA and the like may be utilized to amplify immobilized DNA fragments. In some embodiments, primers directed specifically to the polynucleotide of interest are included in the amplification reaction.

Other suitable methods for amplification of polynucleotides may include oligonucleotide extension and ligation, rolling circle amplification (RCA) (Lizardi et al., Nat. Genet. 19:225-232 (1998)) and oligonucleotide ligation assay (OLA) (See generally U.S. Pat. Nos. 7,582,420, 5,185,243, 5,679,524 and 5,573,907; EP 0 320 308 B1; EP 0 336 731 B1; EP 0 439 182 B1; WO 90/01069; WO 89/12696; and WO 89/09835) technologies. It will be appreciated that these amplification methodologies may be designed to amplify immobilized DNA fragments. For example, in some embodiments, the amplification method may include ligation probe amplification or oligonucleotide ligation assay (OLA) reactions that contain primers directed specifically to the nucleic acid of interest. In some embodiments, the amplification method may include a primer extension-ligation reaction that contains primers directed specifically to the nucleic acid of interest. As a non-limiting example of primer extension and ligation primers that may be specifically designed to amplify a nucleic acid of interest, the amplification may include primers used for the GoldenGate assay (ILLUMINA®, Inc., San Diego, CA) as exemplified by U.S. Pat. Nos. 7,582,420 and 7,611,869.

DNA nanoballs can also be used in combination with methods, systems, compositions and kits as described herein. Methods for creating and using DNA nanoballs for genomic sequencing can be found at, for example, US patents and publications U.S. Pat. No. 7,910,354, 2009/0264299, 2009/0011943, 2009/0005252, 2009/0155781, 2009/0118488 and as described in, for example, Drmanac et al. (2010, Science 327(5961): 78-81). Briefly, following production of asymmetric target nucleic acids, the asymmetric target nucleic acids are circularized and amplified by rolling circle amplification (Lizardi et al., 1998. Nat. Genet. 19:225-232; US 2007/0099208 A1). The extended concatameric structure of the amplicons promotes coiling creates compact DNA nanoballs. The DNA nanoballs can be captured on substrates, preferably to create an ordered or patterned array such that distance between each nanoball is maintained thereby allowing sequencing of the separate DNA nanoballs. In some embodiments such as those used by Complete Genomics (Mountain View, Calif), consecutive rounds of adapter addition, amplification, and digestion are carried out prior to circularization to produce head to tail constructs having several target nucleic acids separated by adapter sequences.

Exemplary isothermal amplification methods that may be used in a method of the present disclosure include, but are not limited to, Multiple Displacement Amplification (MDA) as exemplified by, for example Dean et al., Proc. Natl. Acad. Sci. USA 99:5261-66 (2002) or isothermal strand displacement nucleic acid amplification exemplified by, for example U.S. Pat. No. 6,214,587. Other non-PCR-based methods that may be used in the present disclosure include, for example, strand displacement amplification (SDA) which is described in, for example Walker et al., Molecular Methods for Virus Detection, Academic Press, Inc., 1995; U.S. Pat. Nos. 5,455, 166, and 5,130,238, and Walker et al., Nucl. Acids Res. 20:1691-96 (1992) or hyper-branched strand displacement amplification which is described in, for example Lage et al., Genome Res. 13:294-307 (2003). Isothermal amplification methods may be used with, for instance, the strand-displacing Phi 29 polymerase or Bst DNA polymerase large fragment, 5'→3' exo-for random primer amplification of genomic DNA. The use of these polymerases takes advantage of their high processivity and strand displacing activity. High processivity allows the polymerases to produce fragments that are 10-20 kb in length. As set forth above, smaller fragments may be produced under isothermal conditions using polymerases having low processivity and strand-displacing activity such as Klenow polymerase. Additional description of amplification reactions, conditions and components are set forth in detail in the disclosure of U.S. Pat. No. 7,670,810.

In some embodiments, isothermal amplification can be performed using kinetic exclusion amplification (KEA), also referred to as exclusion amplification (ExAmp). A nucleic acid library of the present disclosure can be made using a method that includes a step of reacting an amplification reagent to produce a plurality of amplification sites that each includes a substantially clonal population of amplicons from an individual target nucleic acid that has seeded the site. In some embodiments, the amplification reaction proceeds until a sufficient number of amplicons are generated to fill the capacity of the respective amplification site. Filling an already seeded site to capacity in this way inhibits target nucleic acids from landing and amplifying at the site thereby producing a clonal population of amplicons at the site. In some embodiments, apparent clonality can be achieved even if an amplification site is not filled to capacity prior to a second target nucleic acid arriving at the site. Under some conditions, amplification of a first target nucleic acid can proceed to a point that a sufficient number of copies are made to effectively outcompete or overwhelm production of copies from a second target nucleic acid that is transported to the site. For example, in an embodiment that uses a bridge amplification process on a circular feature that is smaller than 500 nm in diameter, it has been determined that after 14 cycles of exponential amplification for a first target nucleic acid, contamination from a second target nucleic acid at the same site will produce an insufficient number of contaminating amplicons to adversely impact sequencing-by-synthesis analysis on an ILLUMINA® sequencing platform.

In some embodiments, amplification sites in an array can be, but need not be, entirely clonal. Rather, for some applications, an individual amplification site can be predominantly populated with amplicons from a first asymmetric target nucleic acid and can also have a low level of contaminating amplicons from a second asymmetric target nucleic acid. An array can have one or more amplification sites that have a low level of contaminating amplicons so long as the level of contamination does not have an unacceptable impact on a subsequent use of the array. For example, when the array is to be used in a detection application, an acceptable level of contamination would be a level that does not impact signal to noise or resolution of the detection technique in an unacceptable way. Accordingly, apparent clonality will generally be relevant to a particular use or application of an array made by the methods set forth herein. Exemplary levels of contamination that can be acceptable at an individual amplification site for particular applications include, but are not limited to, at most 0.1%, 0.5%, 1%, 5%, 10% or 25% contaminating amplicons. An array can include one or more amplification sites having these exemplary levels of contaminating amplicons. For example, up to 5%, 10%, 25%, 50%, 75%, or even 100% of the amplification sites in an array can have some contaminating amplicons. It will be understood that in an array or other collection of sites, at least 50%, 75%, 80%, 85%, 90%, 95% or 99% or more of the sites can be clonal or apparently clonal.

In some embodiments, kinetic exclusion can occur when a process occurs at a sufficiently rapid rate to effectively exclude another event or process from occurring. Take for example the making of a nucleic acid array where sites of the array are randomly seeded with asymmetric target nucleic acids from a solution and copies of the asymmetric target nucleic acids are generated in an amplification process to fill each of the seeded sites to capacity. In accordance with the kinetic exclusion methods of the present disclosure, the seeding and amplification processes can proceed simultaneously under conditions where the amplification rate exceeds the seeding rate. As such, the relatively rapid rate at which copies are made at a site that has been seeded by a first target nucleic acid will effectively exclude a second nucleic acid from seeding the site for amplification. Kinetic exclusion amplification methods can be performed as described in detail in the disclosure of U.S. Pat. Appl. Pub. No. 2013/0338042.

Kinetic exclusion can exploit a relatively slow rate for initiating amplification (e.g. a slow rate of making a first copy of an asymmetric target nucleic acids) vs. a relatively rapid rate for making subsequent copies of the asymmetric target nucleic acids (or of the first copy of the asymmetric target nucleic acids). In the example of the previous paragraph, kinetic exclusion occurs due to the relatively slow rate of asymmetric target nucleic acids seeding (e.g. relatively slow diffusion or transport) vs. the relatively rapid rate at which amplification occurs to fill the site with copies of the asymmetric target nucleic acid seed. In another exemplary embodiment, kinetic exclusion can occur due to a delay in the formation of a first copy of an asymmetric target nucleic acid that has seeded a site (e.g. delayed or slow activation) vs. the relatively rapid rate at which subsequent copies are made to fill the site. In this example, an individual site may have been seeded with several different asymmetric target nucleic acids (e.g. several asymmetric target nucleic acids can be present at each site prior to amplification). However, first copy formation for any given asymmetric target nucleic acid can be activated randomly such that the average rate of first copy formation is relatively slow compared to the rate at which subsequent copies are generated. In this case, although an individual site may have been seeded with several different asymmetric target nucleic acids, kinetic exclusion will allow only one of those to be amplified. More specifically, once a first asymmetric target nucleic acid has been activated for amplification, the site will rapidly fill to capacity with its copies, thereby preventing copies of a second asymmetric target nucleic acid from being made at the site.

In one embodiment, the method is carried out to simultaneously (i) asymmetric target nucleic acids to amplification sites at an average transport rate, and (ii) amplify the asymmetric target nucleic acids that are at the amplification sites at an average amplification rate, wherein the average amplification rate exceeds the average transport rate (U.S. Pat. No. 9,169,513). Accordingly, kinetic exclusion can be achieved in such embodiments by using a relatively slow rate of transport. For example, a sufficiently low concentration of asymmetric target nucleic acids can be selected to achieve a desired average transport rate, lower concentrations resulting in slower average rates of transport. Alternatively or additionally, a high viscosity solution and/or presence of molecular crowding reagents in the solution can be used to reduce transport rates. Examples of useful molecular crowding reagents include, but are not limited to, polyethylene glycol (PEG), ficoll, dextran, or polyvinyl alcohol. Exemplary molecular crowding reagents and formulations are set forth in U.S. Pat. No. 7,399,590, which is incorporated herein by reference. Another factor that can be adjusted to achieve a desired transport rate is the average size of the target nucleic acids.

An amplification reagent can include further components that facilitate amplicon formation, and in some cases increase the rate of amplicon formation. An example is a recombinase. Recombinase can facilitate amplicon formation by allowing repeated invasion/extension. More specifically, recombinase can facilitate invasion of a asymmetric target nucleic acid by the polymerase and extension of a primer by the polymerase using the asymmetric target nucleic acid as a template for amplicon formation. This process can be repeated as a chain reaction where amplicons produced from each round of invasion/extension serve as templates in a subsequent round. The process can occur more rapidly than standard PCR since a denaturation cycle (e.g. via heating or chemical denaturation) is not required. As such, recombinase-facilitated amplification can be carried out isothermally. It is generally desirable to include ATP, or other nucleotides (or in some cases non-hydrolyzable analogs thereof) in a recombinase-facilitated amplification reagent to facilitate amplification. A mixture of recombinase and single stranded binding (SSB) protein is particularly useful as SSB can further facilitate amplification. Exemplary formulations for recombinase-facilitated amplification include those sold commercially as TwistAmp kits by TwistDx (Cambridge, UK). Useful components of recombinase-facilitated amplification reagent and reaction conditions are set forth in U.S. Pat. Nos. 5,223,414 and 7,399,590.

Another example of a component that can be included in an amplification reagent to facilitate amplicon formation and in some cases to increase the rate of amplicon formation is a helicase. Helicase can facilitate amplicon formation by allowing a chain reaction of amplicon formation. The process can occur more rapidly than standard PCR since a denaturation cycle (e.g. via heating or chemical denaturation) is not required. As such, helicase-facilitated amplification can be carried out isothermally. A mixture of helicase and single stranded binding (SSB) protein is particularly useful as SSB can further facilitate amplification. Exemplary formulations for helicase-facilitated amplification include those sold commercially as IsoAmp kits from Biohelix (Beverly, MA). Further, examples of useful formulations that include a helicase protein are described in U.S. Pat. Nos. 7,399,590 and 7,829,284.

Yet another example of a component that can be included in an amplification reagent to facilitate amplicon formation and in some cases increase the rate of amplicon formation is an origin binding protein.

Methods of Sequencing

Following attachment of asymmetric target nucleic acids to a surface, the sequence of the immobilized and amplified asymmetric target nucleic acids is determined. Sequencing can be carried out using any suitable sequencing technique, and methods for determining the sequence of immobilized and amplified asymmetric modified target nucleic acids, including strand re-synthesis, are known in the art and are described in, for instance, Bignell et al. (U.S. Pat. No. 8,053,192), Gunderson et al. (WO2016/130704), Shen et al. (U.S. Pat. No. 8,895,249), and Pipenburg et al. (U.S. Pat. No. 9,309,502).

The methods described herein can be used in conjunction with a variety of nucleic acid sequencing techniques. Particularly applicable techniques are those wherein nucleic acids are attached at fixed locations in an array such that their relative positions do not change and wherein the array is repeatedly imaged. Embodiments in which images are obtained in different color channels, for example, coinciding with different labels used to distinguish one nucleotide base type from another are particularly applicable. In some embodiments, the process to determine the nucleotide sequence of an asymmetric target nucleic acid can be an automated process. Preferred embodiments include sequencing-by-synthesis ("SBS") techniques.

SBS techniques generally involve the enzymatic extension of a nascent nucleic acid strand through the iterative addition of nucleotides against a template strand. In traditional methods of SBS, a single nucleotide monomer may be provided to a target nucleotide in the presence of a polymerase in each delivery. However, in the methods described herein, more than one type of nucleotide monomer can be provided to a target nucleic acid in the presence of a polymerase in a delivery.

In one embodiment, a nucleotide monomer includes locked nucleic acids (LNAs) or bridged nucleic acids (BNAs). The use of LNAs or BNAs in a nucleotide monomer increases hybridization strength between a nucleotide monomer and a sequencing primer sequence present on an immobilized asymmetric modified target nucleic acid.

SBS can use nucleotide monomers that have a terminator moiety or those that lack any terminator moieties. Methods using nucleotide monomers lacking terminators include, for example, pyrosequencing and sequencing using γ-phosphate-labeled nucleotides, as set forth in further detail herein. In methods using nucleotide monomers lacking terminators, the number of nucleotides added in each cycle is generally variable and dependent upon the template sequence and the mode of nucleotide delivery. For SBS techniques that use nucleotide monomers having a terminator moiety, the terminator can be effectively irreversible under the sequencing conditions used as is the case for traditional Sanger sequencing which utilizes dideoxynucleotides, or the terminator can be reversible as is the case for sequencing methods developed by Solexa (now ILLUMINA®, Inc.).

SBS techniques can use nucleotide monomers that have a label moiety or those that lack a label moiety. Accordingly, incorporation events can be detected based on a characteristic of the label, such as fluorescence of the label; a characteristic of the nucleotide monomer such as molecular weight or charge; a byproduct of incorporation of the nucleotide, such as release of pyrophosphate; or the like. In embodiments where two or more different nucleotides are present in a sequencing reagent, the different nucleotides can be distinguishable from each other, or alternatively the two or more different labels can be the indistinguishable under the detection techniques being used. For example, the different nucleotides present in a sequencing reagent can have different labels and they can be distinguished using appropriate optics as exemplified by the sequencing methods developed by Solexa (now ILLUMINA®, Inc.).

Preferred embodiments include pyrosequencing techniques. Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." Analytical Biochemistry 242(1), 84-9; Ronaghi, M. (2001) "Pyrosequencing sheds light on DNA sequencing." Genome Res. 11(1), 3-11; Ronaghi, M., Uhlen, M. and Nyren, P. (1998) "A sequencing method based on real-time pyrophosphate." Science 281(5375), 363; U.S. Pat. Nos. 6,210,891; 6,258,568 and 6,274,320). In pyrosequencing, released PPi can be detected by being immediately converted to adenosine triphosphate (ATP) by ATP sulfurase, and the level of ATP generated is detected via luciferase-produced photons. The nucleic acids to be sequenced can be attached to features in an array and the array can be imaged to capture the chemiluminescent signals that are produced due to incorporation of a nucleotides at the features of the array. An image can be obtained after the array is treated with a particular nucleotide type (e.g. A, T, C or G). Images obtained after addition of each nucleotide type will differ with regard to which features in the array are detected. These differences in the image reflect the different sequence content of the features on the array. However, the relative locations of each feature will remain unchanged in the images. The images can be stored, processed and analyzed using the methods set forth herein. For example, images obtained after treatment of the array with each different nucleotide type can be handled in the same way as exemplified herein for images obtained from different detection channels for reversible terminator-based sequencing methods.

In another exemplary type of SBS, cycle sequencing is accomplished by stepwise addition of reversible terminator nucleotides containing, for example, a cleavable or photobleachable dye label as described, for example, in WO 04/018497 and U.S. Pat. No. 7,057,026. This approach is being commercialized by Solexa (now ILLUMINA® Inc.), and is also described in WO 91/06678 and WO 07/123,744. The availability of fluorescently-labeled terminators in which both the termination can be reversed and the fluorescent label cleaved facilitates efficient cyclic reversible termination (CRT) sequencing. Polymerases can also be co-engineered to efficiently incorporate and extend from these modified nucleotides.

In some reversible terminator-based sequencing embodiments, the labels do not substantially inhibit extension under SBS reaction conditions. However, the detection labels can be removable, for example, by cleavage or degradation. Images can be captured following incorporation of labels into arrayed nucleic acid features. In particular embodiments, each cycle involves simultaneous delivery of four different nucleotide types to the array and each nucleotide type has a spectrally distinct label. Four images can then be obtained, each using a detection channel that is selective for one of the four different labels. Alternatively, different nucleotide types can be added sequentially and an image of the array can be obtained between each addition step. In such embodiments, each image will show nucleic acid features that have incorporated nucleotides of a particular type. Different features will be present or absent in the different images due the different sequence content of each feature. However, the relative position of the features will remain unchanged in the images. Images obtained from such reversible terminator-SBS methods can be stored, processed and analyzed as set forth herein. Following the image capture step, labels can be removed and reversible terminator moieties can be removed for subsequent cycles of nucleotide addition and detection. Removal of the labels after they have been detected in a particular cycle and prior to a subsequent cycle can provide the advantage of reducing background signal and crosstalk between cycles. Examples of useful labels and removal methods are set forth herein.

In particular embodiments some or all of the nucleotide monomers can include reversible terminators. In such embodiments, reversible terminators/cleavable fluorophores can include fluorophores linked to the ribose moiety via a 3' ester linkage (Metzker, Genome Res. 15:1767-1776 (2005)). Other approaches have separated the terminator chemistry from the cleavage of the fluorescence label (Ruparel et al., Proc Natl Acad Sci USA 102: 5932-7 (2005)). Ruparel et al. described the development of reversible terminators that used a small 3' allyl group to block extension, but could easily be deblocked by a short treatment with a palladium catalyst. The fluorophore was attached to the base via a photocleavable linker that could easily be cleaved by a 30 second exposure to long wavelength UV light. Thus, either disulfide reduction or photocleavage can be used as a cleavable linker. Another approach to reversible termination is the use of natural termination that ensues after placement of a bulky dye on a dNTP. The presence of a charged bulky dye on the dNTP can act as an effective terminator through steric and/or electrostatic hindrance. The presence of one incorporation event prevents further incorporations unless the dye is removed. Cleavage of the dye removes the fluorophore and effectively reverses the termination. Examples of modified nucleotides are also described in U.S. Pat. Nos. 7,427,673, and 7,057,026.

Additional exemplary SBS systems and methods which can be used with the methods and systems described herein are described in U.S. Pub. Nos. 2007/0166705, 2006/0188901, 2006/0240439, 2006/0281109, 2012/0270305, and 2013/0260372, U.S. Pat. No. 7,057,026, PCT Publication No. WO 05/065814, U.S. Patent Application Publication No. 2005/0100900, and PCT Publication Nos. WO 06/064199 and WO 07/010,251.

Some embodiments can use detection of four different nucleotides using fewer than four different labels. For example, SBS can be performed using methods and systems described in the incorporated materials of U.S. Pub. No. 2013/0079232. As a first example, a pair of nucleotide types can be detected at the same wavelength, but distinguished based on a difference in intensity for one member of the pair compared to the other, or based on a change to one member of the pair (e.g. via chemical modification, photochemical modification or physical modification) that causes apparent signal to appear or disappear compared to the signal detected for the other member of the pair. As a second example, three of four different nucleotide types can be detected under particular conditions while a fourth nucleotide type lacks a label that is detectable under those conditions, or is minimally detected under those conditions (e.g., minimal detection due to background fluorescence, etc.). Incorporation of the first three nucleotide types into a nucleic acid can be determined based on presence of their respective signals and incorporation of the fourth nucleotide type into the nucleic acid can be determined based on absence or minimal detection of any signal. As a third example, one nucleotide type can include label(s) that are detected in two different channels, whereas other nucleotide types are detected in no more than one of the channels. The aforementioned three exemplary configurations are not considered mutually exclusive and can be used in various combinations. An exemplary embodiment that combines all three examples, is a fluorescent-based SBS method that uses a first nucleotide type that is detected in a first channel (e.g. dATP having a label that is detected in the first channel when excited by a first excitation wavelength), a second nucleotide type that is detected in a second channel (e.g. dCTP having a label that is detected in the second channel when excited by a second excitation wavelength), a third nucleotide type that is detected in both the first and the second channel (e.g. dTTP having at least one label that is detected in both channels when excited by the first and/or second excitation wavelength) and a fourth nucleotide type that lacks a label that is not, or minimally, detected in either channel (e.g. dGTP having no label).

Further, as described in U.S. Pub. No. 2013/0079232, sequencing data can be obtained using a single channel. In such so-called one-dye sequencing approaches, the first nucleotide type is labeled but the label is removed after the first image is generated, and the second nucleotide type is labeled only after a first image is generated. The third nucleotide type retains its label in both the first and second images, and the fourth nucleotide type remains unlabeled in both images.

Some embodiments can use sequencing by ligation techniques. Such techniques use DNA ligase to incorporate oligonucleotides and identify the incorporation of such oligonucleotides. The oligonucleotides typically have different labels that are correlated with the identity of a particular nucleotide in a sequence to which the oligonucleotides hybridize. As with other SBS methods, images can be obtained following treatment of an array of nucleic acid features with the labeled sequencing reagents. Each image will show nucleic acid features that have incorporated labels of a particular type. Different features will be present or absent in the different images due the different sequence content of each feature, but the relative position of the features will remain unchanged in the images. Images obtained from ligation-based sequencing methods can be stored, processed and analyzed as set forth herein. Exemplary SBS systems and methods which can be utilized with the methods and systems described herein are described in U.S. Pat. Nos. 6,969,488, 6,172,218, and 6,306,597.

Some embodiments can use nanopore sequencing (Deamer, D. W. & Akeson, M. "Nanopores and nucleic acids: prospects for ultrarapid sequencing." Trends Biotechnol. 18, 147-151 (2000); Deamer, D. and D. Branton, "Characterization of nucleic acids by nanopore analysis", Acc. Chem. Res. 35:817-825 (2002); Li, J., M. Gershow, D. Stein, E. Brandin, and J. A. Golovchenko, "DNA molecules and configurations in a solid-state nanopore microscope" Nat. Mater. 2:611-615 (2003)). In such embodiments, the asymmetric target nucleic acid passes through a nanopore. The nanopore can be a synthetic pore or biological membrane protein, such as α-hemolysin. As the asymmetric target nucleic acid passes through the nanopore, each base-pair can be identified by measuring fluctuations in the electrical conductance of the pore. (U.S. Pat. No. 7,001,792; Soni, G. V. & Meller, "A. Progress toward ultrafast DNA sequencing using solid-state nanopores." Clin. Chem. 53, 1996-2001 (2007); Healy, K. "Nanopore-based single-molecule DNA analysis." Nanomed. 2, 459-481 (2007); Cockroft, S. L., Chu, J., Amorin, M. & Ghadiri, M. R. "A single-molecule nanopore device detects DNA polymerase activity with single-nucleotide resolution." J. Am. Chem. Soc. 130, 818-820 (2008)). Data obtained from nanopore sequencing can be stored, processed and analyzed as set forth herein. In particular, the data can be treated as an image in accordance with the exemplary treatment of optical images and other images that is set forth herein.

Some embodiments can use methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides as described, for example, in U.S. Pat. Nos. 7,329,492 and 7,211,414, or nucleotide incorporations can be detected with zero-mode waveguides as described, for example, in U.S. Pat. No. 7,315,019, and using fluorescent nucleotide analogs and engineered polymerases as described, for example, in U.S. Pat. No. 7,405,281 and U.S. Pub. No. 2008/0108082. The illumination can be restricted to a zeptoliter-scale volume around a surface-tethered polymerase such that incorporation of fluorescently labeled nucleotides can be observed with low background (Levene, M. J. et al. "Zero-mode waveguides for single-molecule analysis at high concentrations." Science 299, 682-686 (2003); Lundquist, P. M. et al. "Parallel confocal detection of single molecules in real time." Opt. Lett. 33, 1026-1028 (2008); Korlach, J. et al. "Selective aluminum passivation for targeted immobilization of single DNA polymerase molecules in zero-mode waveguide nano structures." Proc. Natl. Acad. Sci. USA 105, 1176-1181 (2008)). Images obtained from such methods can be stored, processed and analyzed as set forth herein.

Some SBS embodiments include detection of a proton released upon incorporation of a nucleotide into an extension product. For example, sequencing based on detection of released protons can use an electrical detector and associated techniques that are commercially available from Ion Torrent (Guilford, CT, a Life Technologies subsidiary) or sequencing methods and systems described in U.S. Pub. Nos. 2009/0026082; 2009/0127589; 2010/0137143; and 2010/0282617. Methods set forth herein for amplifying target nucleic acids using kinetic exclusion can be readily applied to substrates used for detecting protons. More specifically, methods set forth herein can be used to produce clonal populations of amplicons that are used to detect protons.

The above SBS methods can be advantageously carried out in multiplex formats such that multiple different asymmetric target nucleic acids are manipulated simultaneously. In particular embodiments, different asymmetric target nucleic acids can be treated in a common reaction vessel or on a surface of a particular substrate. This allows convenient delivery of sequencing reagents, removal of unreacted reagents and detection of incorporation events in a multiplex manner. In embodiments using surface-bound target nucleic acids, the asymmetric target nucleic acids can be in an array format. In an array format, the asymmetric target nucleic acids can be typically bound to a surface in a spatially distinguishable manner. The asymmetric target nucleic acids can be bound by direct covalent attachment, attachment to a bead or other particle or binding to a polymerase or other molecule that is attached to the surface. The array can include a single copy of a asymmetric target nucleic acid at each site (also referred to as a feature) or multiple copies having the same sequence can be present at each site or feature. Multiple copies can be produced by amplification methods such as, bridge amplification or emulsion PCR as described in further detail herein.

The methods set forth herein can use arrays having features at any of a variety of densities including, for example, at least about 10 features/cm$^2$, 100 features/cm$^2$, 500 features/cm$^2$, 1,000 features/cm$^2$, 5,000 features/cm$^2$, 10,000 features/cm$^2$, 50,000 features/cm$^2$, 100,000 features/cm$^2$, 1,000,000 features/cm$^2$, 5,000,000 features/cm$^2$, or higher.

An advantage of the methods set forth herein is that they provide for rapid and efficient detection of a plurality of cm$^2$, in parallel. Accordingly, the present disclosure provides integrated systems capable of preparing and detecting nucleic acids using techniques known in the art such as those exemplified herein. Thus, an integrated system of the present disclosure can include fluidic components capable of delivering amplification reagents and/or sequencing reagents to one or more immobilized asymmetric target nucleic acids, the system including components such as pumps, valves, reservoirs, fluidic lines and the like. A flow cell can be configured and/or used in an integrated system for detection of target nucleic acids. Exemplary flow cells are described, for example, in U.S. Pat. Nos. 8,241,573 and 8,951,781. As exemplified for flow cells, one or more of the fluidic components of an integrated system can be used for an amplification method and for a detection method. Taking a nucleic acid sequencing embodiment as an example, one or more of the fluidic components of an integrated system can be used for an amplification method set forth herein and for the delivery of sequencing reagents in a sequencing method such as those exemplified above. Alternatively, an integrated system can include separate fluidic systems to carry out amplification methods and to carry out detection methods. Examples of integrated sequencing systems that are capable of creating amplified nucleic acids and also determining the sequence of the nucleic acids include, without limitation, the MISEQ™ platform (ILLUMINA®, Inc., San Diego, CA) and devices described in U.S. Pat. No. 8,951,781.

Compositions

During practice of the methods provided by the present disclosure several compositions can result. For example, a composition that includes a transposome complex and a lesion-intolerant DNA polymerase can result. The transposome can include a transposase bound to a transposon sequence that includes an adapter. The adapter can include one or more DNA lesion, one or more universal sequence, one or more index sequence, one or more UMI, or a combination thereof. The composition can further include target nucleic acids. Optionally, the composition can include a lesion-tolerant DNA polymerase.

In another embodiment, a composition can result that has a plurality of single stranded modified target nucleic acids, a primer, and a lesion-intolerant DNA polymerase. For instance, the target nucleic acids can include, from 5' to 3', a first adapter, a target nucleic acid, and the complement of the first adapter. The first adapter can include one or more DNA lesion, one or more universal sequence, one or more index sequence, one or more UMI, or a combination thereof. In one embodiment, a universal sequence can include a transposase recognition site. The primer can include, from 5' to 3', a second adapter and a nucleotide sequence that anneals to the complement of the first adapter. The second adapter can include one or more universal sequence, one or more index sequence, one or more UMI, or a combination thereof. The primer can optionally include a blocked 3' end, and can optionally include at least one altered nucleotide. In one embodiment, the primer is annealed to single stranded modified target nucleic acids.

In another embodiment, a composition includes transposome complex. The transposome complex includes, but is not limited to, a transposase and a transposon. In one embodiment, the transposon includes an adapter. The adapter can include, for example, a first strand having, from 5' to 3' at least one universal sequence, at least one index sequence, at least one UMI, or a combination thereof, a DNA lesion, and a transposase recognition sequence. In one embodiment, the transposase recognition sequence includes a mosaic element. The adapter can include, for example, a second strand that has nucleotides complementary to at least a portion of the transposase recognition sequence. In one embodiment, the first strand also includes a capture agent at the 5' end, or the second strand also includes a capture agent at the 3' end. In one embodiment, a cleavable linker is located between capture agent and the 5' end of the first strand. In one embodiment, a cleavable linker is located between capture agent and the 3' end of the second strand. In one embodiment the composition further includes a solid surface, where the transposase complex is attached to the solid surface. In another embodiment the composition further includes a solid surface, where the transposon is not associated with the transposase and the transposon is attached to the solid surface.

Kits

The present disclosure also provides kits for practicing one more aspects the methods provided herein. A kit can be used for producing libraries of target nucleic acids. In one embodiment, the kit can be used for producing libraries of symmetric target nucleic acids. The kit can include in separate containers a transposome complex and a lesion-intolerant DNA polymerase. The transposome can include a transposase bound to a transposon sequence, where the transposon sequence includes an adapter and a DNA lesion. In one embodiment, the kit can be used for converting symmetric libraries to asymmetric libraries. In this embodiment the kit can further include a primer. In one embodiment, the primer includes from 5' to 3' a second adapter and a nucleotide sequence that anneals to the complement of the first adapter.

A kit's components can be present in a suitable packaging material in an amount sufficient for producing at least one library. Optionally, other reagents such as a buffer solution (either prepared or present in its constituent components, where one or more of the components may be premixed or all of the components may be separate), and the like, are also included. Instructions for use of the packaged polypeptide or primer pair are also typically included.

As used herein, the phrase "packaging material" refers to one or more physical structures used to house the contents of the kit. The packaging material is constructed by known methods, preferably to provide a sterile, contaminant-free environment. The packaging material has a label which indicates that the components can be used for library production. In addition, the packaging material contains instructions indicating how the materials within the kit are employed for practicing one more aspects the methods provided herein. As used herein, the term "package" refers to a solid matrix or material such as glass, plastic, paper, foil, and the like, capable of holding within fixed limits one or more components of the kit. "Instructions for use" typically include a tangible expression describing the reagent concentration or at least one assay method parameter, such as the relative amounts of reagent and sample to be admixed, maintenance time periods for reagent/sample admixtures, temperature, buffer conditions, and the like.

The invention is defined in the claims. However, below there is provided a non-exhaustive listing of non-limiting exemplary aspects. Any one or more of the features of these aspects may be combined with any one or more features of another example, embodiment, or aspect described herein.

EXEMPLARY ASPECTS

Aspect 1 is a method for producing a sequencing library comprising:
providing a plurality of symmetric modified target nucleic acids comprising a first adapter sequence at each end, wherein the first adapter sequence comprises a DNA lesion;
extending the modified target nucleic acids with a lesion-intolerant polymerase to generate a plurality of asymmetric modified target nucleic acids comprising at the 5' end of each strand the first adapter sequence and at the 3' end of each strand the complement of a portion of the first adapter.

Aspect 2 is the method of Aspect 1, wherein the plurality of symmetric modified target nucleic acids are double stranded and each strand comprises, from 5' to 3', the first adapter sequence comprising the DNA lesion, the target nucleic acid, a gap comprising at least one nucleotide, and the complement of the first adapter sequence without the DNA lesion.

Aspect 3 is the method of Aspect 1 or 2, wherein the extending initiates at the gap.

Aspect 4 is the method of any one of Aspects 2-3, further comprising:
annealing a primer to the plurality of asymmetric modified target nucleic acids, the primer comprising from 5' to 3' a second adapter sequence and an annealing domain, the annealing domain comprising a nucleotide sequence that anneals to the complement of the portion of the first adapter of the plurality of asymmetric modified target nucleic acids;
extending the 3' end of the annealed asymmetric modified target nucleic acids with a lesion-intolerant polymerase, wherein the extending results in a plurality of asymmetric modified target nucleic acids comprising from 5' to 3' (i) the first adapter, (ii) the target nucleic acid, (iii) the complement of the portion of the first adapter, and (iv) the complement of the second adapter.

Aspect 5 is the method of any one of Aspects 1-4, wherein the extending the 3' end of the annealed asymmetric modified target nucleic acids is repeated at least 3 times.

Aspect 6 is the method of any one of Aspects 1-5, wherein the DNA lesion comprises at least one of an abasic site, a modified base, a mismatch, a single-stranded break, or cross-linked nucleotides.

Aspect 7 is the method of any one of Aspects 1-6, wherein the DNA lesion comprises at least one uracil.

Aspect 8 is the method of any one of Aspects 1-7, wherein the annealing domain of the primer comprises at least one altered nucleotide that increases the melting temperature compared to the corresponding native DNA nucleotide.

Aspect 9 is the method of any one of Aspects 1-8, wherein the altered nucleotide comprises a locked nucleic acid, PNA, or RNA.

Aspect 10 is the method of any one of Aspects 1-9, wherein the 3' end of the primer is blocked.

Aspect 11 is the method of any one of Aspects 1-10, wherein the first adapter comprises one or more universal sequences, one or more index sequences, one or more universal molecular identifiers, or a combination thereof.

Aspect 12 is the method of any one of Aspects 1-11, wherein at least one of the one or more universal sequences, one or more index sequences, and one or more universal molecular identifiers is located in the adapter between the DNA lesion and the end of the adapter distal to the target nucleic acid.

Aspect 13 is the method of any one of Aspects 1-12, wherein the second adapter comprises one or more universal sequences, one or more index sequences, one or more universal molecular identifiers, or a combination thereof.

Aspect 14 is the method of any one of Aspects 1-13, wherein the one or more universal sequences, one or more index sequences, and one or more universal molecular identifiers of the first adapter are unique compared to the one or more universal sequences, one or more index sequences, and one or more universal molecular identifiers of the second adapter.

Aspect 15 is the method of any one of Aspects 1-14, wherein the one or more index sequences of the first adapter are compartment specific.

Aspect 16 is the method of any one of Aspects 1-15, wherein the one or more index sequences of the second adapter are compartment specific.

Aspect 17. The method of any one of Aspects 1-16, wherein the first adapter comprises a transposase recognition site.

Aspect 18 is the method of any one of Aspects 1-17, wherein the target nucleic acids are from nucleic acids originating from a single cell.

Aspect 19 is the method of any one of Aspects 1-18, wherein the target nucleic acids are from nucleic acids originating from a plurality of cells.

Aspect 20 is the method of any one of Aspects 1-19, wherein the target nucleic acids originating from a single cell or a plurality of cells comprise RNA.

Aspect 21 is the method of any one of Aspects 1-20, wherein the RNA comprises mRNA.

Aspect 22 is the method of any one of Aspects 1-21, wherein the target nucleic acids originating from a single cell or a plurality of cells comprise DNA.

Aspect 23 is the method of any one of Aspects 1-22, wherein the DNA comprises whole cell genomic DNA.

Aspect 24 is the method of any one of Aspects 1-23, wherein the whole cell genomic DNA comprises nucleosomes.

Aspect 25 is the method of any one of Aspects 1-247, wherein the target nucleic acids are from nucleic acids originating from cell free DNA.

Aspect 26 is the method of any one of Aspects 1-25, wherein the method comprises combinatorial indexing.

Aspect 27 is the method of any one of Aspects 1-26, further comprising amplifying the asymmetric modified target nucleic acids, wherein the amplifying comprises a second primer and a lesion-tolerant polymerase, and wherein the second primer comprises a nucleotide sequence that anneals to the first adapter sequence or the complement thereof.

Aspect 28 is the method of any one of Aspects 1-27, wherein the second primer further comprises one or more universal sequences, one or more index sequences, one or more universal molecular identifiers, or a combination thereof.

Aspect 29 is the method of any one of Aspects 1-28, wherein the one or more universal sequences, one or more index sequences, and one or more universal molecular identifiers of the second primer are unique compared to the one or more universal sequences, one or more index sequences, and one or more universal molecular identifiers of the first adapter and the second adapter.

Aspect 30 is the method of any one of Aspects 1-29, wherein subsets of the plurality of asymmetric modified target nucleic acids are present in a plurality of compartments, and wherein either (i) the first adapter comprises a first compartment specific index, (ii) the second adapter comprises a second compartment specific index, or both (i) and (ii).

Aspect 31. The method of any one of Aspects 1-30, further comprising combining the asymmetric modified target nucleic acids from different compartments to generate pooled indexed asymmetric modified target nucleic acids.

Aspect 32 is the method of any one of Aspects 1-31, further comprising distributing subsets of the pooled indexed asymmetric modified target nucleic acids into a second plurality of compartments and modifying the indexed asymmetric modified target nucleic acids, wherein the modifying comprises adding to the indexed asymmetric modified target nucleic acids present in each subset an additional compartment specific index sequence to result in indexed DNA nucleic acids, and wherein the modifying comprises ligation or extension.

Aspect 33 is the method of any one of Aspects 1-32, wherein the compartments comprise a well or a droplet.

Aspect 34 is the method of any one of Aspects 1-33, wherein the providing comprises contacting a plurality of DNA fragments with the first adapter under conditions to ligate the first adapter to both ends of the DNA fragments.

Aspect 35 is the method of any one of Aspects 1-34, wherein the DNA fragments are double stranded and blunt-ended.

Aspect 36 is the method of any one of Aspects 1-35, wherein the first adapter is a double stranded DNA oligonucleotide.

Aspect 37 is the method of any one of Aspects 1-36, wherein one 3' end of the first adapter is blocked.

Aspect 38 is the method of any one of Aspects 1-37, wherein the DNA fragments are double stranded and comprise a single stranded region at one or both 3' ends.

Aspect 39 is the method of any one of Aspects 1-38, wherein the first adapter is a double stranded DNA oligonucleotide comprising a single stranded region at one end, wherein the single stranded region can anneal to the single stranded region present on the DNA fragments.

Aspect 40 is the method of any one of Aspects 1-38, wherein the adapter is a forked adapter.

Aspect 41 is the method of any one of Aspects 1-40, wherein the providing comprises contacting DNA with a transposome complex, wherein the transposome complex comprises a transposase and the first adapter, wherein the contacting occurs under conditions suitable for ligation of the first adapter into the DNA to generate the symmetric modified target nucleic acids. In one Aspect, the transposome complex is the transposome complex of any one of Aspects 67-71.

Aspect 42 is the method of any one of Aspects 1-41, wherein the generated symmetric modified target nucleic acids comprise a gap of at least one nucleotide in one strand the between the ligated first adapter and the target nucleic acid.

Aspect 43 is the method of any one of Aspects 1-42, wherein the DNA is present in a plurality of compartments, and wherein the first adapter in each compartment comprises a compartment specific index.

Aspect 44 is the method of any one of Aspects 1-43, further comprising combining the single stranded modified target nucleic acids from different compartments to generate pooled symmetric modified target nucleic acids, and distributing the symmetric modified target nucleic acids into a second plurality of compartments.

Aspect 45 is the method of any one of Aspects 1-44, wherein the method further comprises fragmentation of the whole cell genomic DNA.

Aspect 46 is the method of any one of Aspects 1-45, wherein the fragmentation comprises digestion of the whole cell genomic DNA with a restriction endonuclease.

Aspect 47 is the method of any one of Aspects 1-46, wherein the fragmented DNA is subjected to proximity ligation to join chimeric target nucleic acids.

Aspect 48 is the method of any one of Aspects 1-47, wherein the cytosine residues of an adapter are replaced with 5-methylcytosine.

Aspect 49 is the method of any one of Aspects 1-48, wherein the symmetric or asymmetric target nucleic acids are subjected to chemical or enzymatic methylation conversion.

Aspect 50 is the method of any one of Aspects 1-49, wherein the providing comprises fixing isolated nuclei, subjecting the isolated nuclei to conditions to dissociate nucleosomes from genomic DNA, fragmenting the genomic DNA, subjecting the fragments to proximity ligation to join chimeric target nucleic acids, and contacting the ligated fragments to a transposome complex, wherein the transposome complex comprises a transposase and the first adapter, wherein the contacting occurs under conditions suitable for ligation of the first adapter into the DNA to generate the symmetric modified target nucleic acids.

Aspect 51 is the method of any one of Aspects 1-50, wherein the fragmenting comprises digestion with a restriction endonuclease.

Aspect 52 is the method of any one of Aspect 1-51, further comprising:

provinding a surface comprising a plurality of amplification sites, wherein the amplification sites comprise at least two populations of attached single stranded capture oligonucleotides having a free 3' end, and contacting the surface comprising amplification sites with the plurality of asymmetric modified target nucleic acids under conditions suitable to produce a plurality of amplification sites that each comprise a clonal population of amplicons from an individual asymmetric modified target nucleic acid.

Aspect 53 is a composition comprising a transposome complex and a DNA polymerase, wherein the transposome comprises a transposase bound to a transposon sequence, wherein the transposon sequence comprises an adapter and a DNA lesion, and wherein the DNA polymerase is a lesion-intolerant polymerase.

Aspect 54 is the composition of Aspect 53, wherein the adapter comprises one or more universal sequence, one or more index sequence, one or more UMI, or a combination thereof.

Aspect 55 is the composition of Aspect 53 or 54, further comprising a lesion-tolerant DNA polymerase.

Aspect 56 is a composition comprising a plurality of modified target nucleic acids comprising 5' to 3' a first adapter comprising a DNA lesion, a target nucleic acid, and the complement of the first adapter;

a primer comprising from 5' to 3' a second adapter; and an annealing domain, the annealing domain comprising a nucleotide sequence that anneals to the complement of the first adapter;

a lesion-intolerant DNA polymerase.

Aspect 57 is the composition of Aspect 56, wherein the primer comprises at least one altered nucleotide that increases the melting temperature compared to the corresponding native DNA nucleotide.

Aspect 58 is the composition of Aspect 56 or 57, wherein the primer is annealed to target nucleic acids.

Aspect 59 is the composition of any one of Aspects 56-58, wherein the 3' end of the primer is blocked.

Aspect 60 is the composition of any one of Aspects 56-59, wherein the first adapter comprises a transposase recognition site.

Aspect 61 is a kit comprising in separate containers a transposome complex and a DNA polymerase, wherein the transposome comprises a transposase bound to a transposon sequence, wherein the transposon sequence comprises a first adapter and a DNA lesion, and wherein the DNA polymerase is a lesion-intolerant polymerase; and instructions for use.

Aspect 62 is the kit of Aspect 61, further comprising a second DNA polymerase, wherein the second DNA polymerase is a lesion-tolerant polymerase.

Aspect 63 is the kit of Aspect 61 or 62, further comprising a primer, wherein the primer comprises from 5' to 3' a second adapter and an annealing domain, the annealing domain comprising a nucleotide sequence that anneals to the complement of the first adapter.

Aspect 64 is the kit of any one of Aspects 61-63, wherein the 3' end of the primer is blocked.

Aspect 65 is the kit of any one of Aspects 61-64, wherein the first adapter comprises one or more of a universal sequence, one or more of an index sequence, one or more of a UMI, or a combination thereof.

Aspect 66 is the kit of any one of Aspects 61-65, wherein the second adapter primer further comprises one or more of a universal sequence, one or more of an index sequence, one or more of a UMI, or a combination thereof.

Aspect 67 is a transposome complex comprising: a transposase; and a transposon comprising a nucleic acid comprising an adapter comprising on a first strand, from 5' to 3', at least one universal sequence, at least one index sequence, at least one UMI, or a combination thereof, a DNA lesion, and a transposase recognition sequence, and on a second strand nucleotides complementary to at least a portion of the transposase recognition sequence.

Aspect 68 is the transposome complex of Aspect 67, wherein the first strand further comprises a capture agent at the 5' end of the first strand.

Aspect 69 is the transposome complex of Aspect 67 or 68, wherein the first strand further comprises a cleavable linker located between capture agent and the 5' end.

Aspect 70 is the transposome complex of any one of Aspects 67-69, wherein the second strand further comprises a capture agent at the 3' end of the second strand.

Aspect 71 is the transposome complex of any one of claim Aspects 70, wherein the second strand further comprises a cleavable linker located between capture agent and the 3' end.

EXAMPLES

The present disclosure is illustrated by the following examples. It is to be understood that the particular examples, materials, amounts, and procedures are to be interpreted broadly in accordance with the scope and spirit of the disclosure as set forth herein.

Example 1

Proof-of-Concept of Conversion of Symmetric Target Nucleic Acids to Asymmetric Target Nucleic Acid Fragments.

Experimental approach to producing symmetric target nucleic acids with tagmentation and conversion to asymmetric target nucleic acids. Sequencing libraries were prepared by tagmentation of DNA using a transposome complex with a single transposon to produce target nucleic acids having the same adapter at each end, and then exposed to conditions to modify one of the adapters to result in asymmetric target nucleic acids.

Protocol for Cell/Nuclei.

Kit includes: 96 well indexed TSM plate, 384 well indexed PCR plate, 5× Tagmentation buffer TB1, ExTB (500 ul in 1.7 ml screw cap tube, LNA+TX100), Post tagmentation wash buffer (10 ml in 15 ml conical tube), Resuspension buffer (RSB) (10 ml in 15 ml conical tube), and 0.5% SDS (500 ul in 1.7 ml screw cap tube).

Prepared by user: Q5 2× master mix (NEB, M0492L), Q5U 2× mater mix (NEB, M0597L), 80% EtOH, and AMPure XP beads (Beckman Coulter, A63880).

Equipment and consumable plastics: Cell Counter (ThermoFisher Countess II FL Automated Cell Counter, AMQAF1000), Countess Cell Counting Chamber Slides (ThermoFisher, PN C10228), Centrifuge for plates with temperature control, Benchtop centrifuge with temperature control, Bioanalyzer (Agilent, PN G2939BA), Agilent High Sensitivity DNA kit (5067-4626), 96 well plate (Eppendorf twin.tec PCR Plate 96 LoBind, skirted, PN 0030129512), 384 well plate (Eppendorf twin.tec PCR Plate 384 LoBind, skirted, PN 0030129547), Disposable reagent reservoir (VWR, PN 89094-658) or similar, Magnetic stand for beads collection, Thermal cycler for 96 and 384 well plate, Plate Shaker, and Falcon 15 mL collection tube (ThermoFisher, PN 14-959-53A or SARSTEDT, PN 62.554.205)

Reagents for nuclei preparation: Pierce™ 16% Formaldehyde (w/v), Methanol-free (ThermoFisher, PN 28906), TryPLE (Fisher Scientific, PN 12-604-039), PBS buffer (Sigma, PN #806552-1L), Pierce Protease Inhibitor Mini Tablets, EDTA-free (PN A32955), and Trypan Blue Solution (ThermoFisher, PN 15250061).

Buffers recommended for cell lines. Lysis buffer is 10 mM HEPES, 10 mM NaCl, 3 mM MgCl2, 0.1% Igepal, 0.1% Tween, and protease inhibitor. NIB Buffer is 10 mM Tris (pH 7.5), 10 mM NaCl, 3 mM MgCl2, 0.1% Tween, and protease inhibitor. 10× Xlink buffer is 5M NaCl, 1M Tris HCl (pH 7.5), 1M MgCl2 and 100 ng/uL BSA.

Nuclei Preparation & Nucleosome Depletion. Cells were plated at 1×10⁶ in T25 flask (PN) the day prior and were sub confluent at time of harvest. Cells were washed in flask with 5 mL of ice-cold PBS, trypsinzed with TrypLE (1 mL at 37° C. for 5 min), collected by spinning at 500 rcf for 3 min at 4° C., and washed in 1 mL ice cold PBS and proceeded to nuclei isolation.

Nuclei Isolation. Cells were spun down at 500 rcf for 3 min at 4° C., resuspend in 1 mL Lysis buffer, and incubated on ice for 10 min. Cells were spun down at 500 rcf for 3 min at 4° C., and resuspended in 300 uL Lysis buffer. Nuclei were counted using 1:5 dilution (2 uL sample+8 uL Lysis buffer+10 uL Trypan blue solution). 1×10⁶ were aliquoted for fixation.

Nuclei Fixation. Volume was increased up to 5 mL Lysis buffer, 246 μL of 16% formaldehyde from freshly opened ampule added (0.75% formaldehyde total, range of 0.5%-0.75% is acceptable). Incubated at room temp for 10 minutes with gentle shaking, centrifuged at 500 rcf for 3 minutes at 4° C. to pellet, washed in 1 mL of ice cold NIB, spun at 500 rcf for 3 minutes at 4° C., and washed with 200 uL 1× Xlink buffer (ice cold). During wash, nuclei were transferred to 1.5 mL tube for better pellets and spun at 500 rcf for 3 minutes at 4° C.

Nucleosome Depletion (for Whole Genome Sequencing). Pellet resuspended in 760 μL 1× Xlink buffer with 40 μL of 1% SDS and incubated at 37° C. with shaking (400 rpm) for 20 minutes. (0.05% final SDS), spun at 500 rcf for 3 minutes at 4° C., washed with 200 uL 1×NIB, spun at 500 rcf for 3 minutes at 4° C., and resuspend in 50-100 μL of NIB. A 2 uL sample was added 8 uL NIB and 10 uL trypan blue and loaded 10 uL on Cell Counter. The nuclei were concentrated or diluted as needed to 500 nuclei/ul for pipetting out.

Figure 10:
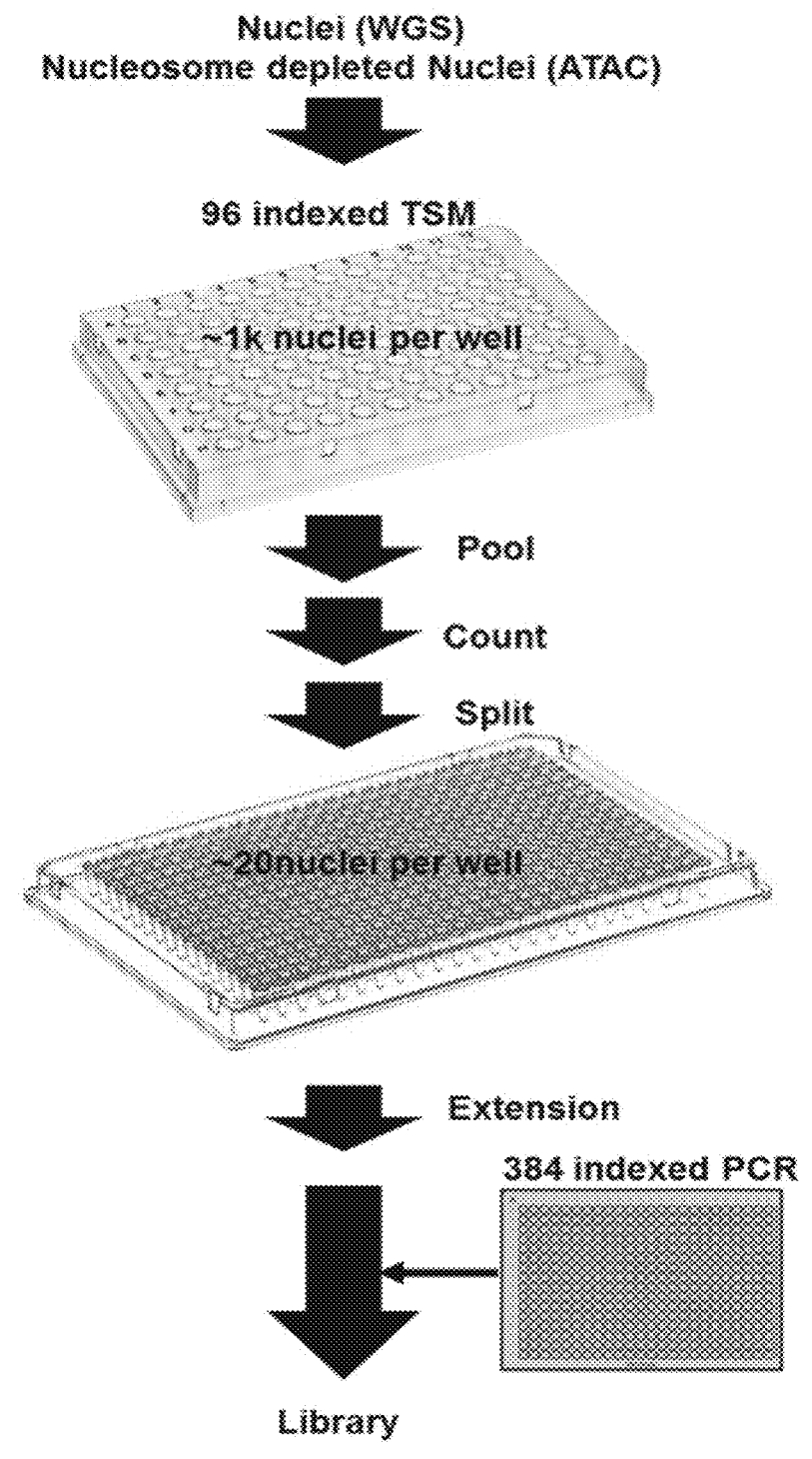
FIG. 10 shows schematic drawings of an embodiment of a protocol for plate-based combinatorial indexing.

Protocol for Plate Based Combinatorial Indexing Workflow (FIG. 10).

Tagmentation. Mix nuclei with buffer: 350 ul (~100K) nuclei, 500 ul 5× Tagmentation buffer (TB1), and 1350 ul H2O. Add 20 ul in each well of 96 TSM plate, and incubate 15 min at 55° C. on thermal cycler. Add 100 ul 200 mM EDTA into a 15 mL collection tube and pool the nuclei from 96 well plate into the 15 mL collection tube on ice (total 25 ulx96+100 ul=2.5 ml). Pellet the nuclei at 500 rcf at 4° C., and resuspend nuclei in wash buffer 500 ul. Determine the concentration of nuclei by removing a 2 uL sample, adding 8 uL NIB and 10 uL trypan blue, and loading 10 uL on Cell Counter. The nuclei are then diluted to nuclei/uL, and 4 uL are loaded into each well of the plate.

Extension: Add reagents in the following order below: add 1 ul 0.5% SDS, heat 10 min at 55° C., add 2 ul ExTB, add 7 ul 2×Q5 master mix (NEB) for a total of 14 ul. Mix well and run program on thermocycler: 1. 72° C. for 10 min, 2. 98° C. for 30 s, 3. 98° C. for 10 s, 4. 59° C. for 20 s, 5. 72° C. for 10 s, 6. repeat steps 3-5 for a total of 10 cycles, 7. 72° C. for 2 min and 8. 10° C. holding temperature.

Indexed PCR: Transfer 1 ul PCR primers from 384 well PCR plate to nuclei plate from the extension. Add 15 ul 2×NEB Q5U, and PCR program on thermal cycler: 1. 98° C. for 30 s, 2. 98° C. for 10 s, 3. 55° C. for 20 s, 4. 72° C. for 30 s, 5. repeat steps 2-4 for a total of 20 cycles, 6. 72° C. for 2 min, and 7. 10° C. holding temperature. Libraries usually amplify between 12-14 cycles.

Library Clean up: Pool 10 ul per well; total 3840 ul to a 15 mL collection tube (PN), run through QIAGEN® PCR cleanup column (PN) to concentrate, elute in 50 ul, add 50 ul AMPURE® XP beads, wash twice by 100 ul 80% EtOH, elute in 20 ul RSB, and quantify by Bioanalyzer DNA HS kit (PN).

AA→AB (Symmetric to Asymmetric) Protocol for Genomic DNA (gDNA).

Tnp assembly: add 5 ul 10× Annealing buffer, 5 ul SBS12-U-ME (Mosaic Element) 100 uM, 5 ul ME' 100 uM, and 35 ul H2O for 50 ul total. Run on thermocycler: 95° C. for 1 min, 80° C. for 30 sec, decrease by 1° C. every cycle to 20° C., 20° C. for 1 hour, 10° C. holding temperature.

TSM assembly: add 79 ul SDB buffer, 1 ul Tn5 200 uM, and 20 ul Tnp from Tnp assembly for 100 ul total. Incubate at 37° C. overnight, and dilute 4× in SDB buffer to 500 uM TSM.

Tagmentation on gDNA: add 4 ul gDNA 20 ng, 5 ul 2×TD buffer (tagmenation buffer), and 1 ul TSM from TSM assembly for 10 ul total, and incubate at 55° C. for 10 min.

AA→AB conversion: add 1 ul 1% SDS, incubate at 55° C. for 10 min, add 2 ul 10% Triton-X100 mixed with 1 uM LNA-ME_A14 oligo, add 2 ul 2×NPM master mix (ILLU-MINA®) for 15 ul total. Run on thermocycler: 1. 72° C. for 10 min, 2. 98° C. for 30 s, 3. 98° C. for 10 s, 4. 59° C. for 20 s, 5. 72° C. for 10 s, 6. repeat steps 3-5 for a total of 10 cycles, 7. 72° C. for 2 min, and 8. 10° C. holding temperature.

PCR: add 1 ul SBS12 25 uM, 1 ul A14 25 uM, 8 ul $H_2O$, and 25 ul 2×NEB Q5U master mix for 50 ul total. Run on thermocycler: 1. 98° C. for 30 s, 2. 98° C. for 10 s, 3. 55° C. for 20 s, 4. 72° C. for 30 s, 5. repeat steps 2-4 for a total of 20 cycles, 6. 72° C. for 2 min, and 7. 10° C. holding temperature. Libraries usually amplify between 12-14 cycles. The library can be checked by loading 5 ul PCR product on 1.2% Lonza agrose gel and resolving product with 180 v for 15 min.

Effect of Size of DNA Lesion.

Figure 11:
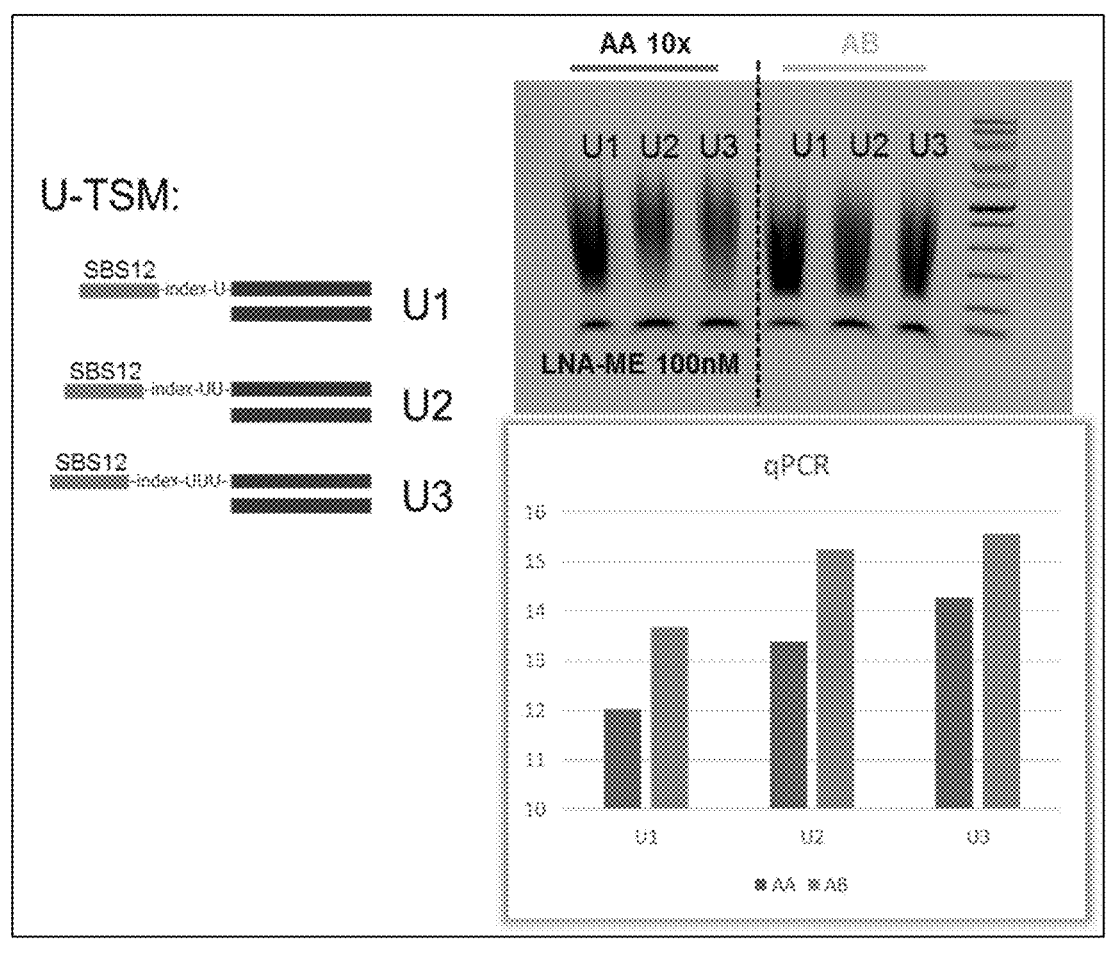
FIG. 11 shows the effect of the size of DNA lesion on library generation.

Proof-of-concept data of the AA→AB approach on gDNA. Three different TSMs containing different numbers of uracils as the DNA lesion, U, UU, or UUU between ME and index, were tested. The $1^{st}$ extension was repeated 10 times. All TSMs were functional and generated libraries albeit at different efficiency, with a single U the most efficient (FIG. 11). AB system was compared as the control, in which SBS12-ME TSM was mixed with TSM loaded with A14-ME. By qPCR AA→AB systems increased the template ~4× compared to standard AB system. LNA-ME concentration titration (data not shown here) shows 100 nM is efficient for the $2^{nd}$ extension.

Effect of Altered Nucleotides on Extension to Add Adapter.

Data demonstrating that standard A14-ME oligo (no locked nucleic acids (LNA) present in the primer) performed poorly in the AA→AB conversion. AB system with SBS12-ME and A14-ME TSMs was compared as the control (FIG. 12). Instead of LNA-A14, the oligo made of normal bases was applied for the $2^{nd}$ extension. The final library yield by PCR was significantly reduced and showing a broad smear compared to FIG. 11.

LNA-ME enhances the $2^{nd}$ extension. Increasing the number of cycles for LNA-ME extensions enhanced the yield, with 10 cycles reaching almost the theoretical maximum (FIG. 13). The difference between poor library generation with the standard A14-ME oligo (no LNA) compared to almost complete library conversion using a modified A14-ME oligo with LNA modification was surprising and unexpected and a significant advantage. Additionally, the 2-fold yield difference between AA→AB and AB system indicates that almost complete maximum conversion was obtained.

Effect of Annealing Temperature.

Figure 14:
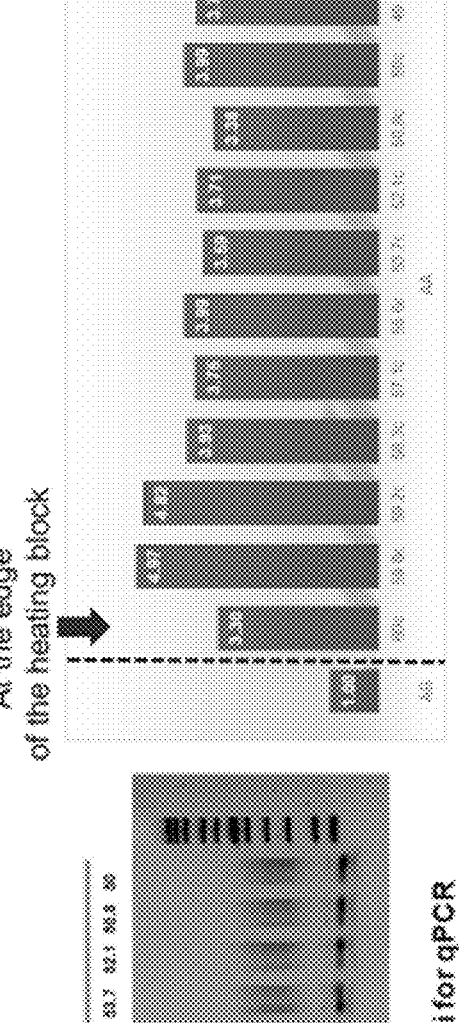
FIG. 14 shows the effect of annealing temperature.

LNA-ME annealing temperature titration on nuclei ATAC bulk assay. AB system containing SBS12 and A14 ME was used as a control. The genomic DNA inside the same number of nuclei was transposed by TSMs. The 2nd extension of the AA→AB workflow was carried on different annealing temperatures. ~59.5° C. showed the optimal efficiency and the amplifiable template could be enhanced ~5 fold according to qPCR compared to AB control (FIG. 14).

Example 2

Improved Single-Cell Combinatorial Indexing

A primary challenge of single-cell omics is the efficient conversion of the genomic property for each cell into a sequencing library. Here, we describe an adapter-switching strategy for single-cell combinatorial indexing workflows (sci) that is generalizable to multiple assays and does not require custom sequencing chemistry. This technique, symmetrical strand sci (s3), provides one-to-two order-of-magnitude improvements in reads obtained per cell for a variety of properties including chromatin accessibility (s3-ATAC), whole-genome sequencing (s3-WGS), and genome plus chromatin conformation (s3-GCC).

Main

Single-cell genomics assays have quickly become a dominant platform for interrogating complex biological systems across the spectrum of life science disciplines. Platforms to capture various properties at the single-cell level typically suffer a tradeoff between cell throughput and the depth of information that can be obtained per cell. We and others have described workflows that utilize single-cell combinatorial indexing (sci)[1] that leverages transposase-based library construction[2] to assess a variety of genomic properties in high throughput. While the transposition reaction itself (tagmentation) is highly efficient, viable sequencing library molecules are only produced when different adaptors, in the form of forward or reverse primary sequences, are incorporated at each end of the molecule. During the tagmentation reaction, there is an equal probability of incorporating each of the two sequences, thus resulting in half of the molecules being forward-forward or reverse-reverse adaptor combinations; reducing the theoretical yield to 50%. To combat this inefficiency, several strategies have been developed including the use of a larger complement of adaptor species[3], the incorporation of a T7 promoter sequence to go through an RNA intermediate[4-6], or incorporation of a second adaptor using targeted[7] or random priming[8]. Here, we present an alternative strategy that utilizes adapter replacement to produce library molecules tagged with both forward and reverse adaptors for both the top and bottom strand. Additionally, this format permits the use of a DNA index sequence embedded within the transposase adaptor complex, enabling single-cell combinatorial indexing (sci) applications, where two rounds of indexing are performed—the first at the transposition stage, and second at the PCR stage[1,9,10].

This technology, symmetrical strand sci (s3), leverages the efficiency of single-adaptor transposition to incorporate the forward primer sequence in addition to the universal mosaic end sequence and a compartment-specific DNA barcode. The adaptor is designed such that a uracil base is present immediately following the transposase recognition sequence (mosaic end) on the top strand of the resulting product, which is covalently incorporated during the tagmentation reaction. Polymerase extension with a uracil-intolerant enzyme results in the copying of the mosaic end sequence on the bottom strand without extension into the DNA barcode or forward primer sequence. Subsequent denaturation and addition of a mosaic end locked nucleic acid (LNA) template that contains the reverse primer sequence along with a uracil-tolerant polymerase enables the extension of the library molecule to incorporate the additional sequence. To ensure maximum efficiency, the template oligonucleotide is blocked from extension to prevent its action as a primer and to enable multiple rounds of the linear extension reaction to be carried out (FIG. 7). An additional advantage the s3 platform is that the adaptor sequences are designed such that standard sequencing recipes can be used instead of custom workflows and primers that are required for sci technologies. We demonstrate this workflow to produce single-cell chromatin accessibility libraries (s3-ATAC) with an improvement in the median passing reads per cell of 16-fold, single-cell whole genome sequencing (s3-WGS) with an improvement over our previous SCI-seq/ sci-DNA-seq[11] of 126-fold, and a new technique that captures both genome sequence and chromatin conformation information in single-cells (s3-GCC), with higher rates of chromatin interaction signal than previous combinatorial indexing Hi-C methods[12].

Figure 15:
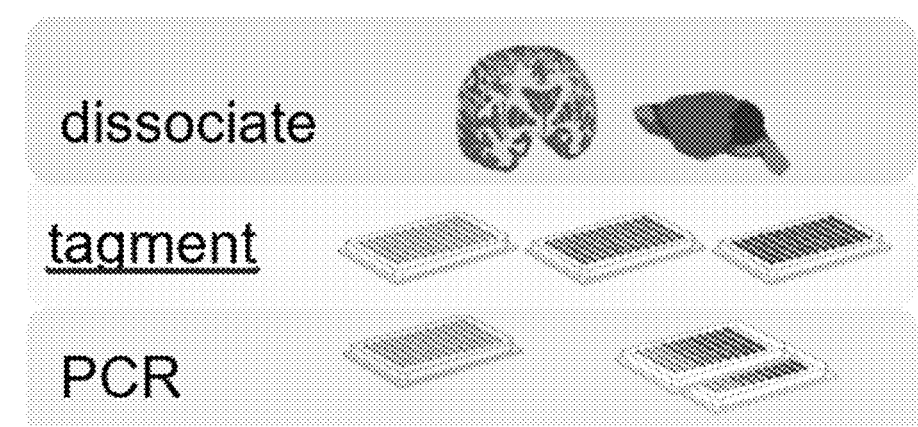
FIG. 15 shows experimental layout of barnyard experiment showing indexing at both tagmentation and PCR stages for multiple 96-well plates using nuclei sourced from flash frozen human cortical and mouse whole brain samples.
Figure 16:
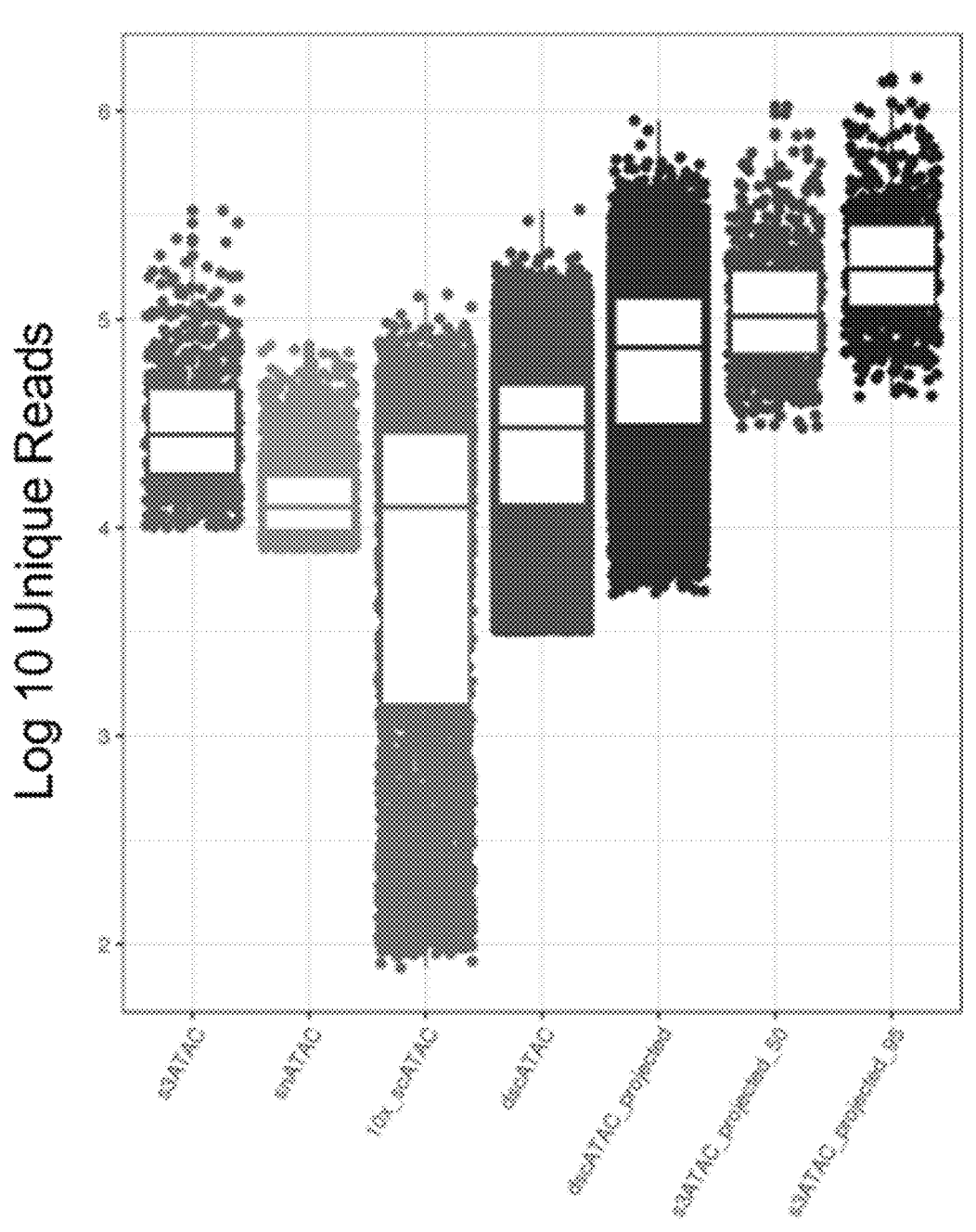
FIG. 16 shows a boxplot of library complexity as measured by unique reads per cell. s3ATAC outperforms all other published single-cell ATAC seq libraries on flash frozen mouse cortex, based on projected unique library molecules.

We first sought to establish the s3 technique to assess chromatin accessibility due to the minimal pre-processing of nuclei prior to the novel components of the technique. In s3-ATAC nuclei are isolated and then tagmented, as in traditional sci-ATAC-seq, but instead using our single-ended, indexed transposomes and then carried through the adaptor-switching s3 workflow (FIG. 7). To ensure we attain true single-cell libraries without genomic contamination from other nuclei and minimal barcode collisions, we performed a mixed-species experiment, also known as a "barnyard" test on primary frozen human cortical tissue and frozen mouse whole brain tissue FIG. 15. We elected to perform this test on primary tissue samples instead of in an idealized cell line setting to more accurately capture the rates of cross-cell contamination. We further designed the experiment to assess the levels of crosstalk at both points of possible introduction: at the tagmentation stage and PCR stage, by mixing nuclei from the two samples before tagmentation as well as after. In addition, we produced pure species libraries by leveraging the inherent sample multiplexing capabilities of single-cell combinatorial indexing workflows. In total, we generated 1,366 human and 1054 mouse single-cell ATAC-seq profiles with a median of 30,886 and 26,530 unique, high mapping quality reads aligned to chromosomes 1-22, 23 (human), X and Y (hereafter referred to as "passing reads") per cell for human and mouse respectively. Notably, the libraries are highly complex, with a median of 69.05% of reads assigned to cells as unique, indicating that additional sequencing depth would greatly increase the coverage obtained beyond that of the depth currently sequenced. Using our established method for projecting out unique reads per cell, for which projected estimates fall within 2% of empirical data upon further sequencing[9], we found that our libraries reach a median of 128,144 and 174,858 passing reads per cell at 95% library saturation for the human cortical and mouse whole brain samples respectively. We next compared our current depth as well as projections for our mouse brain samples to publicly available datasets on comparable tissue as well as on the projections of those libraries when available. We found that our libraries exceed an order of magnitude improvement over any other library or self-reported library projection FIG. 16.

Figure 17:
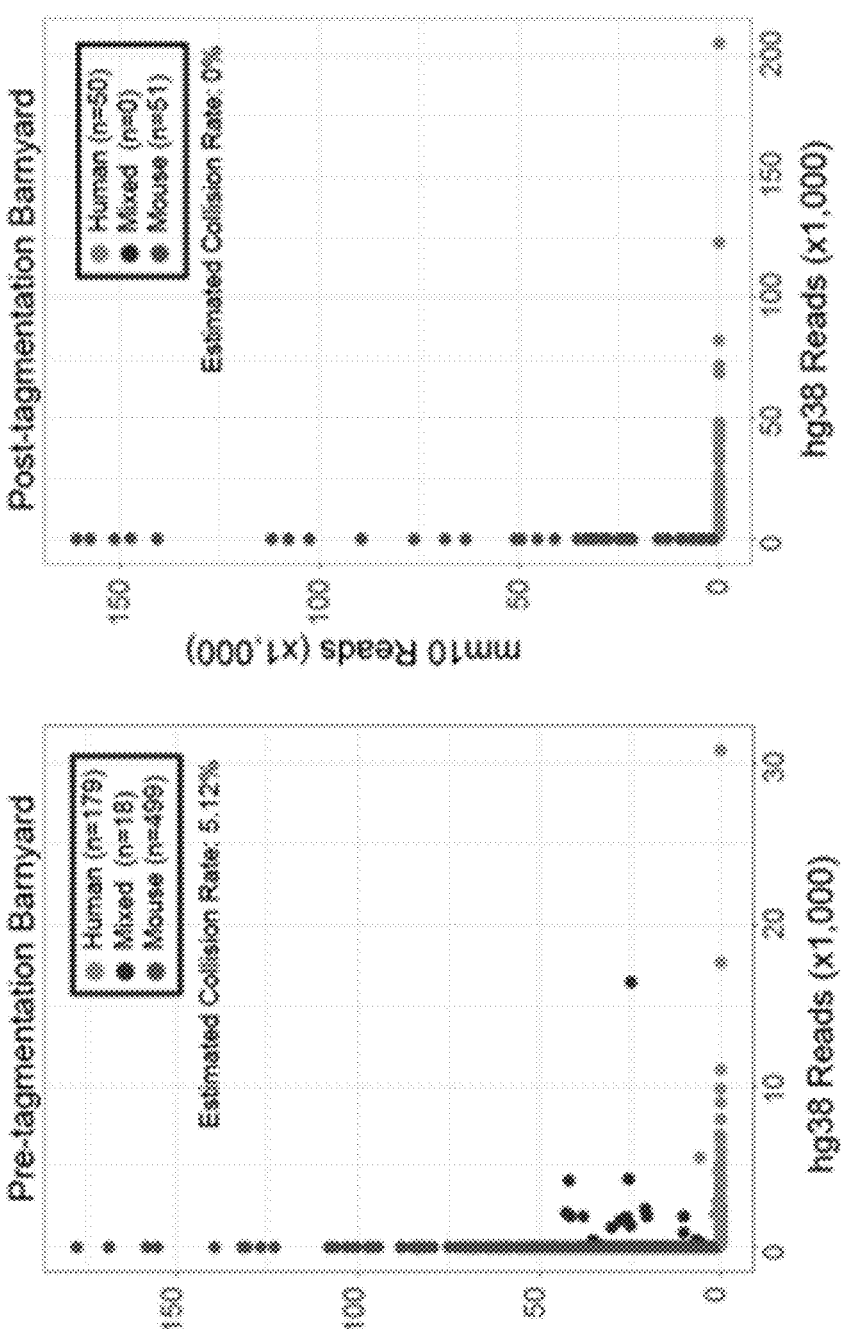
FIG. 17 shows comparison of human and mouse reads per cell on "true barnyard" (left; mixed species tagmentation wells) and PCR barnyard (right; species mixed at PCR stage) display little to no intercellular exchange of library molecules. Index collision rate of 5.12% in the true barnyard suggests an optimal 15 nuclei per well for acceptable collision rate.
Figure 18:
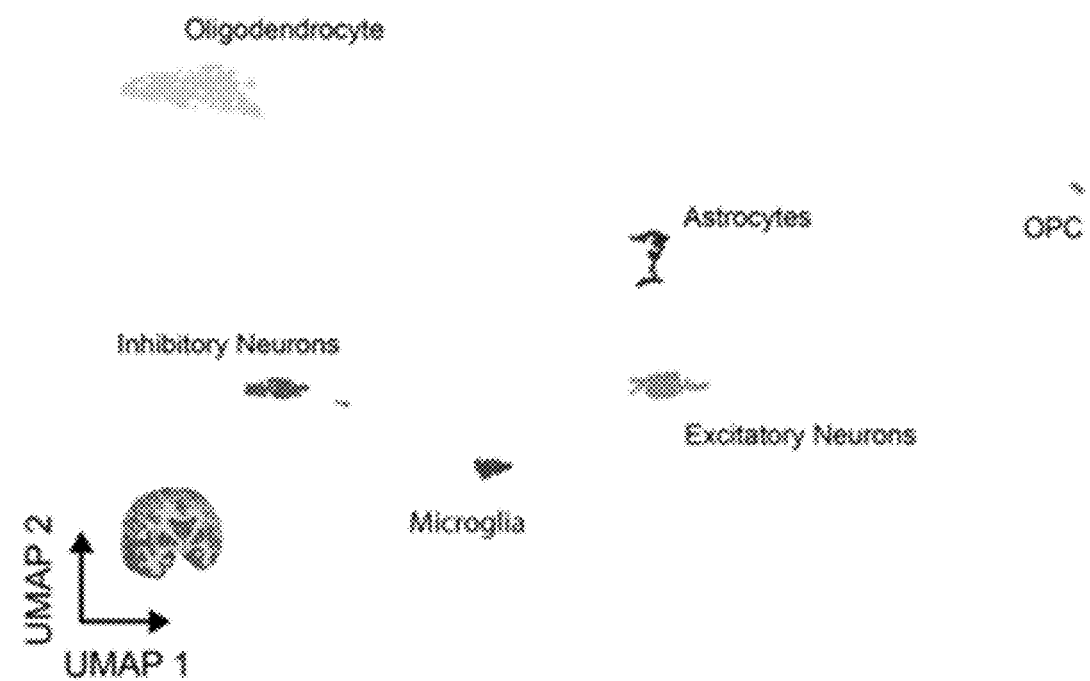
FIG. 18 shows UMAP projection of human nuclei.
Figure 19:
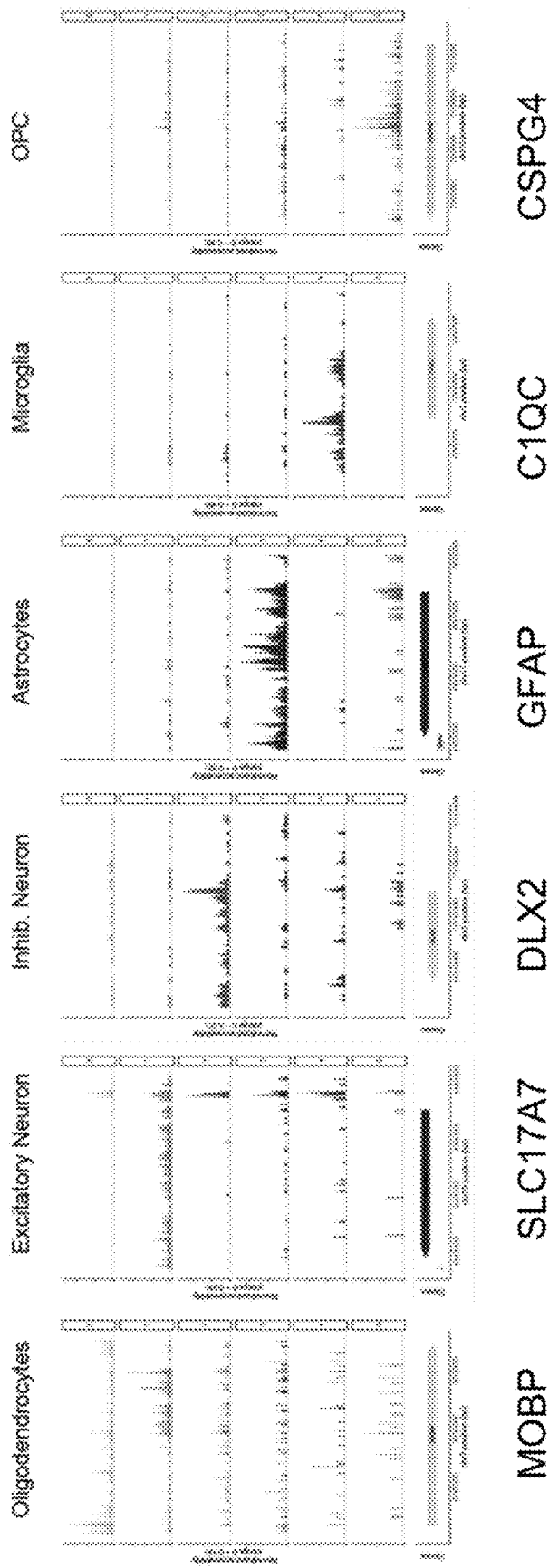
FIG. 19 shows canonical markers for gross cell types within the cortex reveal distinct cell populations.
Figure 20:
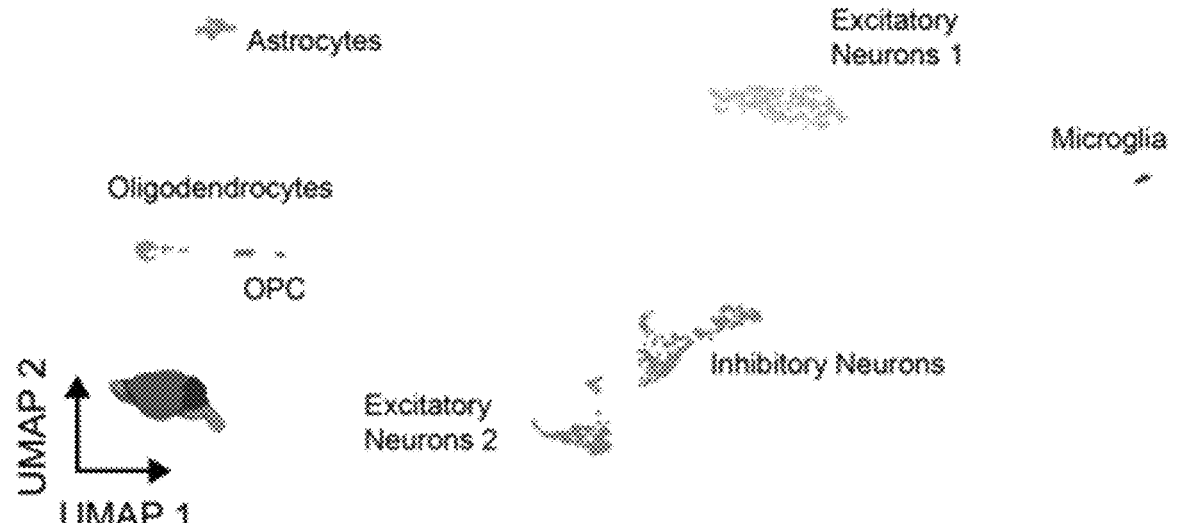
FIG. 20 shows a UMAP projection of mouse nuclei.
Figure 21:
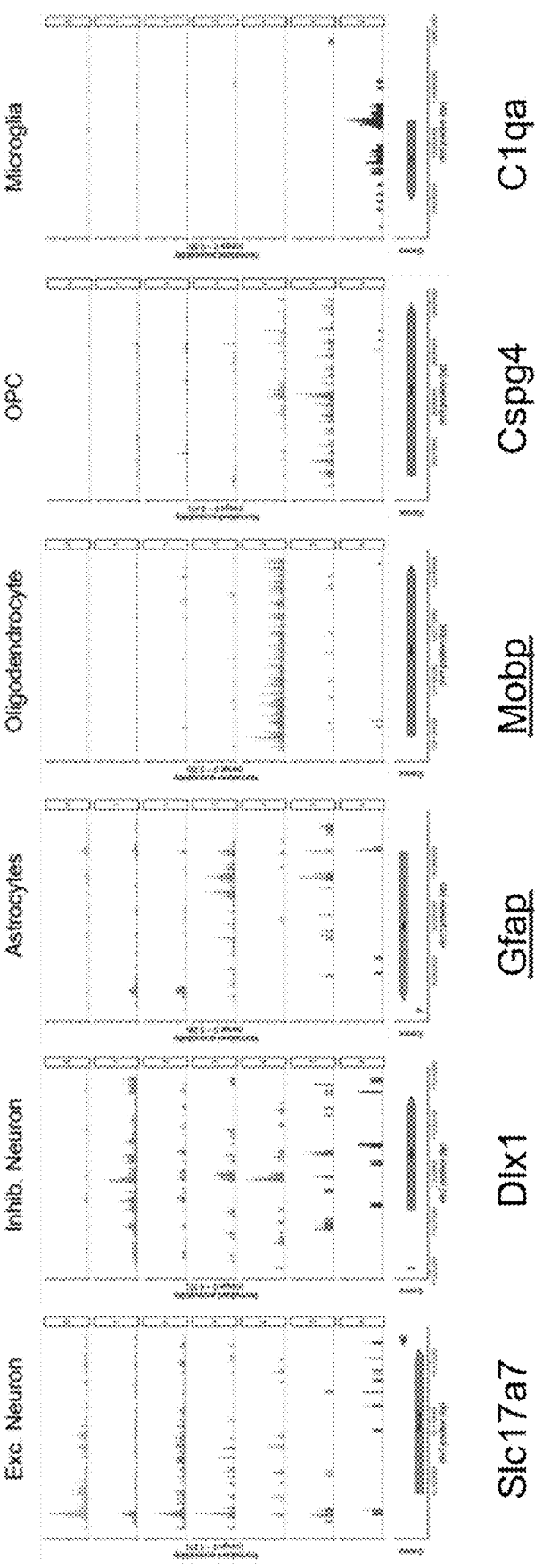
FIG. 21 shows canonical markers for gross cell types within the mouse brain reveal distinct cell populations.

To ensure our improvements are not due to index duplicates or genomic cross-talk, we demonstrated the purity of our samples by assessing unique read counts aligning to a human-mouse combined reference genome. In the experimental condition where nuclei were mixed prior to any processing, i.e., pre-tagmentation, we observed a collision rate of 5.12% (FIG. 17; 2×2.56% detected human-mouse collisions), well within acceptable levels. We observed zero collisions in the post-tagmentation experimental conditions, as to be expected, suggesting the collisions observed in the pre-tagmentation experiment are due to sampling doublets as opposed to crosstalk or ambient chromatin. We also ensured that the increased reads are indeed capturing biological signal and not due to an excess of background by assessing the transcription start site (TSS) enrichment, at a median of 2.77 and 3.93, and the fraction of reads in called peaks (FRIP), at 14.60% and 19.40% for human and mouse samples respectively, with both metrics comparable to other platforms for matched tissue types. With ample signal, we next sought to discern cell types present within the samples. For each species, we used peaks called on aggregate data to construct a counts matrix followed by dimensionality reduction using the topic-modeling tool cisTopic[13] which we then visualized using UMAP[14], and finally performed graph-based clustering at the topic level. We found clear separation of cell types in both the visualization space as well as in the identified clusters, with clear signal at cell type specific genes within each cluster for both human cortex and mouse whole brain samples (FIG. 18-21).

We next reasoned that the improvements in data quality produced by s3-ATAC should be translatable to other single-cell combinatorial indexing workflows, including our previously reported sci-DNA-seg method for high throughput low-pass single-cell genome sequencing[9]. In addition to using the s3 workflow (FIG. 7), we also explored other improvements to the nucleosome depletion component of the technique, which is used obtain even coverage. We first deployed s3-WGS (FIG. 6) on a control lymphoblastoid cell line (GM12878), which revealed that an optimized version of detergent-based nucleosome depletion (xSDS) provided the best uniformity and read counts, with the 92 cells in that condition projecting out to a median of 6,584,602 passing reads per cell which translates to a median genomic capture rate of 37.12%. We also confirmed that the coverage was uniform by assessing the median absolute deviation (MAD), which fell within 0.1-0.3 (median 0.18), comparable to other single-cell genome sequencing techniques. Using this optimized protocol, we next deployed s3-WGS to sequence two cell lines derived from primary pancreatic ductal adenocarcinoma (PDAC) tumors after minimal passage counts.

Figure 22:
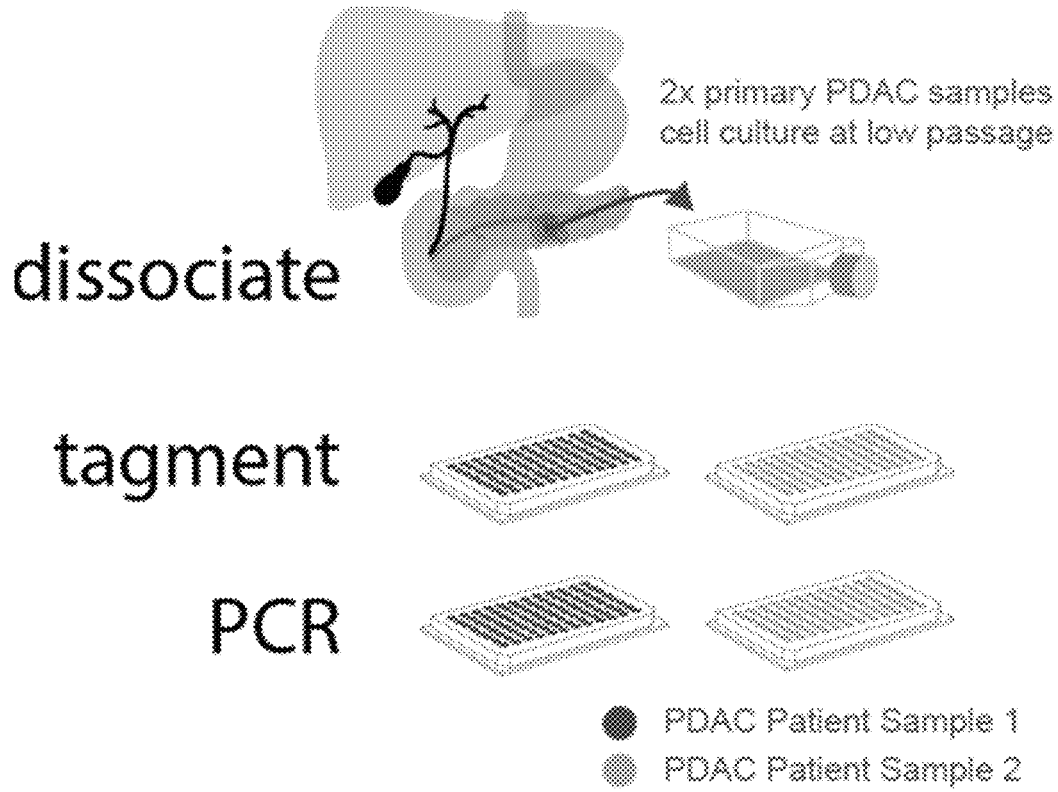
FIG. 22 shows experimental layout of PDAC low-passage patient derived lines for generation of s3-WGS libraries showing indexing at both tagmentation and PCR stages for multiple 96-well plates.
Figure 23:
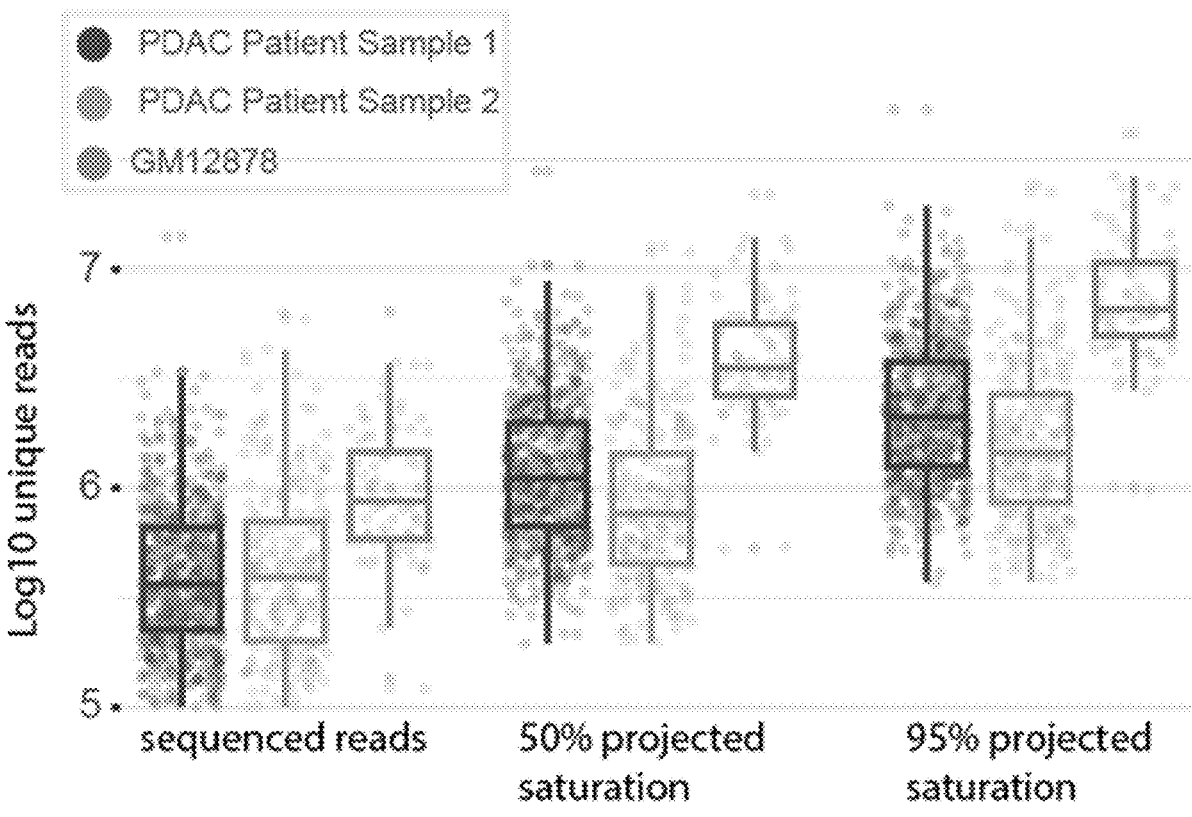
FIG. 23 shows boxplots of library complexity as measured by unique reads per cell, as well as projections to library saturation.
Figure 24:
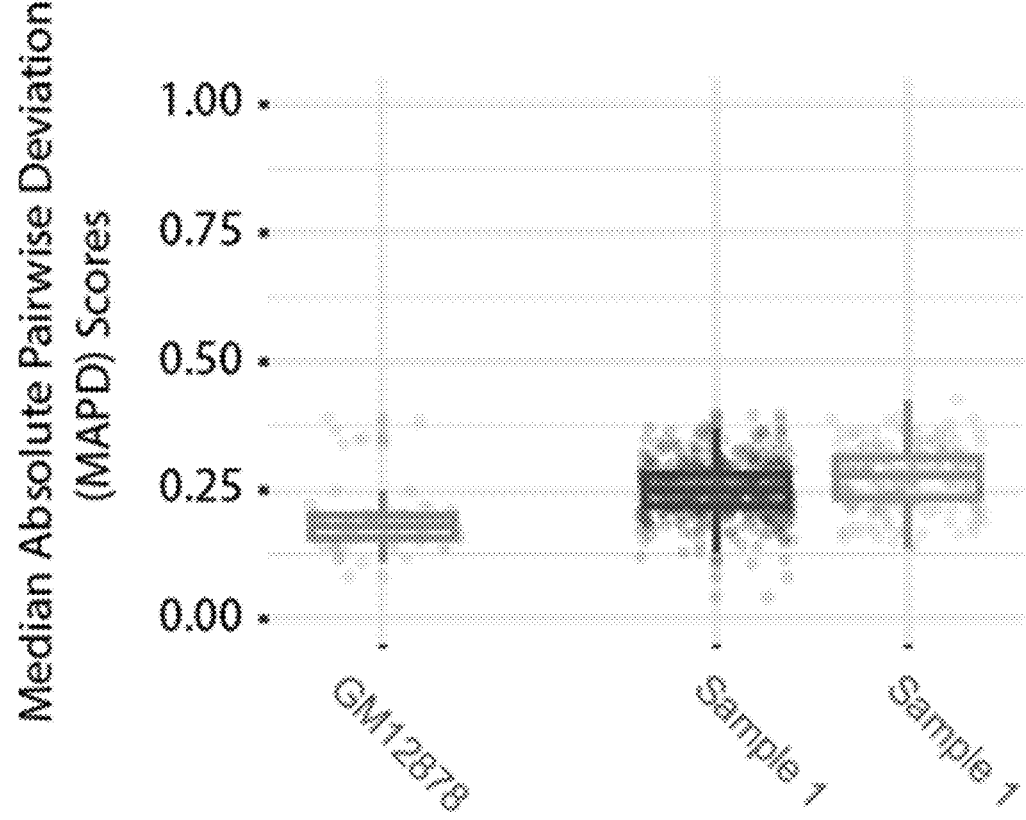
FIG. 24 shows boxplots of mean absolute deviation (MAD) scores for unbiased genomic coverage across bins. Key continued from FIG. 23.
Figure 25:
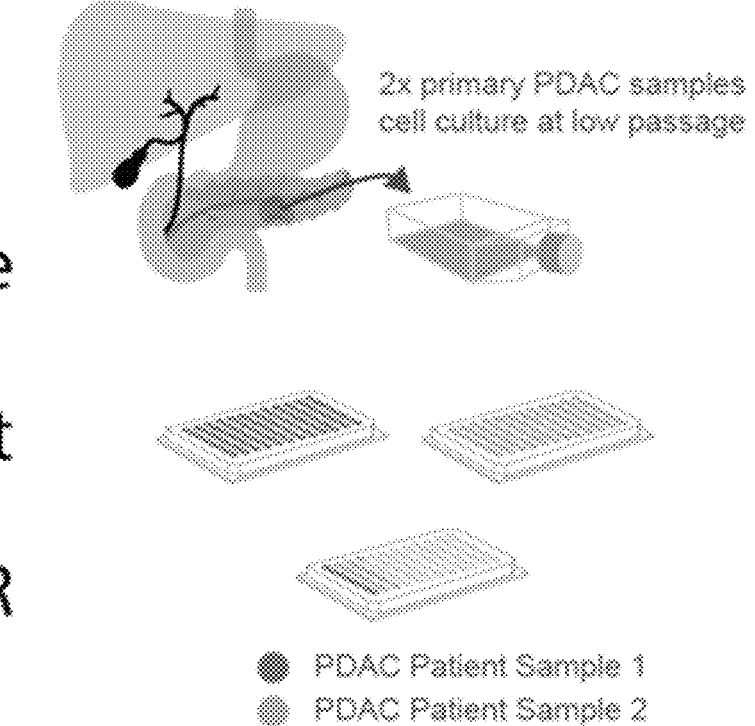
FIG. 25 shows experimental layout of PDAC low-passage patient derived lines for generation of s3-GCC libraries. showing indexing at both tagmentation and PCR stages for multiple 96-well plates.
Figure 26:
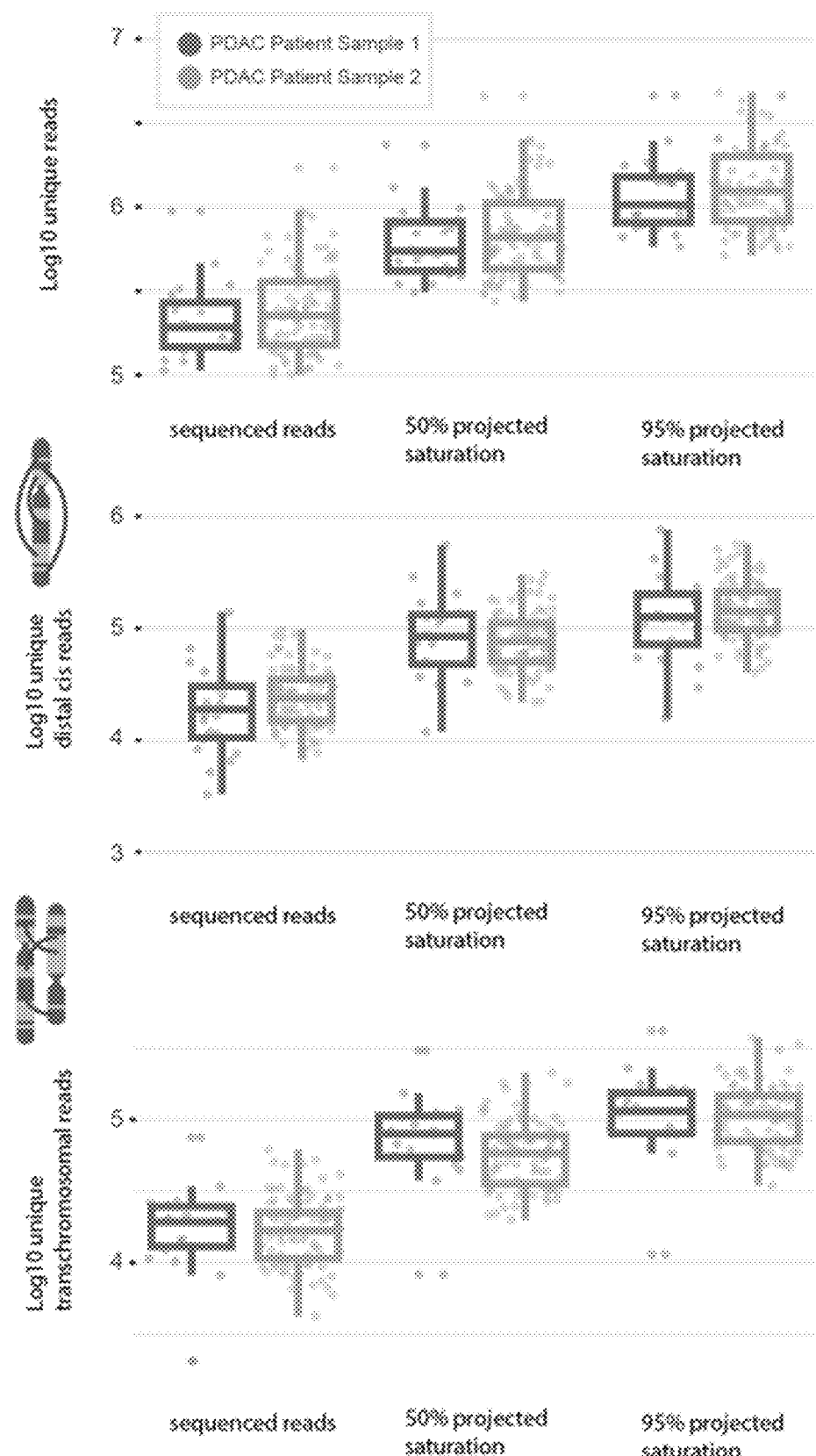
FIG. 26 shows boxplots of library complexity as measured by unique reads per cell, as well as projections to 50% and 95% library saturation. Top: total reads; middle: distal (>1 kbp mapped) intrachromosomal reads; bottom: transchromosomally mapped reads.
Figure 27:
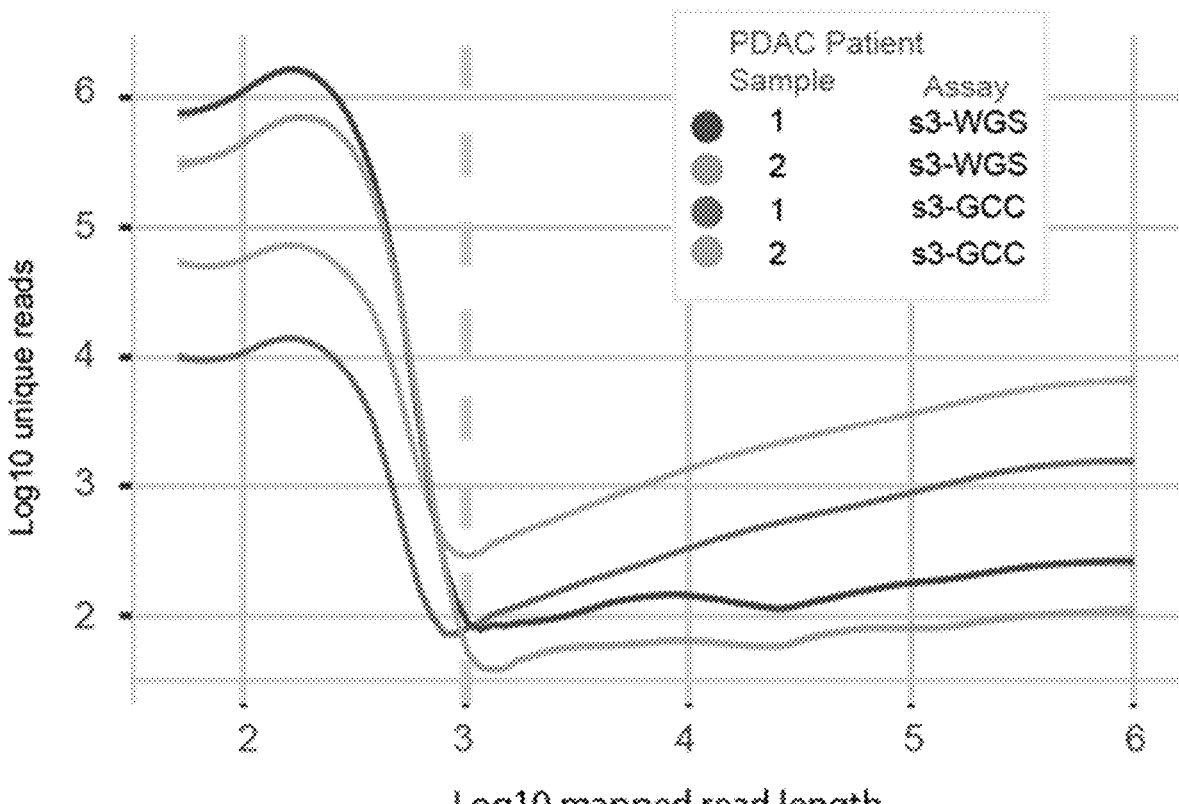
FIG. 27 shows density plot of mapped read length distribution showing distal region capture.

PDAC is a devastating form of cancer, that typically presents at an advanced stage, making early detection and study of tumor progression key. PDAC studies suffer from a low cancer cell fraction in biopsied samples, thus we used continuously-regenerating cell lines (CRCs) derived at low passage from purified tumors. This method allows for multiple modalities of characterization and perturbation, while maintaining a large portion of the heterogeneity present in the tumor sample, as evidenced by karyotyping[15]. We targeted two lines (referred to as PDAC-1 and PDAC-2) which had two distinct subclonal missense mutations of the oncogene KRAS (p.G12D and p.G12C) and profound genomic instability as measured through G-banding based and spectral karyotyping. For the lines we obtained 709 and 267 single cell libraries with median projected passing read counts of U.S. Pat. Nos. 2,096,207 and 1,445,381 for PDAC-1 and PDAC-2, respectively (FIGS. 22-24). While lower than the initial GM12878 control sample, it greatly exceeds the coverage obtained by predecessor methods. The MAD scores for the two lines (FIG. 24) were greater than that of the relatively normal karyotype of GM12878, with a median of 0.28 and 0.32; however, this is to be expected given the widespread copy number alterations present in the samples. We validated this expectation with paired whole exome sequencing and copy number calling from PDAC-1 primary tumor, normal blood and CRC line, uncovering strong evidence of the hallmark genomic instability. We next performed single-cell copy number profiling and identified a highly altered genomic landscape within each of the two lines. In line with the limited karyotyping data and whole exome data, we see a similar pattern per cell of multi-megabase sized copy number aberrations. Using the inferred copy number profile within genomic windows for the three samples, GM12878 and two PDAC lines, we performed hierarchical and K-means clustering, revealing multiple clonal genomic arrangements.

Given our single-cell resolution, we were able to assess the occurrence of known PDAC-associated oncogene and tumor suppressor copy number aberrations. As an instance of cross-patient differences, cluster 7, occupied solely by PDAC-2 samples, shows a unique amplification of a genomic region containing TGFβR2 and PBRM1, a region associated with cell proliferation and previously associated with higher cancer cell tumor fractions in PDAC patients. PDAC-1 samples reveal a heterogenous amplification of the genomic region containing the oncogene MYC (absolute copy number 2.26±2.36). Additionally, we uncovered a focal amplification of the genomic range overlapping the onco-gene KRAS, known to occur in over 90% of PDAC cases. We found that cluster 1 had the lowest number of cells with a KRAS amplification (23.3%, 40/172 cells), whereas clus-ter 5 had the greatest frequency of KRAS copy number gain (82.6%, 138/167 cells). We validated this heterogenous copy number aberration by leveraging our whole exome data for genotyping and digital droplet PCR, finding that 53% of KRAS alleles sampled from PDAC-1 CRC lines presented with a mutated KRAS allele linked to overexpression.

Duplications and deletions are not the sole form of genomic rearrangement that may induce a competitive advantage in cancer cell growth. Genomic inversions are difficult to assess through standard karyotyping and chro-mosome painting methods, whereas chromosomal translo-cations are difficult to uncover in whole-genome amplifica-tion methods, since only reads capturing the breakpoint would provide supportive evidence. To address both of these limitations, we utilized the s3-WGS technique with an additional pre-processing workflow to restriction digest after fixation and nucleosome depletion and then re-ligate (as in HiC methods but without the incorporation of biotinylated bases) followed by the s3 library preparation. We reasoned that this additional processing would result in a portion of reads to span chimeric ligation junctions indicative of distal chromatin contact points, with the remaining reads serving as whole genome sequencing data, enabling both genome and chromatin conformation (s3-GCC) (FIG. 9). We per-formed s3-GCC on the same two PDAC cell lines (FIG. 25-28) as in the s3-WGS experiments to produced 22 and 93 cell profiles with comparable projected median passing reads per cell at 1,034,014 and 1,245,266 for PDAC-1 and PDAC-2, respectively. We then performed copy number calling and compared the results with the s3-WGS libraries, revealing similar patterns with each method's profiles inter-spersed within the other within cell line groups. To obtain an initial measurement of chromatin conformation signal, we assessed the proportion of interchromosomal read pairs for which both s3-GCC preparations contained an excess at a 68.91 and 58.91 fold increase over their s3-WGS counter-parts. We then measured the proportion of reads with an insert size greater than 1 kbp, which averaged 16%, with a median of 15.6% and 17.0% for each line respectively, again with comparable median fold enrichment over s3-WGS at 361 and 402 fold. To assess the total expected unique chromosome contact points per cell we first assumed that the read count projections for chromatin contacts performed the same as for the bulk of the data which represent standard genome sequencing reads, allowing us to take the percent-age of the total passing read counts. This produced projected median contact points per cell of 20,451 for PDAC-1 and 20,611 for PDAC-2. Additionally, we performed read count projections specifically on the portion of reads that represent chromatin contacts and obtained similar values at 244,728 and 245,560. We then used the contact points obtained from our relatively shallow sequencing depth and demonstrated the ability to produce chromatin contact maps, with aggre-gate profiles showing distinct topological patterns. We sepa-rated single-cells by their distal contact information via scHiCluster and observed three distinct clusters. Notably, even at this low sequencing depth, we are able to reliably tell cell line sparse contact profiles apart. We looked at differ-ences between the aggregated contact maps of clusters 0 (occupied exclusively PDAC-1) and 1 to assess unique translocation and inversion events across the sampled cells. We found that our single-cell contact data replicates the reported chromosome arm scale translocations from spectral karyotyping (SKY) data, particularly in the example of an uncovered t(3; 14)(q24-26; q21-24) translocation for PDAC-1 samples. We also find enriched inter-chromosomal contact frequencies between the TGFβR2 and PBRM1 region of chromosome 3 seen in our s3-WGS data, towards chromosomes 2 and 4 suggesting aberrant genomic com-partmentalization of the copy number gains.

Taken together, our s3 workflow represents marked improvements over the predecessor sci platform with respect to passing reads obtained per cell without sacrificing signal enrichment in the case of s3-ATAC, or coverage uniformity for s3-WGS. We also introduce another variant of combi-natorial indexing workflows, s3-GCC to obtain both genome sequencing and chromatin conformation, with improved chromatin contacts obtained per cell when compared to sci-HiC. We demonstrate the utility of these approaches by assessing two patient-derived tumor cell lines with dramatic chromatin instability. We reveal patterns of focal amplifica-tion of disease relevant genes, and uncover wide-scale heterogeneity at a throughput not attainable with standard karyotyping. Additionally, we highlight the joint analysis of our protocols for uncovering the chromatin compartment disrupting effect of copy number aberrations. Furthermore, the s3 workflow has the same inherent throughput potential of standard single-cell combinatorial indexing. We also expect that this platform will be compatible with other transposase-based techniques, including sci-MET[10]. One possible drawback of the s3 platform is that a full set of unique transposome complexes must be used as opposed to using a set of 8 forward and 12 reverse complexes (corre-sponding to rows and columns of a 96-well plate), making the number of oligos required for the workflow greater. However, these costs ultimately balance out, as proportion-ately less oligo is required per experiment. Lastly, unlike sci workflows, the s3 platform does not require custom sequencing primers or custom sequencing recipes, removing one of the major hurdles labs may face while implementing these technologies.

CITATIONS FOR EXAMPLE 2

1. Cusanovich, D. A. et al. Multiplex single-cell profiling of chromatin accessibility by combinatorial cellular index-ing. *Science* (80-.). 348, 910-914 (2015).
2. Adey, A. et al. Rapid, low-input, low-bias construction of shotgun fragment libraries by high-density in vitro trans-position. *Genome Biol.* 11, R119 (2010).
3. Tan, L., Xing, D., Chang, C. H., Li, H. & Xie, X. S. Three-dimensional genome structures of single diploid human cells. Science (80-.). 361, 924-928 (2018).
4. Sos, B. C. et al. Characterization of chromatin accessi-bility with a transposome hypersensitive sites sequencing (THS-seq) assay. *Genome Biol.* 17, 20 (2016).
5. Yin, Y. et al. High-Throughput Single-Cell Sequencing with Linear Amplification. *Mol. Cell* 76, 676-690.e10 (2019).

6. Chen, C. et al. Single-cell whole-genome analyses by Linear Amplification via Transposon Insertion (LIANTI). *Science* (80-.). 356, 189-194 (2017).

7. Adey, A. & Shendure, J. Ultra-low-input, tagmentation-based whole-genome bisulfite sequencing. *Genome Res.* 22, 1139-1143 (2012).

8. Mulqueen, R. M. et al. Highly scalable generation of DNA methylation profiles in single cells. *Nat. Biotechnol.* 36, 428-431 (2018).

9. Vitak, S. A. et al. Sequencing thousands of single-cell genomes with combinatorial indexing. *Nat. Methods* 14, 302-308 (2017).

10. Mulqueen, R. M. et al. Highly scalable generation of DNA methylation profiles in single cells. *Nat. Biotechnol.* 36, 428-431 (2018).

11. Vitak, S. A. et al. Sequencing thousands of single-cell genomes with combinatorial indexing. *Nat. Methods* 14, (2017).

12. Ramani, V. et al. Massively multiplex single-cell Hi-C. *Nat. Methods* 14, 263-266 (2017).

13. Bravo Gonzilez-Blas, C. et al. cisTopic: cis-regulatory topic modeling on single-cell ATAC-seq data. *Nat. Methods* 16, 397-400 (2019).

14. Becht, E. et al. Dimensionality reduction for visualizing single-cell data using UMAP. *Nat. Biotechnol.* 37, 38-44 (2018).

15. Lindenburger, K. et al. AB024. S024. Drug responses of patient-derived cell lines in vitro that match drug responses of patient PDAc tumors in situ. *Ann. Pancreat. Cancer* 1, AB024-AB024 (2018).

Methods s3-ATAC Library Generation

Prior to sample handling, complexed transposases were obtained from ILLUMINA® Inc. 96 uniquely indexed transposases were loaded with one of the respective adapters and diluted to 2.5 uM and stored at −20° C. 50 mL of nuclei isolation buffer (NIB-HEPES) was freshly prepared with final concentrations of 10 mM HEPES-KOH (FISHER SCIENTIFIC®, BP310-500 and SIGMA ALDRICH® 1050121000, respectively), pH 7.2, 10 mM NaCl (FISHER SCIENTIFIC® 5271-3), 3 mM MgCl2 (FISHER SCIENTIFIC® AC223210010), 0.1% (v/v) IGEPAL CA-630 (SIGMA ALDRICH® I3021), 0.1% (v/v) Tween (SIGMA-ALDRICH® P-7949) and diluted in PCR-grade Ultrapure distilled water (THERMO FISHER SCIENTIFIC® 10977015). After dilution, two tablets of Pierce™ Protease Inhibitor Mini Tablets, EDTA-free (FISHER SCIENTIFIC® A32955) were dissolved and suspended to prevent protease degradation during nuclei isolation.

For s3-ATAC tissue handling, primary samples of C57/B6 mice whole brain and human cortex were extracted and flash frozen in a liquid nitrogen bath, before being stored at −80° C. An at-bench dissection stage was set up prior to nuclei extraction. A petri dish was placed over dry ice, with fresh sterile razors pre-chilled by dry-ice embedding. 7 mL capacity dounce homogenizers were filled with 2 mL of NIB-HEPES buffer and held on wet ice. Chill dounce homogenizer pestles by holding in ice cold 70% (v/v) ethanol (Decon Laboratories Inc 2701) in 15 mL tubes on ice. Immediately prior to use, pestles were rinsed with chilled distilled water. For tissue dissociation, mouse and human brain samples were treated similarly. The still frozen block of tissue was placed on the clean pre-chilled petri dish and roughly minced with the razors. Razors were then used to transport roughly 1 mg the minced tissue into the chilled NIB-HEPES buffer within a dounce homogenizer. Suspended samples were given 5 minutes to equilibrate to the change in salt concentration prior to douncing. Tissues were then homogenized with 5 strokes of a loose (A) pestle, another 5 minute incubation, and 5-10 strokes of a tight (B) pestle. Samples were then filtered through a 35 μm cell strainer (Corning 352235) during transfer to a 15 mL conical tube, and nuclei were held on ice until ready to proceed. Nuclei were pelleted with a 400 rcf centrifugation on a 4° C. centrifuge for 10 minutes. Supernatant was removed and pellets were resuspended in 1 mL of NIB-HEPES buffer. This step was repeated for a second wash, and nuclei were once again held on ice until ready to proceed. A 10 uL aliquot of suspended nuclei was diluted in 90 uL NIB-HEPES (1:10 dilution) and quantified on either a Hemocytometer or with a BIORAD® TC-20 Automated cell counter following manufacturer's recommended protocols. The stock nuclei suspension was then diluted to a concentration of 1400 nuclei/uL.

Tagmentation plates were prepared by the combination of 420 μL of 1400 nuclei/uL solution with 540 uL 2×TD Buffer (NEXTERA® XT Kit, ILLUMINA® Inc.) From this mixture, 8 uL (~5000 nuclei total) was pipetted into each well of a 96 well plate dependent on well schema. 1 uL of 2.5 uM uniquely indexed transposase was then pipetted into each well. Tagmentation was performed at 55° C. for 10 minutes on a 300 rcf EPPENDORF® THERMOMIXER®. Following this incubation, plate temperature was brought down with a brief incubation on ice to stop the reaction. Dependent on experimental schema pools of tagmented nuclei were combined and 2 uL 5 mg/mL DAPI (THERMO FISHER SCIENTIFIC® D1306) was added.

Nuclei were then flow sorted via a Sony® SH800 to remove debris and attain an accurate count per well prior to PCR. A receptacle 96 well plate was prepared with 9 uL 1×TD buffer (diluted with ultrapure water). And held in a sample chamber kept at 4° C. Fluorescent nuclei were then flow sorted gating by size, internal complexity and DAPI fluorescence for single nuclei. Immediately following sorting completion, the plate was sealed and spun down for 5 minutes at 500 rcf and 4° C. to ensure nuclei were within the buffer.

Nucleosomes and remaining transposase were then denatured with the addition 1 uL of 0.1% SDS (~0.01% f.c.) per well. 4 μL of NPM (NEXTERA® XT Kit, ILLUMINA® Inc) per well was subsequently added to perform gap-fill on tagmented genomic DNA, with an incubation at 72° C. for 10 minutes. 1.5 uL of 1 uM A14-LNA-ME oligo was then added to supply the template for adapter switching. The polymerase based adapter switching was then performed with the following conditions: initial denaturation at 98° C. for 30 seconds, 10 cycles of 98° C. for 10 seconds, 59° C. for 20 seconds and 72° C. for 10 seconds. The plate was then held at 10° C. After adapter switching 1% (v/v) Triton-X 100 in ultrapure H2O (Sigma 93426) was added to quench persisting SDS. At this point, some plates were stored at −20° C. for several weeks while others were immediately processed.

The following was then combined per well for PCR: 16.5 ul sample, 2.5 uL indexed i7 primer at 10 uM, 2.5 uL indexed i5 primer at 10 uM, 3 μL of ultrapure H2O, and 25 μL of NEBNEXT® Q5U 2× Master mix (NEW ENGLAND BIOLABS® M0597S), and 0.5 uL 100×SYBR® Green I (THERMO SCIENTIFIC® S7563) for a 50 uL reaction per well. A real time PCR was performed on a BIORAD® CFX with the following conditions, measuring SYBR fluorescence every cycle: 98° C. for 30 seconds; 16-18 cycles of 98° C. for 10 seconds, 55° C. for 20 seconds, 72° C. for 30 seconds, fluorescent reading, 72° C. for 10 seconds. After fluorescence passes an exponential growth and begins to inflect, the samples were held at 72° C. for another 30 seconds then stored at 4° C.

Amplified libraries were then cleaned by pooling 25 uL per well into a 15 mL conical tube and cleaned via a Qiaquick PCR purification column following manufacturer's protocol (QIAGEN® 28106). The pooled sample was eluted in 50 uL 10 mM Tris-HCl, pH 8.0 (Life technologies AM9855). Library molecules then went through a size selection via SPRI selection beads (Mag-Bind® TotalPure NGS Omega Biotek M1378-01). 50 μL of vortexed and fully suspended room temperature SPRI beads was combined with the 50 uL library (1× clean up) and incubated at room temperature for 5 minutes. The reaction was then placed on a magnetic rack and once cleared, supernatant was removed. The remaining pellet was rinsed twice with 100 uL fresh 80% ethanol. After ethanol was pipetted out, the tube was spun down and placed back on the magnetic rack to remove any lingering ethanol. 31 μL of 10 mM Tris-HCl, pH 8.0 was then used to resuspend the beads off the magnetic rack and allowed to incubate for 5 minutes at room temperature. The tube was again placed on the magnetic rack and once cleared, the full volume of supernatant was moved to a clean tube. DNA was then quantified by Qubit dsDNA High-sensitivity assay following manufacturer's instructions (FISHER SCIENTIFIC® Q32851). Libraries were then diluted to 2 ng/uL and run on an Agilent AGILENT® TAPESTATION® 4150 D5000 tape (AGILENT®5067-5592). Library molecule concentration within the range of 100-1000 bp was then used for final dilution of the library to 1 nM. Diluted libraries were then sequenced on High or Mid capacity 150 bp sequencing kits on the NEXTSEQ® 500 system following manufacturer's recommendations (ILLUMINA® Inc.).

s3-WGS Library Generation

Prior to processing the following buffers were prepared: 50 mL of NIB HEPES buffer as described above, as well as 50 mL of a Tris-based NIB (NIB Tris) variant containing with final concentrations of 10 mM Tris HCl pH 7.4 (LIFE TECHNOLOGIES® AM9855), 10 mM NaCl, 3 mM MgCl2, 0.1% (v/v) IGEPAL CA-630, 0.1% (v/v) Tween and diluted in PCR-grade Ultrapure distilled water. After dilution, two tablets of Pierce™ Protease Inhibitor Mini Tablets, EDTA-free were dissolved and suspended to prevent protease degradation during nuclei isolation.

s3-WGS library preparation was performed on cell lines as follows. For patient derived CRC cell lines, cells were plated at a density of 1×106 on a T25 flask the day prior to processing. Cells were washed twice with ice cold 1×PBS (VWR 75800-986) and then trypsinized with 5 mL 1× TrypLE (Thermo Fisher 12604039) for 15 minutes at 37° C. Suspended cells were then collected and pelleted at 300 rcf at 4° C. for 5 minutes. For suspension-growth cell lines (GM12878), cells were pipetted from growth media and pelleted at 300 rcf at 4° C. for 5 minutes.

Following the initial pellet, cells were washed with ice cold 1 mL NIB HEPES twice. After the second wash, pellets were then resuspended in 300 uL NIB HEPES. Nuclei were aliquoted and quantified as described above, then 1 million nuclei aliquots were generated based on the quantification. The aliquots were pelleted by a 300 rcf centrifugation at 4° C. for 5 minutes and resuspended in 5 mL NIB HEPES. 246 uL 16% (w/v) formaldehyde (Thermo Fisher® 28906) was then added to nuclear suspensions (f.c. 0.75% formaldehyde) to lightly fix nuclei. Nuclei were fixed via incubation in formaldehyde solution for 10 minutes on an orbital shaker set to 50 rpm. Suspensions were then pelleted at 500 rcf for 4 minutes at 4° C. and supernatant was aspirated. Pellet was then resuspended in 1 mL of NIB Tris Buffer to quench remaining formaldehyde. Nuclei were again pelleted at 500 rcf for 4 minutes at 4° C. and supernatant was aspirated. The pellet was washed once with 500 uL 1× NEBuffer 2.1 (NEB® B7202S) and then resuspended with 760 uL 1×NEBuffer 2.1. 40 uL 1% SDS (v/v) was added and sample was incubated on a THERMOMIXER® at 300 rcf set to 37° C. for 20 minutes. Nucleosome depleted nuclei were then pelleted at 500 rcf at 4° C. for 5 minutes and then resuspended in 50 uL NIB Tris. A 5 μL aliquot of nuclei was taken and diluted 1:10 in NIB Tris then quantified as described above. Nuclei were diluted to 500 nuclei/uL with addition of NIB Tris, based on the quantification. Dependent on experimental setup, the 420 μL of nuclei at 500 nuclei/uL were then combined with 540 uL 2×TD buffer. Following this, nuclei were tagmented, stained and flow sorted, genomic DNA was gap-filled and adapter switching was performed as described for the s3-ATAC protocol. Library amplification was performed by PCR as described above with fewer total cycles (13-15) likely due to more initial capture events per library. Libraries were then cleaned, size selected and sequenced as described previously.

s3-GCC Library Generation

The same cultured cell line samples were sampled as described for s3-WGS library generation, and processed from the same pool of fixed, nucleosome depleted nuclei. Following quantification of nuclei, the full remaining nuclear suspensions (~2-3 million nuclei per sample) were pooled respective of sample. Nuclei were pelleted at 500 rcf at 4° C. for 5 minutes and resuspended in 90 uL 1× Cutsmart Buffer (NEB B7204S). 10 μL of 10U/uL AluI restriction enzyme (NEB R0137S) was added to each sample. Samples were then digested for 2 hours at 37° C. at 300 rpm on a ThermoMixer. Following digestion, nuclear fragments then underwent proximity ligation. Nuclei were pelleted at 500 rcf at 4° C. for 5 minutes and resuspended in 100 uL ligation reaction buffer. Ligation buffer is a mixture with final concentrations of 1×T4 DNA Ligase Buffer+ATP (NEB M0202S), 0.01% TritonX-100, 0.5 mM DTT (Sigma D0632), 200 U of T4 DNA Ligase, diluted in ultrapure H2O. Ligation took place at 16° C. for 14 hours (overnight). Following this incubation, nuclei were pelleted at 500 rcf at 4° C. for 5 minutes and resuspended in 100 uL NIB HEPES buffer. An aliquot of nuclei were quantified as described previously, and were then diluted, aliquoted, tagmented, pooled, DAPI stained, flow sorted, genomic DNA was gap-filled and adapter switching was performed as described for the s3-ATAC protocol. Library amplification occurred at the same rate as the s3-WGS libraries (13-15 cycles) and libraries were subsequently pooled, cleaned and sequenced as described above.

Example 3

Preparation of Libraries Via Combined Tagmentation and Indexing

The following example demonstrates a method and system for preparing dual-indexed paired-end libraries from a nucleic sample using a combined tagmentation and indexing step. The first index sequence is added via tagmentation and the second index sequence is added via hybridization and extension.

This example uses an immobilized transposome complex having a transposon with a first strand of 5'-primer-index-adaptor-Uracil-transposase recognition domain, e.g., 5'-P5-i5-A14-U-ME-3', and a second strand that is the complement of the transposase recognition sequence, e.g., 5'-ME'-3'. An exemplary first strand of a transposon is SEQ ID NO:1 and an exemplary second strand of the transposon is the complement of nucleotides 53-71 of SEQ ID NO:1. The transposome complex is immobilized on a bead through a biotin attached via cleavable linker to the 5' end of the first strand. The oligonucleotide containing the second index sequence has a sequence of 5'-primer-index-adaptor-transposase recognition sequence, e.g., 5'-P7-i7-B15-ME-3'. An exemplary oligonucleotide containing the second index sequence is SEQ ID NO:2. The second index sequence is optionally blocked at the 3' end, e.g., using a dideoxy or locked nucleic acid. Exemplary sequences for P5, i5, P7, i7, ME, A14, and B15 are SEQ ID NOs:3-9, respectively.

Nucleic acid in solution is added to each well of a 96-well plate in a desired range. A suspension of bead-linked transposomes having the transposon sequences described above is added to each well and the plate is incubated under conditions suitable to allow the transposases to fragment and insert the transposon sequences. The transposase enzyme is removed, e.g., by adding SDS or heating. A uracil-intolerant polymerase (e.g., proof-reading polymerase or PHUSION®) is added to fill in the gap between the nucleic acid fragment end and the second transposon sequence. The uracil-intolerant polymerase stops when it reaches the uracil inserted between the A14 and ME sequences of the inserted first transposon sequence. The tagmented nucleic is denatured and the second indexing oligonucleotide hybridizes to the tagmented nucleic followed by enzymatic extension. The dual-indexed nucleic acid can be used for sequencing or further processed, including but not limited to amplification The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The disclosure is not limited to the exact details shown and described, for variations obvious to one skilled in the art will be included within the disclosure defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present disclosure. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

---

The invention claimed is:

1. A method for producing a sequencing library comprising:

providing a plurality of double stranded symmetric modified target nucleic acids comprising a first adapter sequence at each end, wherein the first adapter sequence comprises a DNA lesion, with the proviso that the first adapter does not comprise a universal molecular identifier;

extending the modified target nucleic acids with a lesion-intolerant polymerase to generate a plurality of single stranded asymmetric modified target nucleic acids comprising at the 5' end of each strand the first adapter sequence and at the 3' end of each strand the complement of a portion of the first adapter;

annealing a primer to the plurality of single stranded asymmetric modified target nucleic acids, the primer comprising from 5' to 3' a second adapter sequence and an annealing domain, the annealing domain comprising a nucleotide sequence that anneals to the complement of the portion of the first adapter of the plurality of single stranded asymmetric modified target nucleic acids;

extending the 3' end of the annealed asymmetric modified target nucleic acids with a lesion-intolerant polymerase using the primer as template, wherein the extending results in a plurality of asymmetric modified target nucleic acids comprising from 5' to 3' (i) the first adapter, (ii) the target nucleic acid, (iii) the complement of the portion of the first adapter, and (iv) the complement of the second adapter.

2. The method of claim 1, wherein the plurality of symmetric modified target nucleic acids are double stranded and each strand comprises, from 5' to 3', the first adapter sequence comprising the DNA lesion, the target nucleic acid, a gap comprising at least one nucleotide, and the complement of a portion of the first adapter sequence without the DNA lesion.

3. The method of claim 1, wherein the DNA lesion comprises at least one of an abasic site, a modified base, a mismatch, a single-stranded break, or cross-linked nucleotides.

4. The method of claim 1, wherein the first adapter comprises one or more universal sequences, one or more index sequences, or a combination thereof.

5. The method of claim 1, wherein the target nucleic acids are from nucleic acids originating from a single cell, and wherein the nucleic acids comprise RNA or DNA.

6. The method of claim 1, wherein the target nucleic acids are from nucleic acids originating from a plurality of cells, and wherein the nucleic acids comprise RNA or DNA.

7. The method of claim 6, wherein the RNA comprises mRNA.

8. The method of claim 6, wherein the DNA comprises whole cell genomic DNA.

9. The method of claim 4, wherein the method comprises combinatorial indexing.

10. The method of claim 1, further comprising amplifying the asymmetric modified target nucleic acids, wherein the amplifying comprises a second primer and a lesion-tolerant polymerase, wherein the second primer comprises a nucleotide sequence that anneals to the first adapter sequence or the complement thereof.

11. The method of claim 1, wherein subsets of the plurality of asymmetric modified target nucleic acids are present in a plurality of compartments, wherein the compartments comprise a well or a droplet.

12. The method of claim 1, wherein the providing comprises (i) contacting a plurality of DNA fragments with the first adapter under conditions to ligate the first adapter to both ends of the DNA fragments, or (ii) contacting DNA with a transposome complex, wherein the transposome complex comprises a transposase and the first adapter, wherein the contacting occurs under conditions suitable for ligation of the first adapter into the DNA to generate the double stranded symmetric modified target nucleic acids.

13. The method of claim 1, further comprising:

providing a surface comprising a plurality of amplification sites, wherein the amplification sites comprise at least two populations of attached single stranded capture oligonucleotides having a free 3' end, and contacting the surface comprising amplification sites with the plurality of asymmetric modified target nucleic acids under conditions suitable to produce a plurality of amplification sites that each comprise a clonal population of amplicons from an individual asymmetric modified target nucleic acid.

14. The method of claim 1, wherein the 3' end of the primer is blocked.

15. The method of claim 14, wherein the 3' end of the primer comprises a dideoxynucleotide.

16. The method of claim 5, wherein the RNA comprises mRNA.

17. The method of claim 5, wherein the DNA comprises whole cell genomic DNA.

18. The method of claim 1, wherein the annealing domain of the primer comprises at least one altered nucleotide that increases the melting temperature compared to the corresponding native DNA nucleotide.

19. The method of claim 18, wherein the at least one altered nucleotide comprises a locked nucleic acid or a bridged nucleic acid.

* * * * *